US009615972B2

(12) United States Patent
Shibata et al.

(10) Patent No.: US 9,615,972 B2
(45) Date of Patent: Apr. 11, 2017

(54) OPHTHALMIC LASER SURGERY APPARATUS, AND EYEBALL FIXING PORTION MOVEMENT UNIT AND EYEBALL FIXING UNIT USED IN THE SAME

(71) Applicant: NIDEK CO., LTD., Gamagori, Aichi (JP)

(72) Inventors: Takayoshi Shibata, Gamagori (JP); Masakazu Endo, Okazaki (JP); Tomohiro Miyagi, Toyokawa (JP); Michihiro Takii, Nukata (JP); Masaaki Hanebuchi, Nukata (JP)

(73) Assignee: NIDEK CO., LTD., Gamagori (JP)

( * ) Notice: Subject to any disclaimer, the term of this patent is extended or adjusted under 35 U.S.C. 154(b) by 218 days.

(21) Appl. No.: 14/635,651

(22) Filed: Mar. 2, 2015

(65) Prior Publication Data

US 2015/0335479 A1    Nov. 26, 2015

(30) Foreign Application Priority Data

Feb. 28, 2014 (JP) ................................. 2014-039336
Feb. 28, 2014 (JP) ................................. 2014-039337

(Continued)

(51) Int. Cl.
*A61F 9/009* (2006.01)
*A61F 9/008* (2006.01)

(52) U.S. Cl.
CPC .......... *A61F 9/009* (2013.01); *A61F 9/00825* (2013.01); *A61F 9/008* (2013.01); *A61F 2009/00851* (2013.01)

(58) Field of Classification Search
None
See application file for complete search history.

(56) References Cited

U.S. PATENT DOCUMENTS

| 6,254,595 B1 | 7/2001 | Juhasz et al. |
| 2002/0103481 A1 | 8/2002 | Webb et al. |

(Continued)

FOREIGN PATENT DOCUMENTS

| JP | 2000-116694 A | 4/2000 |
| JP | 2004-531344 A | 10/2004 |

(Continued)

OTHER PUBLICATIONS

Jul. 7, 2015 Search Report issued in European Application No. 15156954.8.

*Primary Examiner* — Brian T Gedeon
(74) *Attorney, Agent, or Firm* — Oliff PLC

(57) ABSTRACT

An ophthalmic laser surgery apparatus includes an irradiation optical system and including an objective lens, and treats a patient's eye by using a laser beam. The ophthalmic laser surgery apparatus includes a delivery unit that includes an irradiation end unit, includes at least a portion of the irradiation optical system, and optically guides the laser beam, a first movement unit that includes a first drive section and integrally moves the irradiation end unit and an eyeball fixing unit which is connected to the delivery unit and fixes the patient's eye, a second movement unit that includes a second drive section and moves the eyeball fixing unit by driving the second drive section, and drive control means for controlling driving of the first drive section and driving of the second drive section, and individually moving the first movement unit and the second movement unit.

17 Claims, 20 Drawing Sheets

(30) Foreign Application Priority Data

Mar. 31, 2014 (JP) .................................. 2014-074967
Mar. 31, 2014 (JP) .................................. 2014-074968

(56) References Cited

U.S. PATENT DOCUMENTS

| | | |
|---|---|---|
| 2009/0131921 A1 | 5/2009 | Kurtz et al. |
| 2011/0190739 A1 | 8/2011 | Frey et al. |
| 2012/0283708 A1 | 11/2012 | Raksi et al. |
| 2013/0165911 A1 | 6/2013 | Raksi et al. |
| 2013/0338648 A1 | 12/2013 | Hanebuchi et al. |
| 2013/0338649 A1 | 12/2013 | Hanebuchi et al. |

FOREIGN PATENT DOCUMENTS

| | | |
|---|---|---|
| JP | 2010-538700 A | 12/2010 |
| JP | 2013-248303 A | 12/2013 |
| JP | 2013-248304 A | 12/2013 |

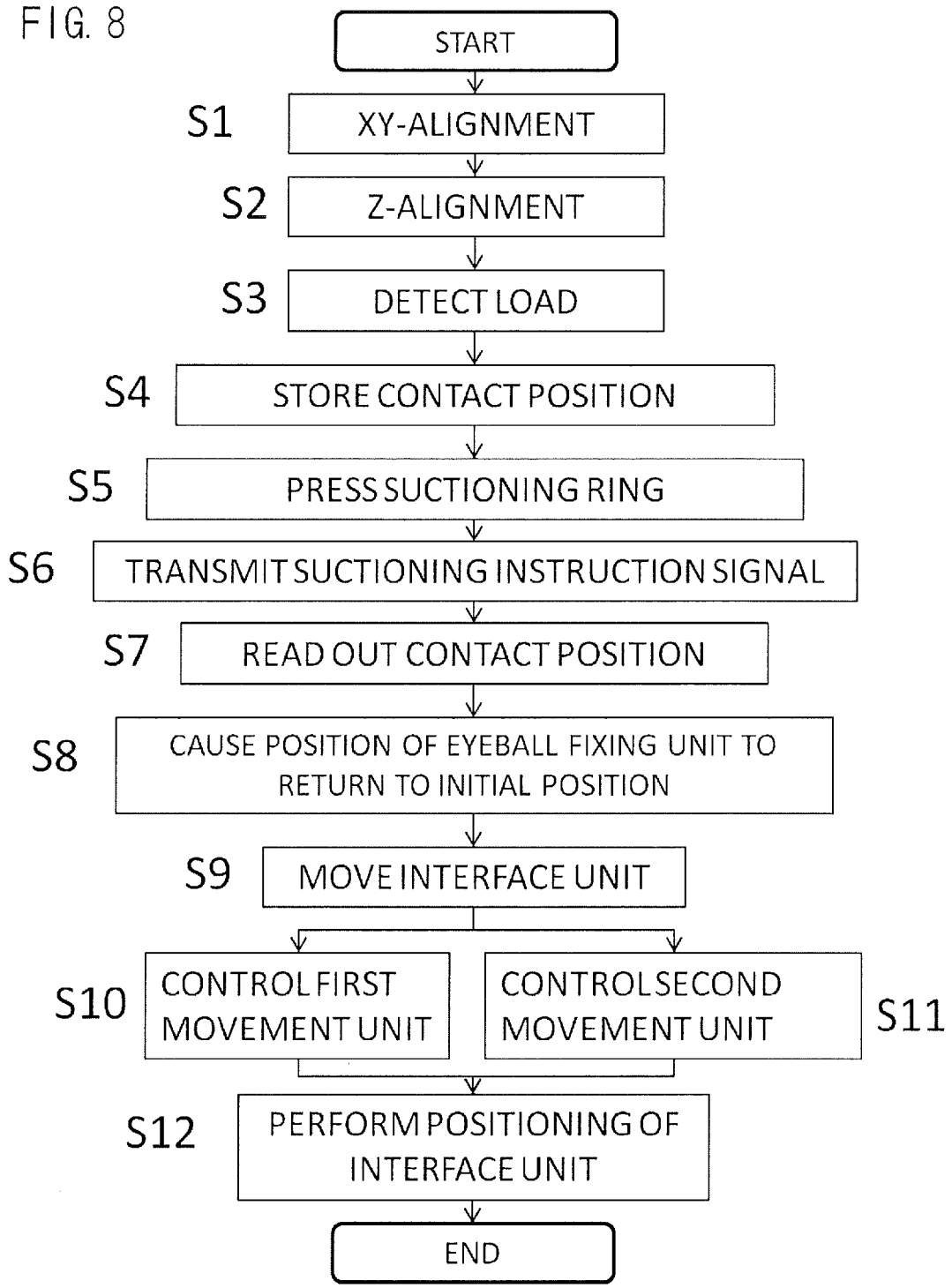

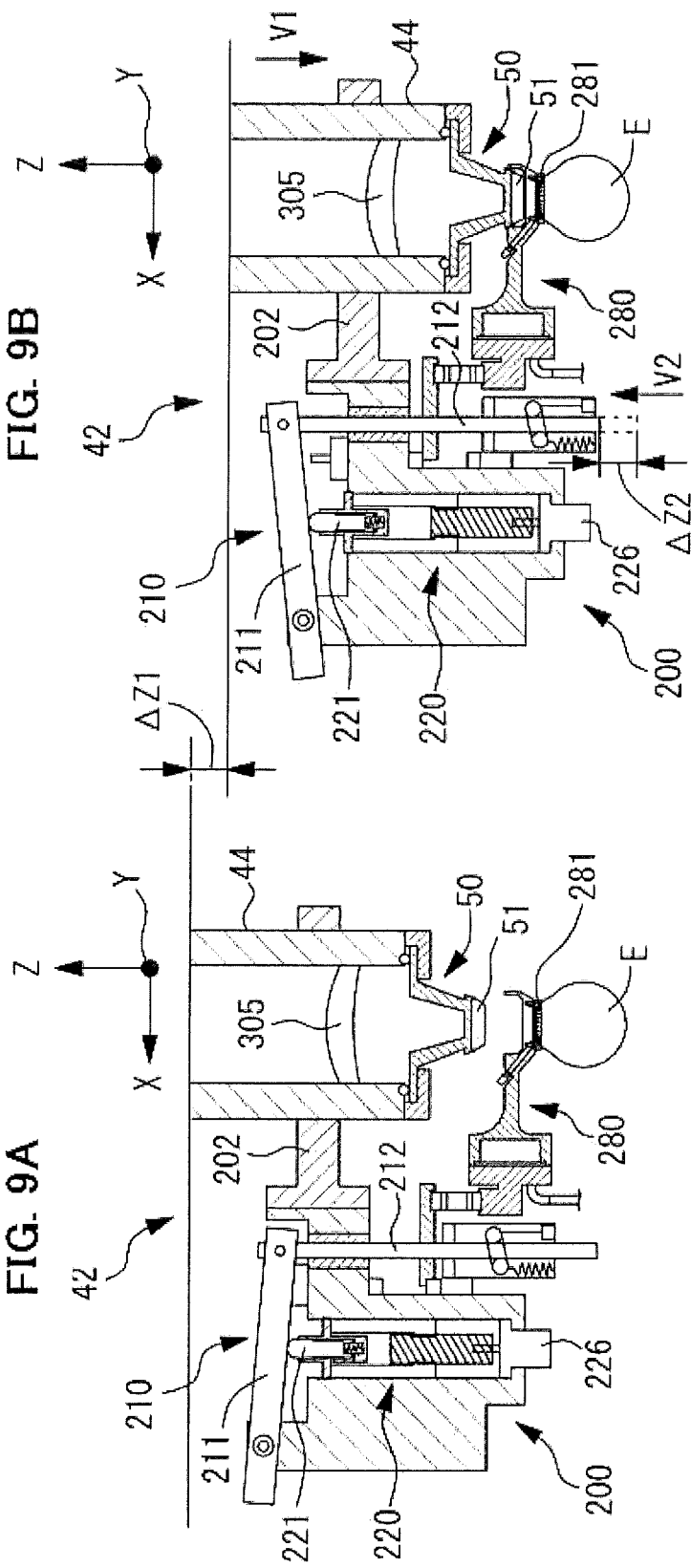

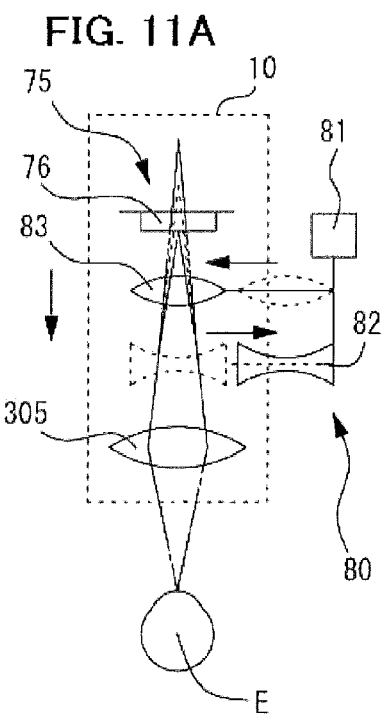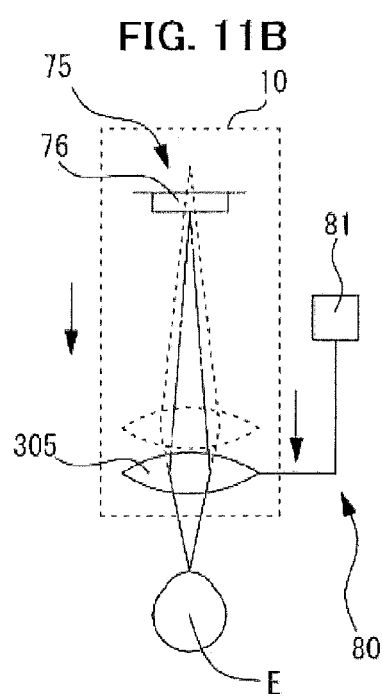

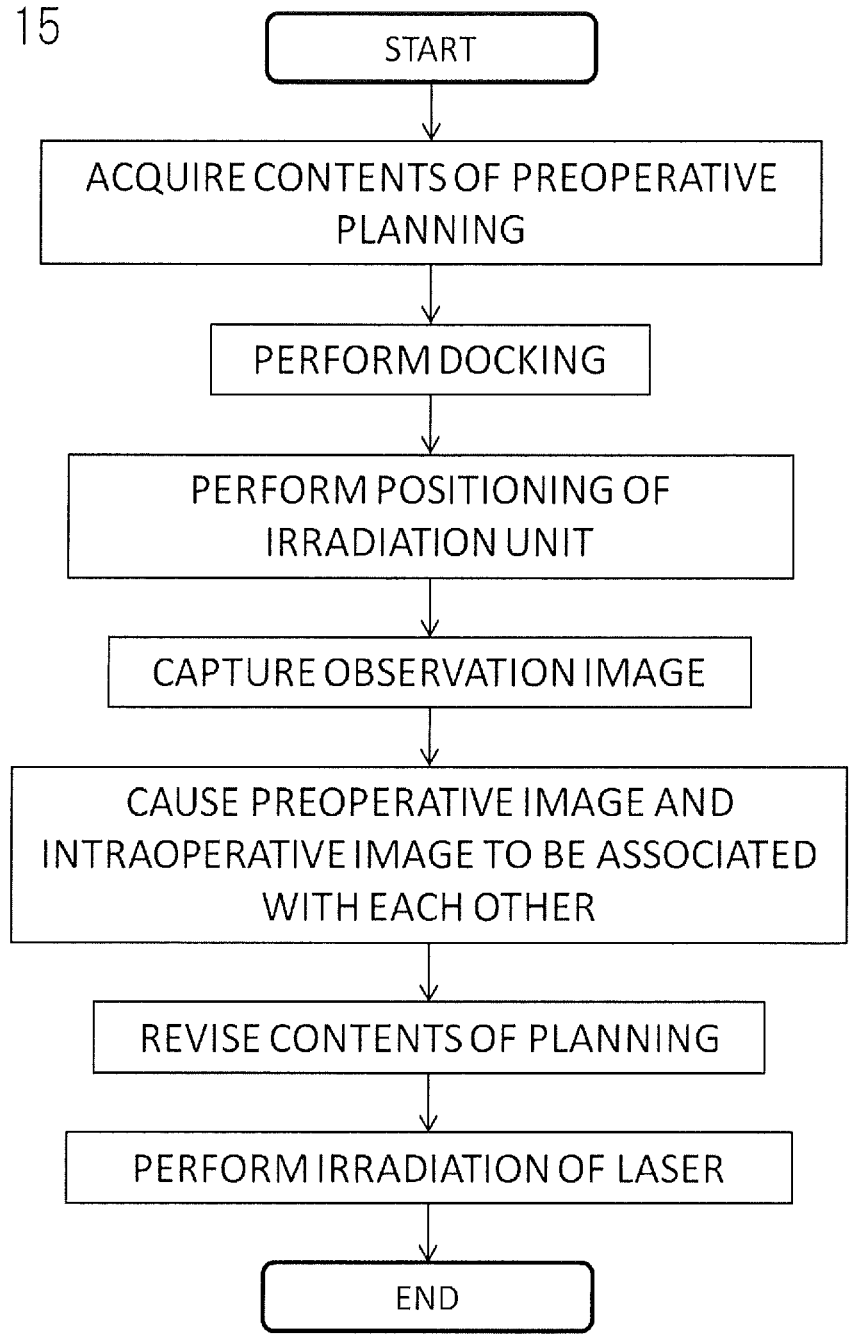

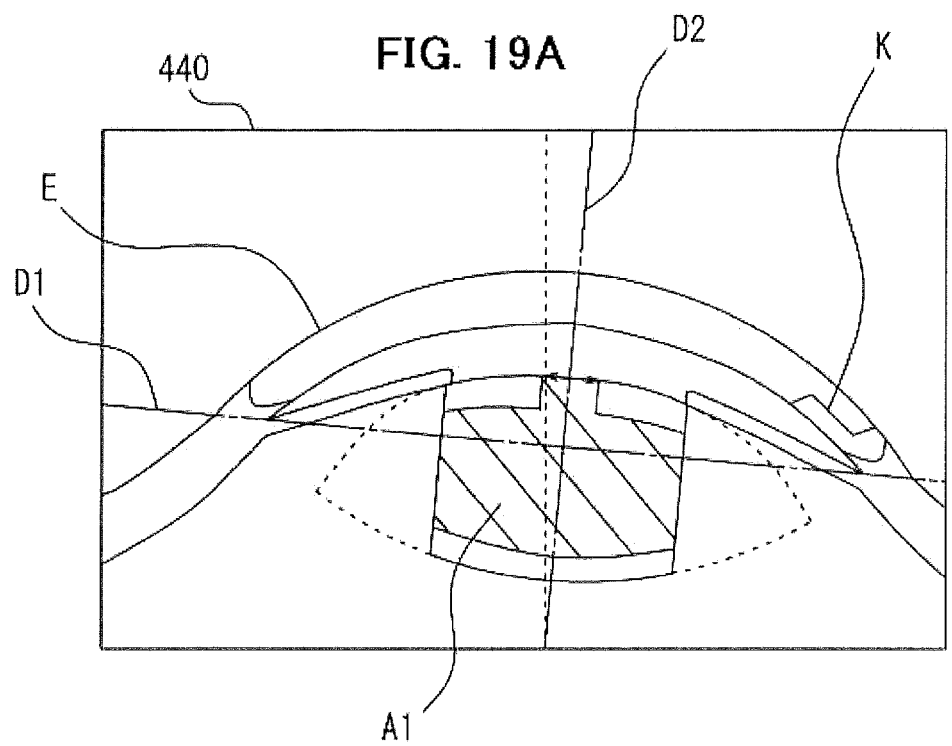
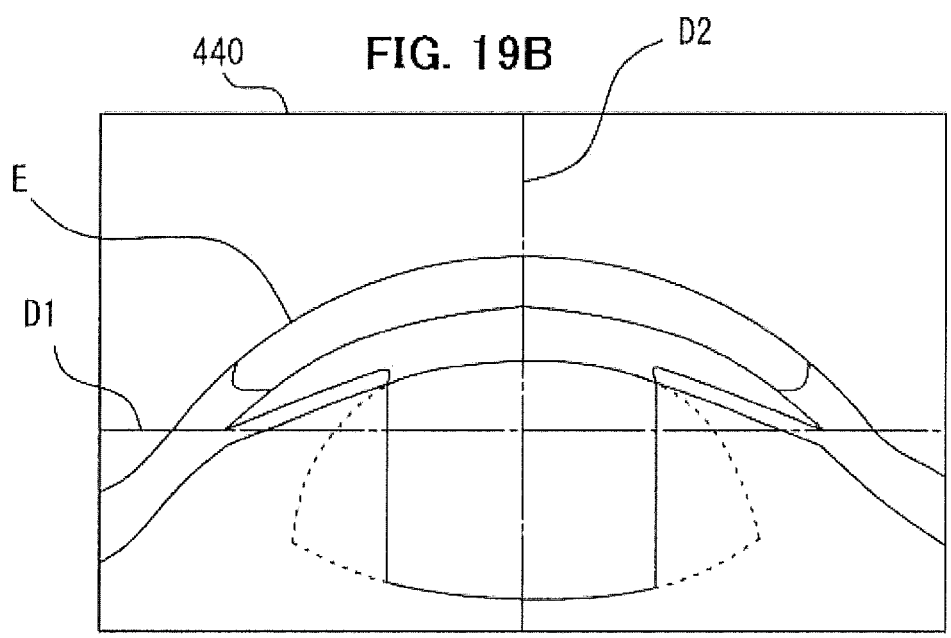

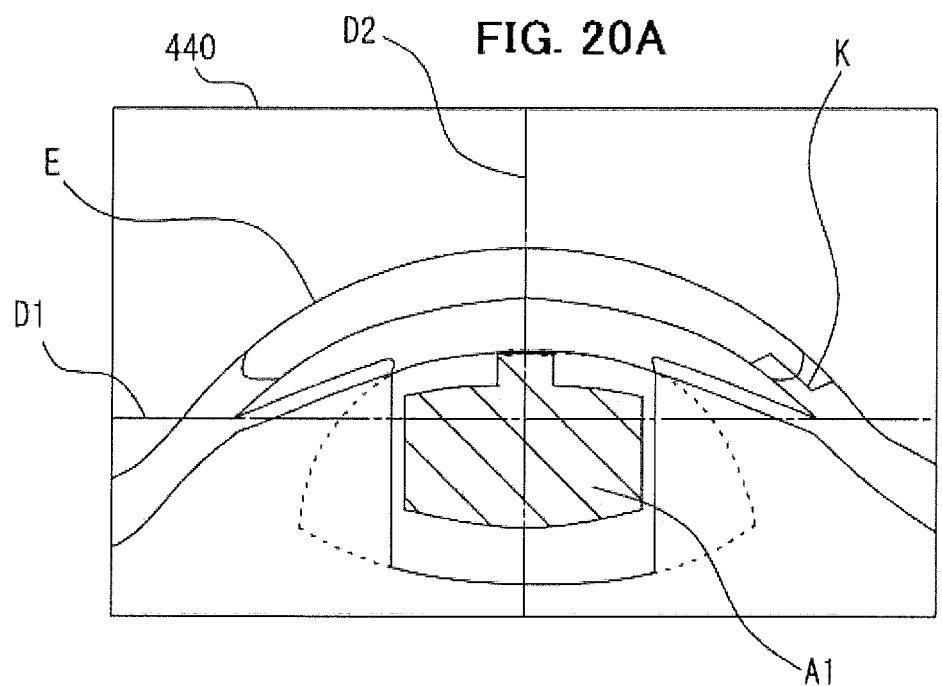
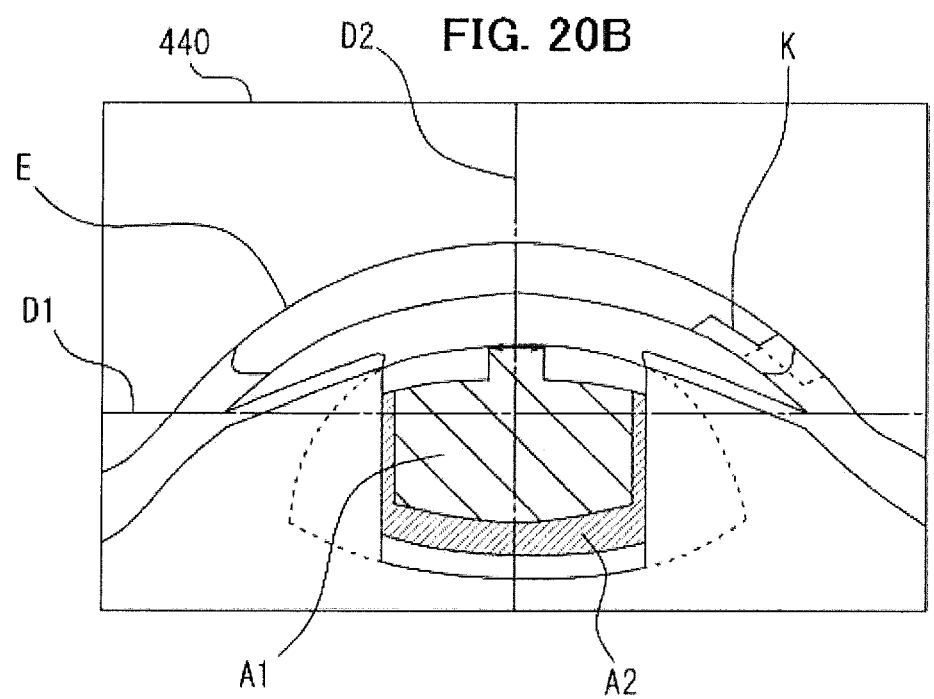

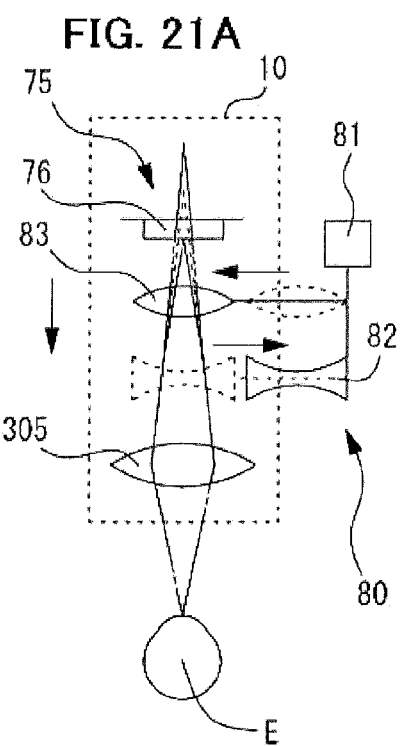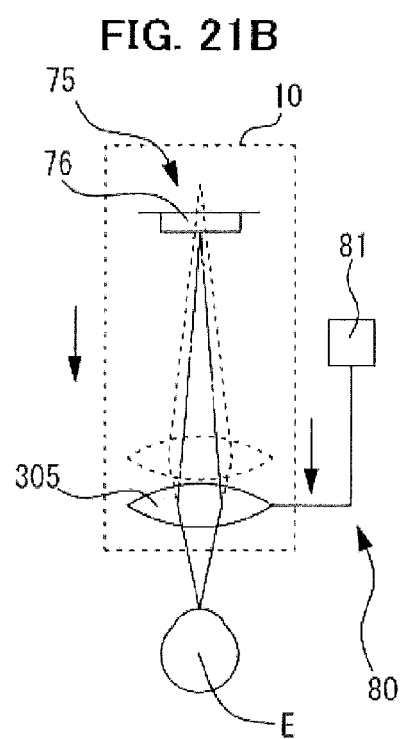

OPHTHALMIC LASER SURGERY APPARATUS, AND EYEBALL FIXING PORTION MOVEMENT UNIT AND EYEBALL FIXING UNIT USED IN THE SAME

CROSS REFERENCE TO RELATED APPLICATIONS

This application is based upon and claims the benefit of priorities of Japanese Patent Application No. 2014-039336 filed on Feb. 28, 2014, Japanese Patent Application No. 2014-039337 filed on Feb. 28, 2014, Japanese Patent Application No. 2014-074967 filed on Mar. 31, 2014 and Japanese Patent Application No. 2014-074968 filed on Mar. 31, 2014 the contents of which are incorporated herein by reference in its entirety.

TECHNICAL FIELD

The present disclosure relates to an ophthalmic laser surgery apparatus for treating a patient's eye by irradiating the patient's eye with a laser beam, and an eyeball fixing portion movement unit and an eyeball fixing unit which are used in the ophthalmic laser surgery apparatus.

BACKGROUND ART

Recently, a technology of treating (for example, cutting and crushing) a tissue such as the crystalline lens of a patient's eye (the cornea of a patient's eye) by performing irradiation with a laser beam has been proposed. For example, in an apparatus disclosed with reference to Patent Documents 1 and 2, a laser is concentrated on a target position of an ocular tissue, thereby forming a laser spot. As a result, the ocular tissue is mechanically disrupted (cut).

Such an apparatus includes an adsorption unit (an eyeball fixing unit) which adsorbs an eyeball in order to prevent the eyeball from moving during laser irradiation, and an interface unit (for example, a contact unit and a liquid interface) which optically guides (performs positioning of an optical system) the laser spot accurately.

RELATED ART DOCUMENT

Patent Document

[Patent Document 1] JP-A-2000-116694
[Patent Document 2] JP-T-2004-531344
[Patent Document 3] JP-A-2013-248303

In an apparatus of Patent Document 1, an adsorption unit (a suctioning ring) and an interface unit are integrated with each other so that a fixation state (an applanation state of the cornea) or the like of a patient's eye cannot be adjusted. In an apparatus of Patent Document 2, the adsorption unit and the interface unit are separated from each other so that the interface unit needs an operation to be held by the adsorption unit, thereby resulting in inconvenience. In an apparatus of Patent Document 3, when an entire casing including an objective lens is moved toward the patient's eye, it is relatively difficult to control a pressing force against the patient's eye, due to cushioning properties of a spring mechanism.

As described above, the apparatuses of the related art in present states have various problems, and there is room for improvement.

SUMMARY

The present disclosure technically aims to provide an ophthalmic laser surgery apparatus which can solve at least one of the above-described problems of the related art, and an eyeball fixing portion movement unit and an eyeball fixing unit which are used in the ophthalmic laser surgery apparatus.

The present disclosure has a configuration described below in order to solve the problems.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a first movement unit that includes a first drive section and is provided to integrally move the irradiation end unit and an eyeball fixing unit which is connected to the delivery unit and fixes the patient's eye onto an optical axis of the objective lens, toward the patient's eye by driving the first drive section;

a second movement unit that includes a second drive section and is provided to move the eyeball fixing unit with respect to the irradiation end unit by driving the second drive section; and a drive controller that controls driving of the first drive section and driving of the second drive section and individually moves the first movement unit and the second movement unit.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a first movement unit that includes a first drive section and is provided to integrally move the irradiation end unit and an eyeball fixing unit which is connected to the delivery unit and fixes the patient's eye onto an optical axis of the objective lens toward the patient's eye by driving the first drive section; and a second movement unit that is provided to move the eyeball fixing unit with respect to the irradiation end unit, wherein a main body of the second movement unit is connected to the delivery unit through a connection member and is arranged at a position away from a casing of the irradiation end unit, and wherein the second movement unit pressurizes the patient's eye with the eyeball fixing unit at a load equal to or less than 300 g, and more preferably equal to or less than 200 g.

An eyeball fixing portion movement unit which is detachably attached to an ophthalmic laser surgery apparatus including an irradiation optical system for irradiating a patient's eye with a laser beam emitted from a laser source and including an objective lens concentrating the laser beam on a tissue of the patient's eye, and treats the patient's eye by using the laser beam, wherein the ophthalmic laser surgery apparatus has a delivery unit which includes an irradiation end unit containing the objective lens, includes at least a portion of the irradiation optical system, and optically guides the laser beam to the patient's eye and has an emission portion movement unit which includes a first drive section and is provided to integrally move the irradiation end unit and an eyeball fixing unit which is connected to the delivery unit and fixes the patient's eye onto an optical axis of the objective lens, toward the patient's eye by driving the first drive section, and wherein the eyeball fixing portion movement unit includes a second drive section for moving the eyeball fixing unit with respect to the irradiation end unit and includes a drive controller which controls driving of the second drive section so as to cancel a movement of the eyeball fixing unit caused by the emission portion movement unit when the emission portion movement unit moves the irradiation end unit and the eyeball fixing unit toward the patient's eye by driving the first drive section.

An eyeball fixing unit which is used in a surgical operation adopting an ophthalmic laser surgery apparatus for treating a patient's eye by using a laser beam, the unit comprising:

a ring-shaped suctioning ring that includes a suctioning port and is brought into contact with the patient's eye;

an arm that holds the suctioning ring portion and is connected to the ophthalmic laser surgery apparatus; and a suctioning pipe that performs suctioning of the patient's eye through the suctioning port, wherein an attachment/detachment portion for being attached to and detached from any one of a delivery unit which is provided in the ophthalmic laser surgery apparatus and is movable with respect to the patient's eye by driving a drive section, and a movement unit which includes the drive section for moving the eyeball fixing unit and is connected to the delivery unit are formed at a tip end of the arm on the ophthalmic laser surgery apparatus side.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a movement unit that is provided so as to move an eyeball fixing unit for fixing the patient's eye onto an optical axis of a laser irradiation unit, toward the patient's eye;

an eye detector that detects the patient's eye before being fixed by the eyeball fixing unit based on a captured image captured by an imaging optical system for capturing an image of the patient's eye; and a controller that controls driving of a drive section based on a detection signal from the eye detector and automatically moves the eyeball fixing unit with respect to the patient's eye before being fixed by the eyeball fixing unit.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation optical system by driving the drive section;

an eye detector that detects the patient's eye before being fixed by an eyeball fixing unit based on a captured image captured by an imaging optical system for capturing an image of the patient's eye; and a fixation induction unit that moves a presentation position of a fixation target to be presented to the patient's eye and induces a fixation direction of the patient's eye, wherein after performing automatic positioning by controlling the drive section so as to cause the patient's eye and the irradiation optical system to be in a predetermined positional relationship based on a detection result of the eye detector, a controller controls the fixation induction unit so as to automatically present the fixation target for causing an optical axis of irradiation and an optical axis of the patient's eye to coincide with each other and controls the drive section again so as to automatically move the movement unit to be in the predetermined positional relationship again with respect to misalignment generated by moving the presentation position of the fixation target.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation end unit by driving the drive section;

an eye detector that detects the patient's eye before being fixed by an eyeball fixing unit based on a captured image captured by an imaging optical system for capturing an image of the patient's eye;

a fixation induction unit that moves a presentation position of a fixation target to be presented to the patient's eye and induces a fixation direction of the patient's eye; and a controller that controls the fixation induction unit so as to automatically present the fixation target for causing an optical axis of irradiation and an optical axis of the patient's eye to coincide with each other and controls the drive section again so as to automatically move the movement unit to be in the predetermined positional relationship again with respect to misalignment generated by moving the presentation position of the fixation target after performing automatic positioning by controlling the drive section so as to cause the patient's eye and the irradiation optical system to be in a predetermined positional relationship based on a detection result of the eye detector.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation end unit by driving the drive section;

an eye detector that detects the patient's eye before being fixed by an eyeball fixing unit based on a captured image captured by an imaging optical system for capturing an image of the patient's eye;

an observation optical system that has the light receiving element and is provided in a laser irradiation unit in order to capture an anterior chamber observation image of the patient's eye by using the light receiving element; and a focus adjuster that adjusts focus of the observation optical system with respect to the patient's eye, wherein the focus adjuster can revise focus deviation of the observation optical system caused by driving of the movement unit, wherein the eye detector detects an alignment state of the patient's eye with respect to the irradiation optical system by using the anterior chamber observation image which is revised by the focus adjuster, and wherein the ophthalmic laser surgery apparatus also controls the drive section based on an alignment detection result performed by the eye detector and moves at least a portion of the irradiation end unit with respect to the patient's eye.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move the irradiation end unit including the objective lens toward the patient's eye by driving the drive section;

an observation optical system that is provided in the irradiation end unit so as to observe the anterior chamber of the patient's eye; and a focus adjuster that adjusts focus of the observation optical system with respect to the anterior chamber.

An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit in which a light source for performing irradiation with illumination light is arranged so as to form the luminescent spot on the cornea of the patient's eye and which contains the objective lens, includes at least a portion of the irradiation optical system, and optically guides the laser beam to the patient's eye;

a movement unit that includes a drive section and is provided to move the irradiation end unit including the objective lens toward the patient's eye by driving the drive section; and an observation optical system that is provided in the irradiation end unit so as to observe the anterior chamber of the patient's eye, wherein the observation optical system can capture an anterior chamber image of the patient's eye including a first cornea reflection image which is formed by illumination light passing through the outside of an interface having a light-transmitting optical member covering at least a portion of the cornea of the patient's eye, and a second cornea reflection image which is formed by illumination light passing through the inside of the interface, and wherein the ophthalmic laser surgery apparatus includes an alignment detector that detects a position of the patient's eye based on at least one of the first cornea reflection image and the second cornea reflection image captured by the observation optical system.

An ophthalmic laser surgery apparatus which includes a scanning optical system performing three-dimensional scanning with a laser beam emitted from a laser source and irradiates each target position corresponding to a preset treatment region with the laser beam so as to treat a patient's eye, the apparatus comprising:

a variation information acquisition unit that acquires a first data set related to a structure of the patient's eye acquired to establish prior planning of a treatment region including the inside of a tissue of the patient's eye, and a second data set related to a structure of the patient's eye acquired when performing treatment by using the laser beam based on the planned treatment region after the planning of the treatment region is established so as to obtain variation information of the patient's eye which is at least any one of structural variation information of the patient's eye and variation information of a sight direction of the patient's eye by comparing the first data set and the second data set.

BRIEF DESCRIPTION OF THE DRAWINGS

FIG. 8 is a flowchart showing a control operation of the present example.

FIGS. 9A and 9B are diagrams for illustrating a method of controlling first and second movement units.

FIGS. 11A and 11B are diagrams for illustrating a modification example the focal adjustment unit.

FIG. 15 is a flowchart showing the control operation of the present example.

FIGS. 19A and 19B are diagrams for illustrating planning.

FIGS. 20A and 20B are diagrams for illustrating a correction of contents of planning.

FIGS. 21A and 21B are diagrams illustrating a modification example of the tomographic image capturing unit.

DESCRIPTION OF ILLUSTRATIVE EMBODIMENTS

<Overview>

Hereinafter, an overview will be described regarding an illustrative embodiment of the present disclosure. In an ophthalmic laser surgery apparatus (hereinafter, also referred to as the apparatus or a surgical operation apparatus, refer to FIG. 1) 1 of the present example, a laser beam is concentrated on a tissue of a patient's eye E, thereby treating the patient's eye E. For example, the apparatus 1 may include an irradiation optical system 320 (refer to FIG. 3). For example, the irradiation optical system 320 irradiates the patient's eye E with a laser beam emitted from a laser source. For example, the irradiation optical system 320 may include an objective lens 305 for concentrating a laser on a tissue of the patient's eye E.

Figure 3:
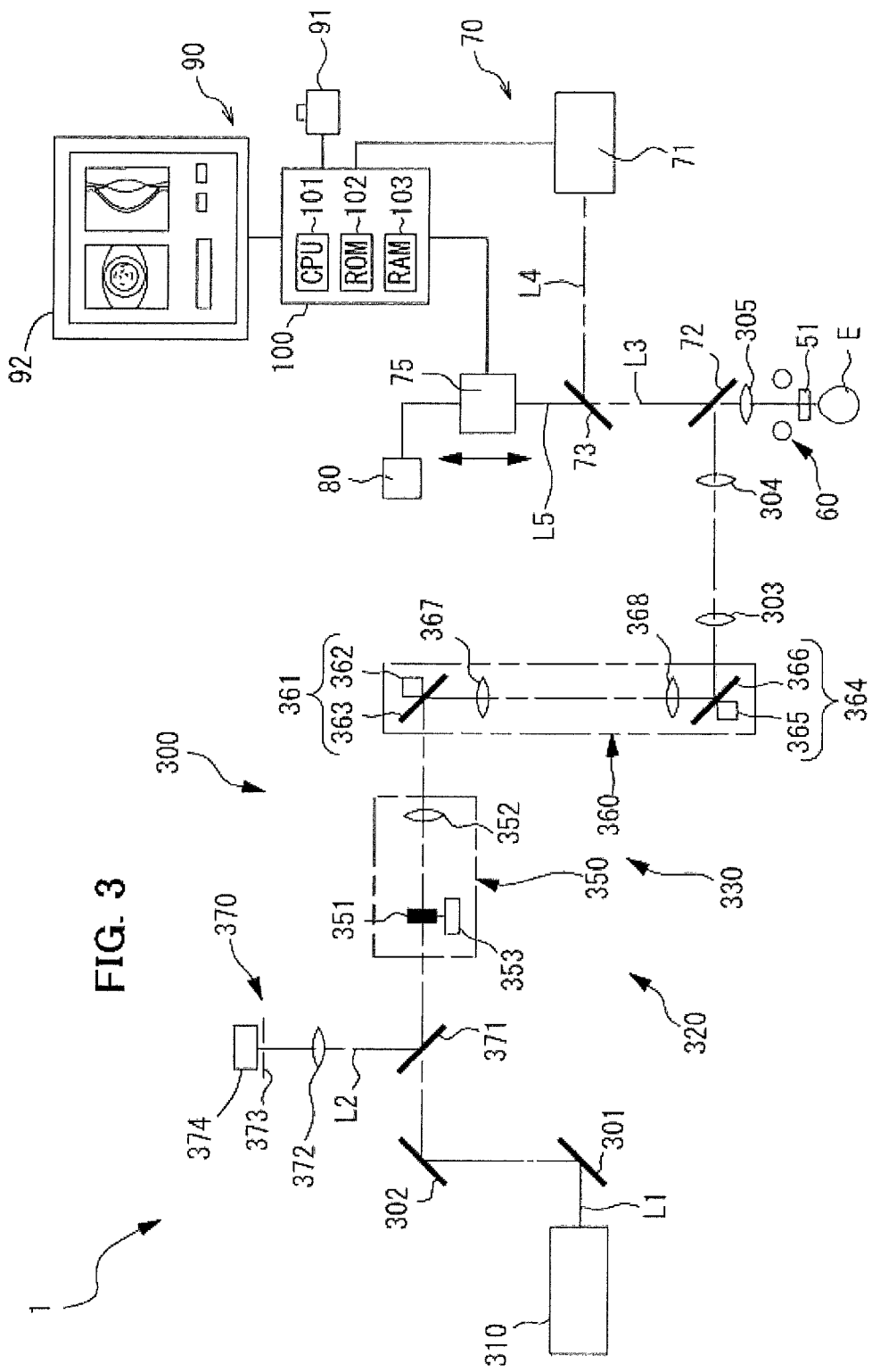
FIG. 3 is a schematic diagram showing an internal configuration of the present example.
Figure 4:
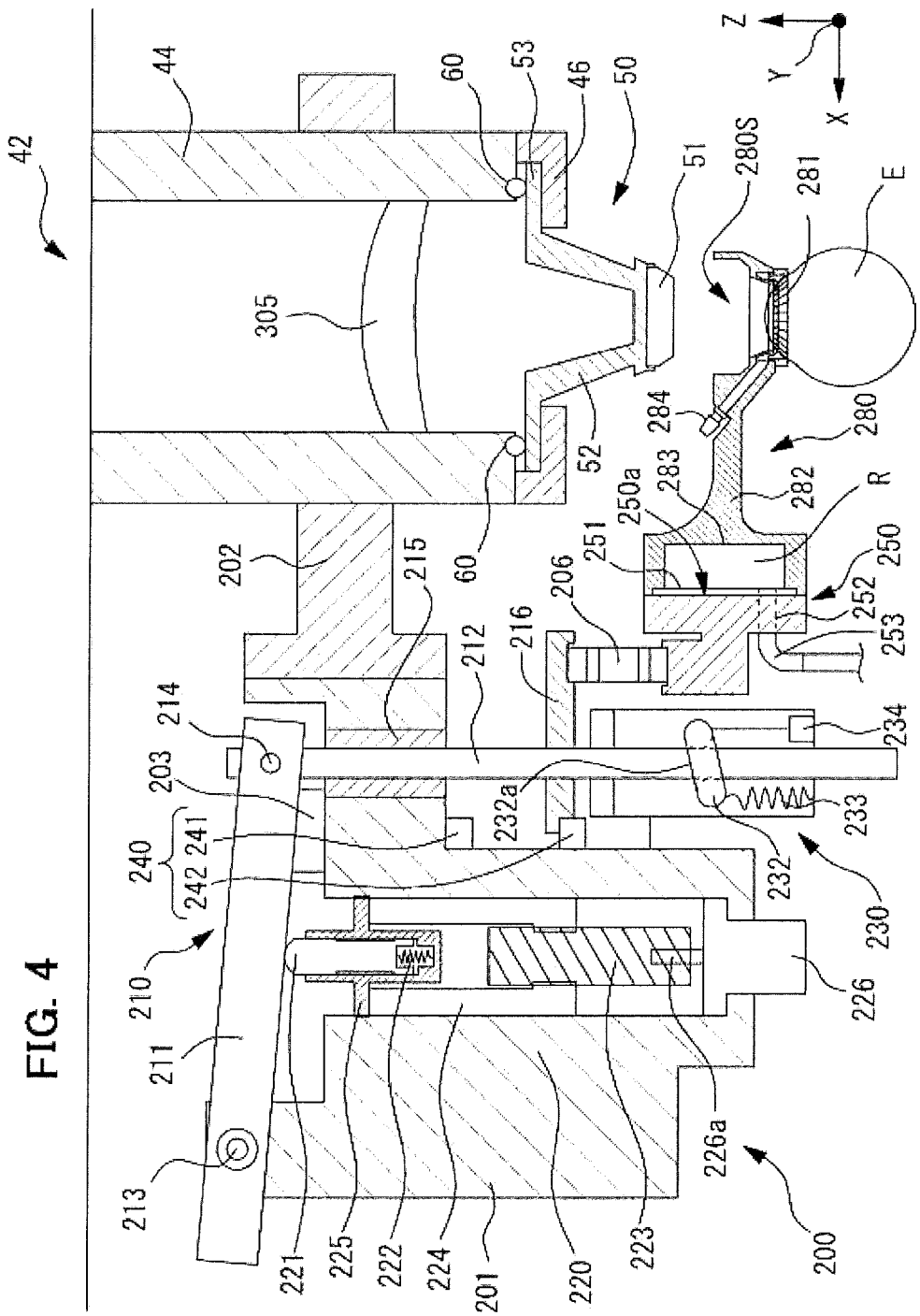
FIG. 4 is a diagram for illustrating a second movement unit of the present example.

In the present example, the surgical operation apparatus 1 mainly includes a delivery unit 41, a first movement unit 10, a second movement unit 200, and a drive control section (for example, a control unit 100) (refer to FIGS. 3 and 4). For example, the delivery unit 41 optically guides a laser beam to the patient's eye E. For example, the delivery unit 41 may include an irradiation end unit 42, and at least a portion of the irradiation optical system 320. The irradiation end unit 42 contains the objective lens 305. The objective lens 305 may be arranged at a position facing the patient's eye E. The objective lens 305 may be configured to be one or multiple. The apparatus 1 may include a main body portion 2 in which the laser source can be accommodated (refer to FIG. 1).

For example, the first movement unit 10 (refer to FIG. 1) may include a first drive section 12. The first movement unit 10 may integrally move the irradiation end unit 42 and an eyeball fixing unit 280 toward the patient's eye E by driving the first drive section 12. For example, the eyeball fixing unit 280 is connected to the delivery unit 41 and fixes the patient's eye E onto an optical axis of the objective lens 305.

For example, the second movement unit 200 (refer to FIG. 4) may include a second drive section 226. The second drive section 226 is arranged separately from the first drive section 12. For example, the second movement unit 200 may move the eyeball fixing unit 280 with respect to the irradiation end unit 42 or the objective lens 305 by driving the second drive section 226.

Figure 7:
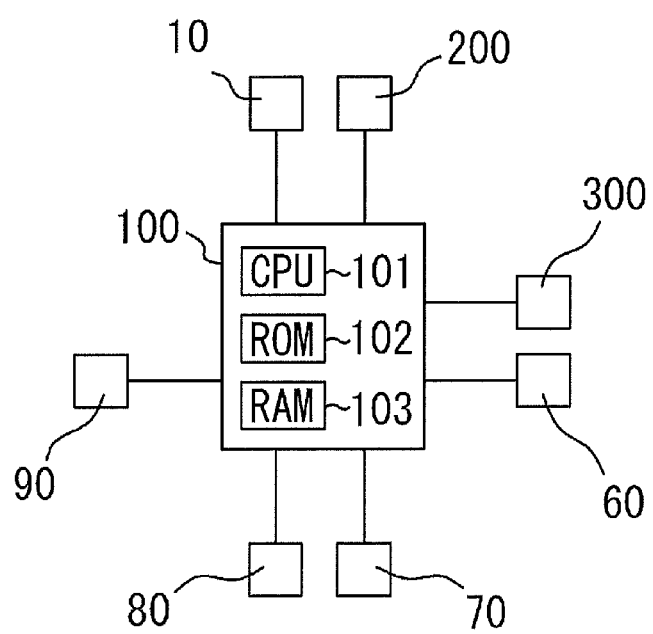
FIG. 7 is a block diagram showing a control system of the present example.

For example, the drive control section (refer to FIG. 7) may control driving of the first drive section 12 and the second drive section 226. For example, the drive control section may control driving of the first drive section 12 so as to cause the first movement unit 10 to move the irradiation end unit 42 and the eyeball fixing unit 280 with respect to the patient's eye E. In this case, the drive control section may control driving of the second drive section 226 so as to move the eyeball fixing unit 280 in a direction in which a movement of the eyeball fixing unit 280 caused by the first movement unit 10 is cancelled.

After controlling driving of the first drive section 12, causing the first movement unit 10 to move the irradiation end unit 42 and the eyeball fixing unit 280 toward the patient's eye E, and completing positioning of the irradiation end unit 42 with respect to the patient's eye E, the drive control section may control driving of the second drive section 226 so as to cause the second movement unit 200 to move the eyeball fixing unit 280 toward the patient's eye E.

For example, the drive control section controls the first movement unit 10 and moves the irradiation end unit 42. For example, the drive control section moves the irradiation end unit 42 to an irradiation position where the patient's eye E can be irradiated with a laser. Thereafter, the drive control section may control the second movement unit 200 so as to move the eyeball fixing unit 280 toward the patient's eye E. Then, the drive control section may bring the eyeball fixing unit 280 into contact with the patient's eye E, thereby starting adsorptive fixing of an eyeball.

For example, in the surgical operation apparatus 1 of the present example, the eyeball fixing unit 280 is individually movable with respect to the irradiation end unit 42 by the second movement unit 200. Therefore, an increase of ocular tension of the patient's eye E caused by a movement of the first movement unit 10 can be adjusted. In other words, drive control means may control driving of the second drive section so as to control a pressure applied to the patient's eye by the eyeball fixing unit 280.

The second movement unit 200 may pressurize the patient's eye E with the eyeball fixing unit 280 at a load equal to or less than 500 g, preferably equal to or less than 300 g, and more preferably equal to or less than 200 g, for example.

An interface unit 50 (refer to FIG. 4) may be connected to the irradiation end unit 42. For example, the interface unit 50 has a transmissive optical member (for example, a cover glass 51) covering at least a portion of the cornea of the patient's eye E. For example, the cover glass 51 may be an applanated lens or an immersion lens. For example, the applanated lens transmits a laser and applanates the front surface of the cornea. For example, the interface unit 50 may integrally move together with the objective lens 305 and the eyeball fixing unit 280.

A movement toward the patient's eye E denotes a movement in a direction approaching the patient's eye E. Similarly, a movement toward the irradiation end unit 42 denotes a movement in a direction approaching the irradiation end unit 42.

For example, the first movement unit 10 and the second movement unit 200 do not have to three-dimensionally move in an XYZ-axis direction. Each of the movement units is acceptable as long as the movement units can move at least in an optical axis direction of the objective lens 305 (or in an axial direction of the patient's eye E).

When cancelling a movement of the eyeball fixing unit 280, a movement amount thereof does not have to completely coincide. For example, the eyeball fixing unit 280 may slightly move with respect to the patient's eye E. The absolute position of the eyeball fixing unit 280 may vary as long as the variation is not a burden to the patient's eye E.

The second movement unit 200 may be a movement mechanism in which a drive section and a spring mechanism are arranged. For example, the drive section may drive the eyeball fixing unit 280 which is movably held by the spring mechanism.

A main body of the second movement unit 200 may be connected to the delivery unit 41 through a connection member. In other words, the second movement unit 200 may be arranged at a position away from a casing of the irradiation end unit 42 (for example, a lens barrel 44). Accordingly, the size of the casing of the irradiation end unit 42 is miniaturized, and thus, it is possible to avoid the irradiation end unit 42 being in contact with the face of a patient.

When the irradiation end unit 42 and the eyeball fixing unit 280 are moved toward the patient's eye E by the first movement unit 10, the drive control section may control the second drive section 226 so as to cause a position of the eyeball fixing unit 280 to be constant with respect to the patient's eye E.

For example, the second movement unit 200 may include a base portion 201 and a movable member (for example, a link 211 and a link 212). For example, the base portion 201 is connected to the delivery unit 41 and is moved together with the irradiation end unit 42 by the first movement unit 10. For example, the movable member is movable with respect to the base portion 201 and is connected to the eyeball fixing unit 280. For example, the second drive section 226 may move the movable member with respect to the base portion 201.

When the base portion 201 is moved together with the irradiation end unit 42 by the first movement unit 10, the drive control section may move the movable member with respect to the base portion 201, thereby causing the position of the eyeball fixing unit 280 to be constant with respect to the patient's eye E.

For example, the second movement unit 200 may include a pressure sensor (for example, a load cell 206, refer to FIG. 4). For example, the pressure sensor may detect a pressure or a load to the patient's eye E applied by the eyeball fixing unit 280. The drive control section may control driving of at least any one of the first drive section 12 and the second drive section 226 based on a detection signal from the pressure sensor. For example, when a pressure is detected by the pressure sensor, driving of at least any one of the first drive section 12 and the second drive section 226 may be stopped. Accordingly, there is a case where a load applied to the patient's eye E can be lightened. For example, the drive control section may stop driving of the first drive section 12 based on the detection signal from the pressure sensor when the eyeball fixing unit 280 and the patient's eye E are detected to be in contact with each other.

The second movement unit 200 may include a position detection sensor (for example, an encoder 203, refer to FIG. 4). For example, the position detection sensor detects a height (for example, a distance or a position with respect to the patient's eye E) of the eyeball fixing unit 280. For example, the drive control section may control the first drive section and the second drive section based on positional information of the eyeball fixing unit 280 acquired by the position detection sensor. The drive control section may stop driving of the first drive section 12 based on the detection signal from the pressure sensor, when the eyeball fixing unit 280 and the patient's eye E are detected to be in contact with each other. In this case, a height of the eyeball fixing unit 280 detected by the position detection sensor may be stored in a memory as a reference position. Moreover, after moving the irradiation end unit 42 and the eyeball fixing unit 280 toward the patient's eye E by driving the first drive section 12, the irradiation end unit 42 and the eyeball fixing unit 280 may be returned to the reference position stored in the memory. Accordingly, the eyeball fixing unit 280 adheres to the patient's eye E, and thus, the eyeball fixing unit 280 can be stably fixed to the patient's eye E.

For example, the apparatus may include a lock mechanism (for example, a lock portion 230, refer to FIG. 4). For example, the lock mechanism locks the eyeball fixing unit 280 from moving. In this case, the drive control section may release the lock mechanism from locking the eyeball fixing unit 280 while the second drive section 226 is driving and may activate the lock mechanism to lock the eyeball fixing unit 280 while the second drive section 226 is stopped driving. Accordingly, the eyeball fixing unit 280 is suppressed from moving unexpectedly.

The eyeball fixing unit 280 may be detachably attached to the second movement unit 200. Since the eyeball fixing unit 280 is positioned by the second movement unit 200, inconvenience of a practitioner is decreased. Moreover, the eyeball fixing unit 280 can be easily replaced or sterilized.

The second movement unit (an eyeball fixing portion movement unit) 200 may be detachably attached to the surgical operation apparatus 1. For example, the second movement unit 200 may be detachably attached to the first movement unit (an emission portion movement unit) 10. For example, the second movement unit 200 may be detachably attached to the first movement unit 10 by the connection member (for example, an arm 202). An arm, a bolt, a magnet, a zipper and the like can be exemplified as the connection member. The drive control section may control driving of the second drive section 226 so as to cancel a movement of the eyeball fixing unit 280 caused by the first movement unit (the emission portion movement unit) 10.

For example, the eyeball fixing unit 280 is used in a surgical operation adopting the ophthalmic laser surgery apparatus 1 for treating the patient's eye E by using a laser beam. For example, the eyeball fixing unit 280 may include a suctioning ring 281, an arm (for example, a support portion 282), and a suctioning pipe 284. For example, the suctioning ring 281 may include a suctioning hole. The suctioning ring 281 has a ring shape and is brought into contact with the patient's eye E. For example, the arm may hold the suctioning ring 281 portion. For example, the arm may be connected to the ophthalmic laser surgery apparatus. For example, the suctioning pipe may perform suctioning of the patient's eye E through the suctioning hole.

For example, an attachment/detachment portion (for example, a connection portion 250) may be formed at a tip end of the arm on the ophthalmic laser surgery apparatus side. For example, the attachment/detachment portion may allow the eyeball fixing unit 280 to be detachably attached to any one of the delivery unit 41 and the first movement unit 10. For example, the delivery unit 41 may be provided in the ophthalmic laser surgery apparatus. Then, the delivery unit 41 may be movable with respect to the patient's eye E by driving the drive section 12. For example, the first movement unit 10 may include the drive section for moving the eyeball fixing unit 280 and may be connected to the delivery unit 41.

Hereinafter, an overview will be described regarding a second illustrative embodiment. In the ophthalmic laser surgery apparatus (hereinafter, also referred to as the apparatus or the surgical operation apparatus, refer to FIG. 1) 1 of the present example, a laser beam is concentrated on a tissue of the patient's eye E, thereby treating the patient's eye E. For example, the apparatus 1 may include the irradiation optical system 320. For example, the irradiation optical system 320 irradiates the patient's eye E with a laser beam emitted from the laser source. For example, the irradiation optical system 320 may include the objective lens 305 for concentrating a laser on a tissue of the patient's eye E.

For example, the surgical operation apparatus 1 of the present example mainly includes the delivery unit 41, movement units (for example, a first movement unit and a second movement unit), an observation optical system (for example, an observation/image capturing unit 70), and a focal adjustment unit 80.

For example, the delivery unit 41 may optically guide a laser beam to the patient's eye E. For example, the delivery unit 41 may include the irradiation end unit 42 and at least a portion of the irradiation optical system 320.

For example, the movement units (for example, the first movement unit and the second movement unit 200, refer to FIG. 4) may include the drive sections (for example, the first drive section and the second drive section 226). The movement unit may move the irradiation end unit 42 including the objective lens 305 toward the patient's eye E by driving the drive section.

For example, the observation optical system (for example, the observation/image capturing unit 70, refer to FIG. 3) is provided in order to observe the anterior chamber of the patient's eye E. For example, the observation optical system may be provided in the irradiation end unit 42. The observation optical system may allow the anterior chamber to be observed through the objective lens 305 of the irradiation optical system 320. The observation optical system may allow an observation through a different objective lens.

For example, the focal adjustment unit 80 (refer to FIGS. 3 and 10) may adjust focus of the observation optical system with respect to the anterior chamber in accordance with a distance of the irradiation end unit 42 to the patient's eye E generated by the movement unit. For example, focus of the observation optical system may be adjusted to a focusing position where an image of the anterior chamber of the patient's eye E focuses. For example, the focal adjustment unit 80 may adjust focus based on information of the projected patient's eye E in an observation image or a luminescent spot of the cornea.

As focus of the observation optical system is adjusted, it is possible to acquire an observation image which is in focus from a standby position to an irradiation position so that it is easy to see a state of the patient's eye E. Since the observation image is in focus when positioning the eyeball fixing unit 280 in the patient's eye E, positioning can be more accurately performed. The focal adjustment unit 80 may cause the observation image to focus on the patient's eye E even after the eyeball is fixed by the eyeball fixing unit 280. Accordingly, it is easy to observe deviation of the patient's eye until positioning of the interface unit 50 is completed. For example, it is easy to determine a state of the patient's eye E based on the observation image when a fixation state of the patient's eye E is misaligned or when the patient's eye E is deviated from the eyeball fixing unit 280.

For example, the movement unit may move the irradiation end unit 42 between a first position (for example, the irradiation position) and a second position (for example, the standby position). For example, the first position is a position where the irradiation end unit 42 is arranged when irradiating the patient's eye E with a laser. For example, the second position is a position away from the patient's eye E further than the first position and is a position where the irradiation end unit 42 is arranged before the patient's eye E is fixed by the eyeball fixing unit 280.

For example, the focal adjustment unit 80 may individually adjust focus of the observation optical system with respect to the anterior chamber in accordance with a distance of the irradiation end unit 42 to the patient's eye E at the first position and the second position. Accordingly, focus of the observation optical system can be adjusted with respect to the anterior chamber of the patient's eye E even at the standby position of the eyeball fixing unit 280 before the patient's eye E is fixed.

Figure 10A:
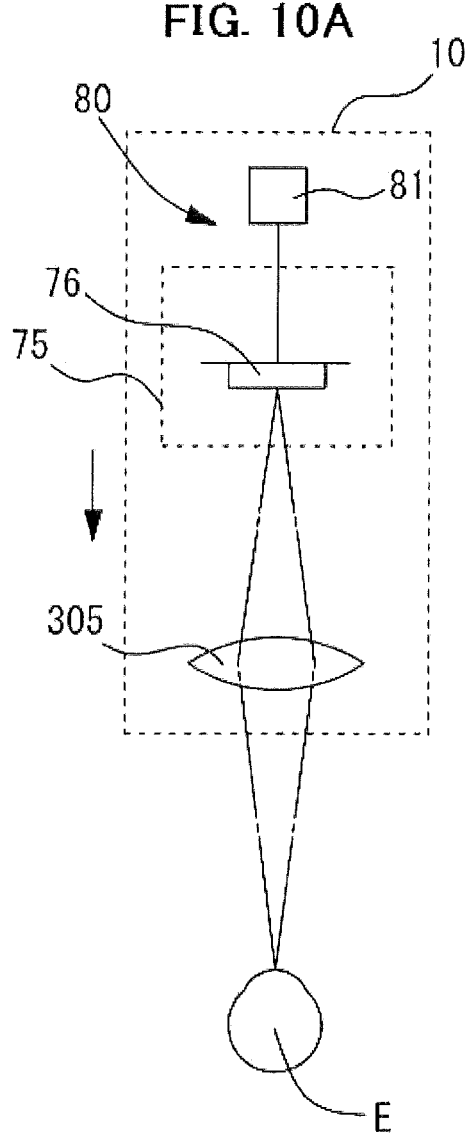
FIGS. 10A and 10B are diagrams for illustrating an operation of a focal adjustment unit.
Figure 10B:
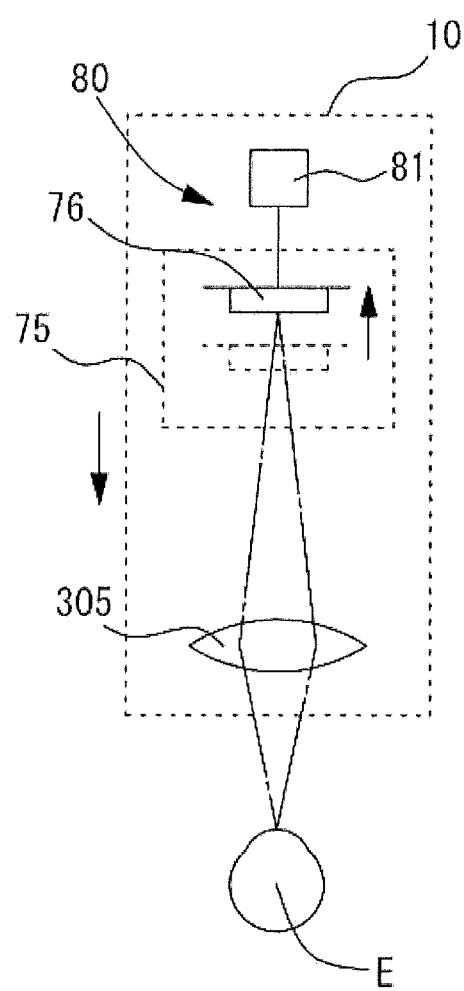

For example, the focal adjustment unit 80 may include the drive section 81 and a control section (for example, the control unit 100) (refer to FIGS. 10A and 10B). For example, the drive section 81 is arranged in the observation optical system in order to adjust focus of the observation optical system, thereby adjusting focus of the observation optical system. For example, the control section may adjust focus of the observation optical system with respect to the anterior chamber by controlling the drive section 81. For example, the drive section 81 for adjusting focus may cause a member (for example, a lens or a light receiving element 76) arranged in the observation optical system to move in the optical axis direction. For example, the drive section may allow insertion/withdrawal of the member.

For example, the apparatus 1 may include a detection unit (for example, the encoder 203, an OCT unit 71, and a front surface observation unit 75). For example, the detection unit detects the distance of the irradiation end unit 42 to the patient's eye E generated by the movement unit. In this case, the control section may control the drive section in accordance with a detection result of the detection unit, thereby adjusting focus of the observation optical system with respect to the anterior chamber in accordance with the distance of the irradiation end unit 42 to the patient's eye E generated by the movement unit.

The detection unit may detect the distance of the irradiation end unit 42 to the patient's eye E by using the position detection sensor such as the encoder or may indirectly detect the distance of the irradiation end unit 42 to the patient's eye E by detecting a distance of the observation optical system to the patient's eye E based on the observation image in the observation optical system.

The control section may adjust focus of the observation optical system in response to the distance of the irradiation end unit 42 to the patient's eye E or may switch a focal position of the observation optical system to a predetermined focal position in accordance with a switch operation.

The surgical operation apparatus 1 may include an alignment detection unit. For example, in a state where the irradiation end unit 42 is arranged at the second position, the alignment detection unit may detect an alignment state of the irradiation end unit 42 with respect to the patient's eye E based on a light receiving signal from the light receiving element 76 arranged in the observation optical system. Accordingly, the alignment state of the irradiation end unit 42 with respect to the patient's eye E can be detected at an early stage. In other words, when the patient's eye E is fixed by the eyeball fixing unit 280, positioning of the eyeball fixing unit 280 in the patient's eye E is easily performed.

A light source 60 which performs irradiation with illumination light for forming a luminescent spot on the cornea of the patient's eye E may be arranged in the irradiation end unit 42 (refer to FIGS. 3 and 4). For example, the observation optical system may capture an image of the anterior chamber of the patient's eye E including at least any one of a first cornea reflection image and a second cornea reflection image. For example, the first cornea reflection image is formed by illumination light passing through the outside of an interface having a light-transmitting optical member covering at least a portion of the cornea of the patient's eye. For example, the second cornea reflection image is formed by illumination light passing through the inside of the interface. The alignment detection unit may detect a position of the patient's eye E based on at least any one of the first cornea reflection image and the second cornea reflection image captured by the observation optical system.

Example

Figure 1:
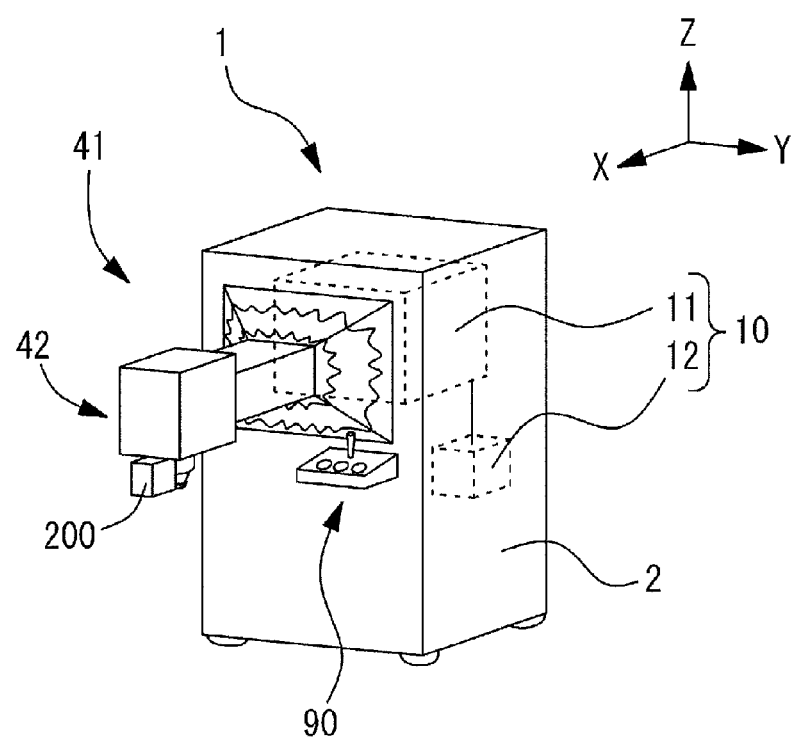
FIG. 1 is a configuration diagram of an appearance of an ophthalmic laser surgery apparatus of the present example.

Hereinafter, an example of the present disclosure will be described with reference to the drawings. In the following descriptions, as an example, a direction along the optical axis in which the patient's eye E is irradiated with the laser beam is referred to as a Z-direction. One of directions intersecting (vertically intersecting, in the present embodiment) the Z-direction is referred to as an X-direction. A direction intersecting (vertically intersecting, in the present embodiment) both the Z-direction and the X-direction is referred to as a Y-direction. The X-direction, the Y-direction, and the Z-direction may be appropriately set. For example, when the directions are defined based on up, down, left, and right of a patient, the X-direction may be referred to as a lateral direction of the patient and the Y-direction may be referred to as a vertical direction of the patient. Otherwise, the X-direction may be referred to as the vertical direction of the patient, the Y-direction may be referred to as the lateral direction of the patient, and the Z-direction may be referred to as an axial direction of the eye E. FIG. 1 is a schematic diagram showing an appearance of the apparatus 1. FIG. 3 is a schematic diagram showing a schematic configuration of an optical system and a control system of the apparatus 1.

<Overall Configuration>

The ophthalmic laser surgery apparatus 1 of the present example is used in order to treat tissues of the patient's eye E. In the present example, the ophthalmic laser surgery apparatus 1 capable of treating the crystalline lens of the patient's eye E is exemplified. However, for example, the technology exemplified in the present example may be applied when treating other sites (for example, the cornea and the fundus) of the patient's eye E. Naturally, the present technology may be applied when treating tissues of the anterior chamber including the cornea and the crystalline lens.

For example, the ophthalmic laser surgery apparatus (hereinafter, referred to as the surgical operation apparatus) 1 of the present example mainly includes the first movement unit 10, the second movement unit 200, a laser irradiation unit 300, the interface unit 50, and the control unit 100. An illumination light source 60, the observation/image capturing unit 70, the focal adjustment unit 80, and an operation unit 90 may be arranged in the surgical operation apparatus 1.

The laser irradiation unit 300 includes a laser source unit 310, and a laser irradiation optical system (laser delivery) 320. The laser source unit 310 is arranged inside the main body portion 2. The laser irradiation optical system (an optical guide system) 320 is an optical system for optically guiding a laser beam from the laser source unit 310 to the eye E.

At least a portion of the laser irradiation optical system 320 is provided in the delivery unit 41. A laser emitted from the laser source unit 310 is optically guided to the irradiation end unit 42 in the delivery unit 41 through the laser irradiation optical system 320 (details thereof will be described later). At least an objective optical system (for example, the objective lens 305) for concentrating a laser beam is arranged in the irradiation end unit 42, and the eye E is irradiated from an emission end of the irradiation end unit 42 with a laser. The observation/image capturing unit 70 may be arranged in the irradiation end unit 42 of the delivery unit 41, thereby being utilized so as to perform an observation, image-capturing, and the like of the eye E.

The first movement unit 10 is arranged to cause the irradiation end unit 42 to perform an XYZ-movement with respect to the main body portion 2. The interface unit 50 is provided in the emission end of the irradiation end unit 42. Moreover, the eyeball fixing unit 280 is arranged in the delivery unit 41 through the second movement unit 200. Therefore, when the irradiation end unit 42 is moved by the first movement unit 10, as a result, the interface unit 50, the eyeball fixing unit 280, and the second movement unit 200 integrally move together with the irradiation end unit 42.

For example, the first movement unit 10 is provided in the delivery unit 41, and the irradiation end unit 42 is moved with respect to the main body portion 2 (for example, refer to JP-A-2000-152954 regarding the movement mechanism thereof). However, there is no limitation. For example, the first movement unit 10 may be provided in the main body portion 2. The first movement unit 10 may move the irradiation end unit 42 relatively to the main body portion 2 by moving the delivery unit 41 with respect to the main body portion 2.

The second movement unit 200 is arranged so as to relatively moving the eyeball fixing unit 280 with respect to the irradiation end unit 42. For example, when the irradiation end unit 42 is moved by the first movement unit 10 described above, the second movement unit 200 is used so as to decrease displacement of the eyeball fixing unit 280 to the patient's eye side. In other words, regardless of the presence/absence of the eye E, the eyeball fixing unit 280 is moved by the first movement unit 10. However, the eyeball fixing unit 280 is individually movable in a direction opposite to a movement direction of the irradiation end unit 42 by the second movement unit 200 (details thereof will be described later, refer to FIGS. 4, 9A and 9B).

Figure 2:
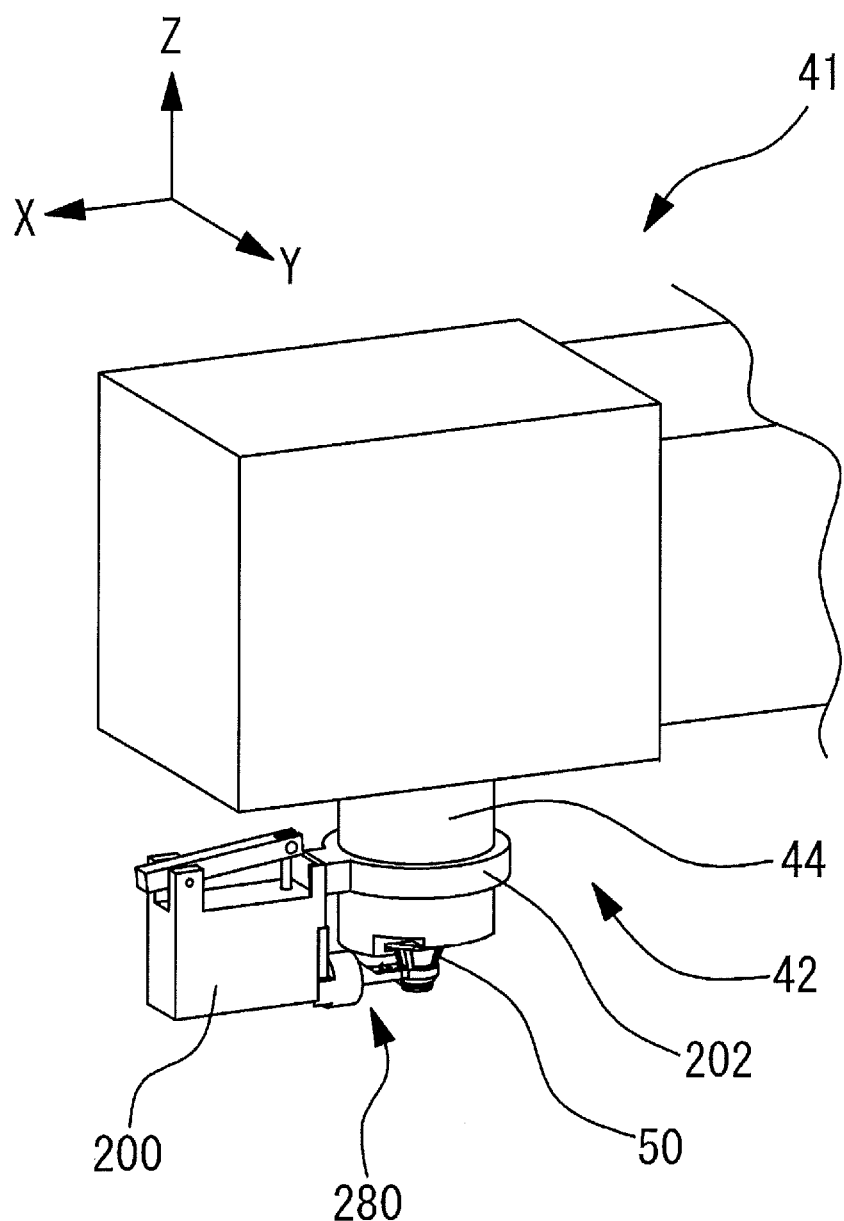
FIG. 2 is an enlarged perspective view of an irradiation end unit.

In FIGS. 2 and 4, the second movement unit 200 is provided in the irradiation end unit 42 in the delivery unit 41 but is not limited thereto. For example, the second movement unit 200 may be provided in a base portion of the delivery unit 41.

In more details, the below-described eyeball fixing unit 280 can be detachably attached to the second movement unit 200. The second movement unit 200 allows the eyeball fixing unit 280 to move in the Z-direction. The eyeball fixing unit 280 fixedly holds the eyeball of the patient's eye E with respect to the laser irradiation unit 300. The laser irradiation unit 300 irradiates the patient's eye E with a laser beam. The irradiation end unit 42 is provided with the objective lens 305 and the like for concentrating a laser beam on the patient's eye E.

The interface unit 50 approaches the cornea of the patient's eye E, lessens a difference of a refractive index, and decreases an aberration of a laser beam generated due to the difference of the refractive index. Accordingly, for example, surface reflection of the cornea and the lens decreases. The illumination light source 60 illuminates the patient's eye E. The observation/image capturing unit 70 captures a frontal image of the anterior chamber of the patient's eye E and a tomographic image of the anterior chamber. For example, the observation/image capturing unit 70 includes an optical interference tomographic image capturing unit (abbreviated to OCT (optical coherence tomography) unit) 71 and the front surface observation unit 75. The optical interference tomographic image capturing unit 71 captures (acquires) the tomographic image of the patient's eye E. The front surface observation unit 75 captures an image of the anterior chamber of the patient's eye E. The focal adjustment unit 80 adjusts focus of the front surface observation unit 75. The operation unit 90 is provided in order to operate the apparatus 1. The control unit 100 performs an integrated control of the apparatus in its entirety. The control unit 100 may drive the second movement unit 200 based on a control signal from the operation unit 90.

<First Movement Unit>

In more details, the first movement unit 10 (refer to FIG. 1) integrally moves the irradiation end unit 42, the second movement unit 200, the eyeball fixing unit 280, the interface unit 50, the observation/image capturing unit 70, and the like. Accordingly, the irradiation end unit 42, the eyeball fixing unit 280, and the interface unit 50 can be aligned with the patient's eye E.

For example, the first movement unit 10 includes a movement mechanism 11 and the drive section (a motor, an actuator, and the like) 12. The movement mechanism 11 moves a portion of a main body such as the eyeball fixing unit 280 and the interface unit 50 with respect to the main body portion 2. The drive section 12 drives the movement mechanism 11. The first movement unit 10 moves the irradiation end unit 42 (an optical axis L1 thereof), the eyeball fixing unit 280, and the interface unit 50 (a central axis thereof) shown in FIG. 4, with respect to the main body portion 2 and the patient's eye E in a three-dimensional direction. Here, the optical axis L1 coincides with the central axis of the eyeball fixing unit 280 and the interface unit 50. Moreover, the central axis of the below-described suctioning ring 281 coincides with the central axis of the interface unit 50.

Regarding the movement mechanism 11 and the drive section 12, the movement mechanism and the drive section for moving the irradiation end unit 42 may be respectively arranged at positions different from each other in the X-direction, the Y-direction, and the Z-direction. For example, the movement mechanism and the drive section related to the X-direction and the Y-direction may be provided in the main body portion 2, and the movement mechanism and the drive section related to the Z-direction may be provided in the base portion of the delivery unit 41.

The first movement unit 10 is connected to the control unit 100 and moves the irradiation end unit 42, the eyeball fixing unit 280, and the interface unit 50 with respect to the main body portion 2 based on an operational signal of the operation unit 90. A practitioner, while checking the patient's eye E displayed on a display portion 92, performs positional alignment in the XY-direction (XY-alignment) and positional alignment in the Z-direction (Z-alignment). Here, at least the irradiation end unit 42, the eyeball fixing unit 280, and the interface unit 50 integrally move. The first movement unit 10 moves the suctioning ring 281 and the interface unit 50 along a Z-axis direction. The first movement unit 10 includes a sensor such as the encoder and the like inside thereof. Therefore, positions of the eyeball fixing unit 280, the interface unit 50, and the like are acquired by the control unit 100.

It is acceptable as long as the first movement unit 10 has a configuration to move at least in the Z-axis direction. For example, the first movement unit 10 may have a configuration in which the laser irradiation unit 300, and the interface unit 50 are attached to another apparatus (which is connected to the laser irradiation unit 300) such as a surgical operation microscope. The first movement unit 10 may be configured to be held by a practitioner so as to move for the XY-alignment.

<Laser Irradiation Unit>

As shown in FIG. 3, for example, the laser irradiation unit 300 may include the laser source unit 310, the laser irradiation optical system (laser delivery) 320, and the position detection unit 370. The laser source unit 310 emits a laser beam for surgical operation. The laser irradiation optical system 320 includes an optical member for optically guiding a laser beam. The laser irradiation optical system 320 is built in the main body portion 2 and the delivery unit 41. For example, the laser irradiation optical system 320 includes a scanning unit 330, the objective lens 305, and various optical members. The objective lens 305 is provided on an optical path between the scanning unit 330 and the patient's eye E. The objective lens 305 concentrates a laser beam passing through the scanning unit 330 on a tissue of the patient's eye E. The position detection unit 370 detects the absolute position of the patient's eye E.

A laser beam emitted from the laser source unit 310 is used in order to induce plasma in a tissue through a nonlinear interaction. The nonlinear interaction denotes one of interactions generated by light and a substance and is an action in which a response non-proportional to intensity of light (that is, density of a photon) occurs. The ophthalmic laser surgery apparatus 1 of the present embodiment concentrates (focuses) a laser beam inside a transparent tissue of the patient's eye E, thereby generates multiphoton absorption at a concentration position (also referred to as "a laser spot") or on a upstream side of the optical path (a luminous flux) slightly from the concentration position. A probability of generating multiphoton absorption is not proportional to intensity of light, thereby being nonlinear. When an excitation state is formed due to multiphoton absorption, a plasma bubble is generated inside a tissue, thereby cutting and crushing the tissue. The aforementioned phenomenon is also referred to as photodistruction (photodisruption). In photodisruption caused by a nonlinear interaction, an influence of heat caused by a laser beam is unlikely to be applied to surroundings of the concentration position, thereby allowing microscopic treatment. As the pulse width of a laser beam decreases, photodisruption efficiently occurs by less energy.

As the laser source unit 310, a device emitting a laser beam having the pulse width of 1 femtosecond to 10 nanoseconds is used. For example, as the laser source, a device emitting a laser beam of an infrared region having the pulse width of 500 femtoseconds and the center wavelength of 1,040 nm (the wavelength width is ±10 nm) may be used. As the laser source, a laser source emitting laser of an ultraviolet width, having the pulse width of 10 picoseconds, and having the center wavelength of 450 nm at the wavelength width of ±10 nm may be used. Moreover, the laser source unit 310 uses a laser source which has the spot size of the laser spot is 1 μm to 15 μm and can emit an output laser beam generating a breakdown.

In the laser irradiation optical system 320, the laser source unit 310 is referred to as the upstream, and the patient's eye E is referred to as the downstream. Then, a mirror 301, a mirror 302, a hole mirror 371 to a lens 303, a lens 304, and a beam combiner 72 are arranged along the optical axis L1 from the laser source unit 310 toward the downstream.

The mirrors 301 and 302 adjust the optical axis of a laser beam. The hole mirror 371 is used as a beam splitter splitting the optical axis of the laser beam L1 and an optical axis L2 of the position detection unit 370. The lens 303 is used in order to form an intermediate image of a laser beam of the scanning unit 330. The lens 304 forms a pupil conjugation position. The beam combiner 72 multiplexes the optical axis L1 and an optical axis L3 of the observation/image capturing unit 70.

The mirrors 301 and 302 are configured to cause reflection surfaces to be orthogonal to each other and are held by tiltable holding members. The optical axis of a laser beam emitted from a laser source unit 110 can be adjusted by moving and tilting the reflection surfaces of the mirrors 301 and 302. As the mirrors 301 and 302 are adjusted the axis of a laser beam is aligned with the optical axis L1.

<Scanning Unit>

The scanning unit 330 performs scanning with a laser beam, thereby scanning the concentration position of the laser beam concentrated by the objective lens 305 (details thereof will be described later). In other words, the scanning unit 330 moves the concentration position of the laser beam to a target position. The scanning unit 330 of the present embodiment includes a Z-scanning portion 350 and an XY-scanning portion 360.

The Z-scanning portion 350 of the present embodiment includes a concave lens 351, a convex lens 352, and a drive section 353. The drive section 353 moves the concave lens 351 along the optical axis L1. As the concave lens 351 moves, an emanation state of a beam passing through the concave lens 351 varies. As a result, the concentration position (the laser spot) of the laser beam moves in the Z-axis direction.

The XY-scanning portion 360 of the present embodiment includes an X-scanner 361, a Y-scanner 364, and lenses 367 and 368. The X-scanner 361 performs scanning with a laser beam in the X-direction by causing a drive section 362 to oscillate a galvano mirror 363. The Y-scanner 364 performs scanning with a laser beam in the Y-direction by causing a drive section 365 to oscillate a galvano mirror 366. The lenses 367 and 368 conjugate two galvano mirrors 363 and 366.

It is acceptable as long as the scanning unit 330 has a configuration in which scanning can be performed with a laser beam in the XY-direction. For example, a configuration may be adopted to perform scanning in the X-direction through a polygon mirror and to perform scanning in the Y-direction through the galvano mirror. Moreover, a configuration may be adopted to cause resonant mirrors to correspond to the X-direction and the Y-direction. In addition, two prisms may be configured to independently rotate. In this manner, the scanning unit 330 moves the laser spot three-dimensionally (an XYZ-direction) inside an ocular tissue (inside the target) of the patient's eye E.

A beam combiner (the beam splitter) 72 for causing an optical axis of a laser beam axis and an optical axis for observation-image capturing to be coaxial is arranged between the scanning unit 330 and the objective lens 305. The beam combiner 72 has characteristics reflecting a laser beam and transmitting illumination light of an observation/image capturing unit. The objective lens 305 is a lens fixedly arranged with respect to the irradiation end unit 42. As shown in FIG. 4, the objective lens 305 is held by the irradiation end unit 42. The objective lens 305 performs image-forming with a laser beam on a target as the laser spot. For example, the spot size of the laser spot is approximately 1 µm to 15 µm.

The laser irradiation unit 300 is provided with an aiming light source (not illustrated) emitting aiming light with which a practitioner checks a laser irradiation position.

<Position Detection Unit>

The position detection unit 370 is used in order to detect the position of the patient's eye E with respect to the scanning unit 330. As the position of the patient's eye E with respect to the scanning unit 330 is detected, the ophthalmic laser surgery apparatus 1 of the present embodiment causes the concentration position on which a laser beam is concentrated to be associated with the tomographic image (details thereof will be described later). As the concentration position is associated with the tomographic image, control data for controlling the scanning unit 330 and the like can be set by using the tomographic image. Refer to JP-A-2013-248304 for details of the position detection unit 370, for example.

<Irradiation End Unit>

For example, the irradiation end unit 42 (refer to FIGS. 2 and 4) integrally holds the objective lens 305, the interface unit 50, and the illumination light source 60. For example, the irradiation end unit 42 includes the lens barrel 44. The lens barrel 44 is tubular and holds the objective lens 305 and the like therein. The illumination light source 60 is fixed to an end portion of the lens barrel 44 on the patient's eye E side. Moreover, a guide 46 is formed at the end portion of the lens barrel 44 on the patient's eye E side. The interface unit 50 is detachably attached to the guide 46.

The irradiation end unit 42 is moved in the XYZ-axis direction with respect to the main body portion 2 by the first movement unit 10. The objective lens 305, the interface unit 50, the illumination light source 60, and the like which are held by the irradiation end unit 42 are moved by the first movement unit 10 together with the irradiation end unit 42.

<Interface Unit>

The interface unit 50 (refer to FIG. 4) approaches the cornea of the patient's eye E, weakens refractive power of the cornea, and performs a role of causing a laser beam to easily reaches (be concentrated) the ocular tissue such as the crystalline lens. The interface unit 50 of the present embodiment is configured to cover at least a portion of the cornea without being in contact with the cornea. The interface unit 50 mainly includes the cover glass 51 and a holder 52. For example, the cover glass 51 is an optical member covering the cornea. For example, the holder 52 holds the cover glass 51. The interface unit 50 is detachably attached to the lens barrel 44 of the irradiation end unit 42 through the holder 52.

The cover glass 51 is a member covering the cornea and has a size covering at least NA where the laser spot is concentrated. The cover glass 51 is a light-transmitting transparent member, and is formed of glass and a resin, for example. The cover glass 51 is positioned at a liquid level of liquid described below and performs a role of covering the liquid. The holder 52 is a tapered member which is conically formed and supports the cover glass 51 at the tip end point of the cone. Moreover, a fitting portion allowing mutual fitting is formed in an upper portion of the holder 52 so as to be detachably attached to the lens barrel 44 of the irradiation end unit 42. For example, in the present example, a slider 53 is formed in an upper portion of the holder 52. Then, the interface unit 50 is detachably attached by sliding the slider 53 with respect to the guide 46 formed in the irradiation end unit 42.

The interface unit 50 has a shape so as to be accommodated inside the below-described suctioning ring 281. Each member of the interface unit 50 is formed with an element having biocompatibility. The interface unit 50 is a disposable type which is discarded after being used once.

The interface unit 50 approaches the cornea of the patient's eye E adsorbed to the below-described suctioning ring 281. Moreover, the suctioning ring 281 may be adsorbed after positions of the patient's eye E and the interface unit 50 are determined. For example, the inside of the suctioning ring 281 is filled with liquid (a physiological saline solution). Refractive power of the cornea is cancelled due to the cover glass 51 and the liquid. Accordingly, a laser beam is suppressed from refracting from the objective lens 305 to the crystalline lens which is a target.

The interface unit 50 may be configured to be in direct contact with the cornea. For example, the interface unit 50 may be a unit which applanates the cornea by bringing the cover glass 51 into contact with the cornea. As a result, as the cornea comes into contact with the cover glass 51, the cornea is positioned with respect to the laser irradiation optical system 320. For example, it is acceptable as long as the cover glass 51 has a contact surface which covers the cornea so as to cover a laser irradiation region inside the cornea and the like.

<Illumination Light Source>

The illumination light source 60 (refer to FIGS. 3 and 4) illuminates the patient's eye E. For example, the illumination light source 60 is provided with a light source for forming the luminescent spot in the patient's eye E and a light source for increasing contrast of the pupil. In the present example, for example, an infrared light source is used as the light source forming the luminescent spot. Accordingly, it is possible to decrease dazzling feeling of a patient. For example, a visible light source is used as the light source for increasing contrast of the pupil. In more details, as the visible light source, for example, a green or red light source may be used.

One light source which is used both as the light source for forming the luminescent spot and the light source for increasing contrast of the pupil may be used as the illumination light source 60.

The luminescent spot, that is, a cornea reflection image is formed in the patient's eye E by the illumination light source 60. The luminescent spot is observed by the below-described front surface observation unit 75 and the like. For example, the below-described control unit 100 may detect the position of the patient's eye E from the position of the luminescent spot.

<Second Movement Unit>

As shown in FIG. 4, for example, the second movement unit 200 may hold the eyeball fixing unit 280 so as to be drivable in the Z-axis direction with respect to the objective lens 305. For example, the second movement unit 200 may include the base portion 201, the arm 202, a link unit 210, the encoder 203, a link drive unit 220, the lock portion 230, a position sensor 240, the load cell 206, and the connection portion 250.

The base portion 201 holds each configuration of the second movement unit 200. The arm 202 connects the base portion 201 to the lens barrel 44 of the irradiation end unit 42 (refer to FIG. 4). As described above, the irradiation end unit 42 is moved in the XYZ-direction by the first movement unit. The second movement unit connected to the lens barrel 44 is also moved in the XYZ-direction. The arm 202 may be rotatably attached to the lens barrel 44 in a horizontal direction. For example, a position of the second movement unit 200 with respect to the lens barrel 44 may vary. For example, the second movement unit 200 may be turnably provided in the XY-direction about the lens barrel 44. For example, the position of the second movement unit 200 may be switched between a case of treating the right eye of a patient and a case of treating the left eye. Accordingly, the second movement unit may be prevented from coming into contact with the patient. The second movement unit 200 may be detachably attached to the lens barrel 44.

<Link Unit>

The link unit 210 forms a movement mechanism for moving the eyeball fixing unit 280 in the Z-axis direction. For example, the link unit 210 includes a link 211, a link 212, a joint 213, and a joint 214. The link 211 has a rectangular shape. The link 212 has a rod shape. The link 211 and the link 212 form a link mechanism. One end portion of the link 211 is rotatably connected to the base portion 201 by the joint 213. The other end portion of the link 211 is connected to an end portion of the link 212 by the joint 214.

The link 212 is inserted into a tubular guide 215. A movement direction of the link 212 is defined to be in the Z-axis direction by the guide 215.

In the second movement unit, a mechanism for moving the eyeball fixing unit 280 in the Z-axis direction does not have to be the above-described link mechanism. For example, the eyeball fixing unit 280 may be moved in the Z-axis direction by a rack and pinion mechanism.

A support base 216 is fixed to the link 212. The support base 216 is moved in the Z-axis direction together with the link 212. The load cell 206 has a rectangular shape and detects a load added from both ends thereof. One end portion of the load cell 206 is fixed to the support base 216. The other end portion of the load cell 206 is fixed to the connection portion 250. In other words, the load cell 206 detects a load added between the support base 216 and the connection portion 250.

Figure 5:
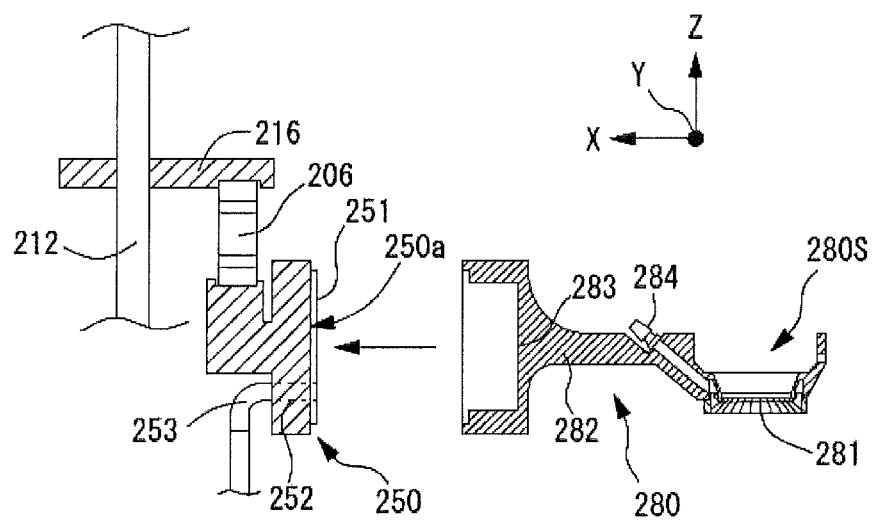
FIG. 5 is a diagram for illustrating attachment/detachment of an eyeball fixing unit.

The connection portion 250 adsorbs and holds the eyeball fixing unit 280 so as to be detachably attached (refer to FIG. 5). For example, the connection portion 250 includes a seal member 251, the suctioning hole 252, and a connecting pipe 253. The seal member 251 enhances airtight properties of the connection portion 250 and the eyeball fixing unit 280 when adsorbing the eyeball fixing unit 280. An elastic body is mostly used as the seal member 251. The suctioning hole 252 is open on a connection surface 250a of the connection portion 250. The connecting pipe 253 is caused to fit the suctioning hole 252. A hose (not illustrated) extending from a suctioning device is connected to the connecting pipe 253. The suctioning device performs suctioning of air in a space R formed between the connection surface 250a and the concave portion 283. As suctioning of air is performed, a negative pressure is generated in the space R. The connection portion 250 and the eyeball fixing unit 280 pull each other due to the negative pressure, thereby being adsorbed as a result.

If a significant load is added to the eyeball fixing unit 280, a malfunction of the load cell 206 may occur due to the transmitted load. In the control unit 100, a suctioning pressure of the suctioning device may be set so as to allow the eyeball fixing unit 280 to be detached from the connection portion 250 when a significant load is added to the eyeball fixing unit 280.

For example, when a load exceeding a predetermined value is added to the eyeball fixing unit 280, the eyeball fixing unit 280 is detached from the connection portion 250. Accordingly, it is possible to decrease a significant load to the load cell 206, and thus, a malfunction of the load cell 206 decreases.

The connection portion 250 fixes the eyeball fixing unit 280 by a suctioning pressure. However, any type of a fixing method may be adopted. For example, the connection portion 250 and the eyeball fixing unit 280 may be fixed to each other by screwing screws respectively formed. The connection portion 250 and the eyeball fixing unit 280 may be fixed to each other by a magnetic force. The connection portion 250 and the eyeball fixing unit 280 may be fixed to each other by fitting together. The connection portion 250 and the eyeball fixing unit 280 may be fixed to each other by using an adhesive substance.

<Link Drive Unit>

For example, the link drive unit 220 includes a pin 221, a spring 222, a feed screw 223, a nut 224, a holder 225, and a drive section (an actuator) 226. The feed screw 223 is connected to a rotational shaft 226a of the drive section 226. As the drive section 226 rotates, the feed screw 223 rotates.

As the feed screw 223 rotates, the nut 224 screwed to the feed screw 223 vertically moves.

The holder 225 is fixed onto an upper portion of the nut. The pin 221 is attached to the holder 225 through the spring 222. As the nut rises, the pin 221 simultaneously rises. As the pin 221 rises, the pin 221 comes into contact with the link 211. As the pin 221 continues to rise, the link 211 is pushed up by the pin 221 which is applied with an elastic force of the spring 222, thereby rotating having the joint 213 as a cardinal point. As the link 211 rotates, the link 212 vertically moves together with the joint 214. The link 212 moves in the Z-axis direction along the guide 215.

The load cell 206 is fixed to the link 212. Moreover, the connection portion 250 is fixed to the link 212 through the load cell 206. The load cell 206 and the connection portion 250 are moved in the Z-axis direction together with the link 212. The below-described eyeball fixing unit 280 is adsorbed to the connection portion 250. Accordingly, the eyeball fixing unit 280 moves in the Z-axis direction together with the link 212.

<Encoder>

The encoder 203 detects a movement amount or a position of the link 212. Magnetized lines are formed at multiple places in the link 212 of the present example. The encoder 203 detects magnetism of the line so as to detect a movement amount or a position of the link 212 based on the number of the passed lines. As the encoder 203, without being limited to magnetism, various types of encoders (or potentionmeters) which can detect a movement amount or a position of the member may be used.

<Position Detection Sensor>

The position detection sensor 240 detects a drive limit of the link 212. For example, a shielding plate is fixed to the link 212. For example, the position detection sensor 240 includes U-shaped terminals. For example, magnetism is constantly generated between the U-shaped terminals. If the shielding plate is inserted between the terminals, the terminals are shielded from magnetism. Then, the position detection sensor 240 detects that magnetism is shielded, thereby detecting that the link 212 is in a predetermined region. For example, the present example may include a sensor 241 for detecting that the link 212 is at the upper limit of a drive region, and a sensor 242 for detecting that the link 212 is positioned at the lower limit.

The position detection sensor may be a sensor adopting another principle, without being limited to the magnetism sensor. For example, an optical sensor such as a photo interrupter may be adopted.

<Lock Portion>

For example, the lock portion 230 regulates a movement of the link 212. The lock portion 230 is provided on a side opposite to the joint 214 side of the link 212. For example, the lock portion 230 includes a casing 231, a lock member 232, a spring 233, and a drive section 234. The lock member is rotatably provided in the casing 231. For example, the lock member 232 has an annular shape. A hole 232a is formed in the lock member 232. The link 212 passes through the hole 232a. The lock member 232 is rotatably provided in the casing 231. The lock member 232 is biased so as to rotate in a uniform direction by the spring 233. The lock member 232 rotates by the spring 233, and the hole 232a comes into contact with the link 212. As the hole 232a of the lock member 232 comes into contact with the link 212, the link 212 is fixed. The drive section 234 rotates the lock member 232 in a direction opposite to a rotational direction by an elastic force of the spring 233. The drive section 234 rotates the lock member 232 until the lock member 232 maintains a horizontal level.

For example, the lock portion 230 is in a state where the lock member 232 rotates by an elastic force of the spring 233, and the link 212 is locked at all times. For example, when the link unit 210 is moved by the drive section 226, the below-described control unit 100 simultaneously drives the drive section 234 and rotates the lock member 232 until the lock member 232 is in the horizontal direction. Then, the link 212 is unlocked, thereby being movable in the Z-axis direction.

When the drive section 234 is stopped, locking is in operation by the lock portion 230. Accordingly, the drive section 234 is suppressed from resulting in inconvenience and the like caused by release of locking when the drive section 234 is stopped.

It is acceptable as long as the lock portion 230 can regulate a movement of the link 212, without being limited to the above-described configuration. For example, a solenoid, an electro-magnetic brake, or the like may be used. As described above, the lock portion 230 may electrically control a movement of the link 212.

<Eyeball Fixing Unit>

The eyeball fixing unit 280 (refer to FIGS. 4 and 5) is a unit for fixing the patient's eye E with respect to the objective lens 305. A laser can be preferably concentrated on the patient's eye E by fixing the patient's eye E to the objective lens 305. For example, the eyeball fixing unit 280 includes the suctioning ring 281, the support portion 282, the concave portion 283, the suctioning pipe 284, and the like. The suctioning ring 281 is a contact portion coming into contact with the patient's eye E (for example, the sclera). The support portion 282 supports the suctioning ring 281. The concave portion 283 is connected to the connection portion 250 of the second movement unit 200. The suctioning pipe 284 is a flow path (an air hole) for adding a suctioning pressure to the suctioning ring 281. The eyeball fixing unit 280 transmits (adds) a suctioning pressure added from a suctioning pump (not illustrated) to the suctioning ring 281 through the suctioning pipe 284.

The suctioning ring 281 has opening along a curved surface of the sclera. The opening of the suctioning ring 281 is formed to surround a limbal ring portion of the eyeball (a peripheral portion of the cornea) and has a ring shape caused to fit the eyeball fixing unit 280. Accordingly, the eyeball is uniformly adsorbed to the suctioning ring 281. The support portion 282 has a wall shape surrounding the suctioning ring 281 (the eyeball) so as to be able to fill the inside of the support portion 282 with liquid while being in a state where the eyeball is adsorbed to the suctioning ring 281.

A space 280S for accommodating the interface unit 50 is formed in the eyeball fixing unit 280 in a noncontact (noninterference) manner. For example, the space 280S may be formed inside the support portion 282. The support portion 282 has a shape which is detachably attached to the connection portion 250 (shape to fit). A suctioning tube from the suctioning pump provided with the apparatus main body (otherwise, another unit) is connected to a pipe 284. Due to a suctioning pressure generated by operating the suctioning pump, the insides of the suctioning tube, the pipe 284, and the suctioning ring 281 are under a negative pressure, and the sclera of the patient's eye E is adsorbed to the opening of the suctioning ring 281.

For example, the eyeball fixing unit 280 of the present example further includes a liquid supply/discharge pipe (not illustrated) (hereinafter, abbreviated to a liquid pipe). The liquid pipe is the flow path (a through hole) formed to penetrate the support portion 282 and may supply and discharge liquid. The liquid pipe may be connected to a perfusion suctioning unit (not illustrated) through a tube and the like. Before performing laser irradiation, liquid is supplied to the inside of the eyeball fixing unit 280 by operating the perfusion suctioning unit. After a surgical operation, liquid inside the eyeball fixing unit 280 is discharged. A configuration may be adopted to only supply liquid through the liquid pipe. A configuration may be adopted to cause the eyeball fixing unit 280 fixed to the patient's eye E to be detached from the patient's eye E so as to discard liquid. Liquid may be injected into the eyeball fixing unit 280 by a practitioner. For example, after completing fixation of the patient's eye E by using the eyeball fixing unit 280, the practitioner may inject liquid into the suctioning ring 281 using an injector or the like.

The eyeball fixing unit 280 is formed with an element having biocompatibility, such as a resin and metal. The eyeball fixing unit 280 is a disposable type similarly to the interface unit 50. Accordingly, it is preferable to configure the eyeball fixing unit 280 to be detachably attached to the second movement unit 200 (refer to FIG. 5).

In this manner, the eyeball fixing unit 280 and the interface unit 50 can be independently movable in the Z-direction. Moreover, in the present embodiment, since the eyeball fixing unit 280 and the interface unit 50 are configured not to move in the XY-direction with respect to the objective lens 305, adsorbing and the like of the patient's eye E is easily performed.

<Observation/Image Capturing Unit>

The observation/image capturing unit 70 (refer to FIG. 3) allows a practitioner to observe the patient's eye E and captures an image of a tissue subjected to treatment. As an example, the observation/image capturing unit 70 of the present embodiment includes the OCT unit 71 and the front surface observation unit 75. The optical axis L3 of the observation/image capturing unit 70 is caused to be coaxial with the optical axis L1 of the laser beam by the beam combiner 72. The optical axis L3 is branched into an optical axis L4 of the OCT unit 71 and an optical axis L5 of the front surface observation unit 75 by the beam combiner 73.

The OCT unit 71 acquires the tomographic image of a tissue of the patient's eye E by using an optical interference technology. The ophthalmic laser surgery apparatus 1 of the present embodiment causes a position on which a laser beam is concentrated to be associated with the tomographic image of the patient's eye E captured before a surgical operation. As a result, the ophthalmic laser surgery apparatus 1 can generate control data for controlling operations (for example, operations of the drive sections 353, 367, and 368) of irradiation of the laser beam, by using the tomographic image. The OCT unit 71 can adopt various configurations. For example, any one of SS-OCT, SD-OCT, and TD-OCT may be employed as the OCT unit 71. Refer to JP-A-2013-248303 and JP-A-2013-248304 regarding a configuration and a form of use of the OCT unit 71, for example.

The front surface observation unit 75 acquires the frontal image of the patient's eye E. For example, the front surface observation unit 75 of the present example includes the light receiving element 76. The front surface observation unit 75 captures an image of the patient's eye E illuminated by visible light or infrared light, thereby displaying the captured image in the display portion 92 (will be described later). The practitioner can observe the patient's eye E from the front by watching the display portion 92.

For example, the front surface observation unit 75 of the present example may be a telecentric optical system. Accordingly, a magnification of an image may be set not to change even though the focusing position of the frontal image captured by the front surface observation unit 75 is changed. For example, in the surgical operation apparatus 1, there is a case of focusing on the cornea of the patient's eye, the crystalline lens, or like depending on the details of a surgical operation. Thus, the telecentric optical system may be used so as not have to adjust a magnification of an image even though the focusing position is changed.

<Focus Adjustment Unit>

The focal adjustment unit 80 (refer to FIG. 3) adjusts focus of the front surface observation unit 75. The focal adjustment unit 80 of the present example adjusts focus of an image of the anterior chamber of the patient's eye E acquired by the front surface observation unit 75.

For example, the focal adjustment unit 80 of the present example includes a drive section 81 for moving the light receiving element 76 (refer to FIGS. 10A to 11B). The drive section 81 moves the light receiving element 76 in a direction of an image capturing optical axis (the optical axis L5). Accordingly, the focal adjustment unit 80 can adjust the focusing position of the light receiving element 76 in a direction of an image capturing optical axis.

For example, a two-dimensional image capturing element is used as the light receiving element 76. Naturally, the configuration of the front surface observation unit 75 is not limited to the two-dimensional image capturing element. For example, the front surface observation unit 75 may be a scanning-type laser image capturing apparatus, an optical interference tomograph meter, and the like.

<Operation Unit>

Figure 6:
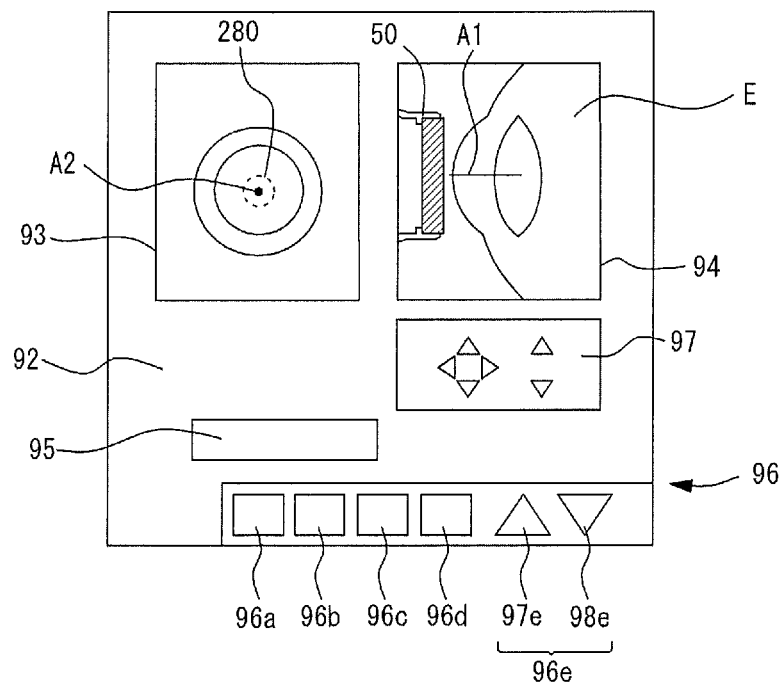
FIG. 6 is a diagram illustrating a display of a monitor.

The operation unit 90 (refer to FIGS. 3 and 6) receives inputs of various operation instructions from a practitioner. As an example, the operation unit 90 of the present embodiment includes an operation portion 91 having various operation buttons such as a trigger switch 91a, the touch panel-type display portion 92, and the like. For example, the trigger switch 91a inputs a trigger signal for emitting a treatment laser beam from the laser irradiation unit 300. For example, the display portion 92 is used as display means for displaying a tomographic image and an anterior chamber image of the patient's eye E, or displaying conditions for surgical operation. As described in the present example, if a touch panel function is provided in the display portion 92, the display portion 92 may be also used as input means for setting the conditions of a surgical operation and setting a surgical operation site (a laser irradiation position) on the tomographic image. It is possible to use a mouse which is a pointing device, a keyboard which is an input device for inputting numerical values and characters, and the like as the input means.

For example, the display portion 92 may display an anterior chamber display portion 93 for displaying the anterior chamber of the patient's eye E, an OCT image display portion 94 for displaying the tomographic image of the anterior chamber of the patient's eye E, a surgical operation condition display portion 95 for displaying surgical operation conditions, an eyeball fixing operation portion (an eyeball fixing/interface operation portion) 96 performing an eyeball fixing operation, and a movement unit operation portion 97 for operation a movement of the irradiation end unit 42.

The OCT image display portion 94 displays a surgical operation site (a laser irradiation range) by a practitioner. A surgical operation site designated in the display portion 92 is transmitted to the control unit 100 as a signal designating a region on an OCT image. In the surgical operation condition display portion 95, a practitioner operates to set an irradiation pattern of a treatment laser beam for crushing (incising) the crystalline lens. A plurality of the irradiation patterns are prepared in advance, thereby being set through selection performed by the practitioner. As the irradiation pattern is set in the surgical operation condition display portion 95, the display portion 92 transmits the set signal to the control unit 100. In the present embodiment, laser outputs, a spot size of the laser spot, and the like are unchangeable and a practitioner does not change the setting. However, a configuration may be adopted to allow the practitioner to perform setting.

The OCT image display portion 94 (the display portion 92) may perform a role of displaying the suctioning ring 281 and the interface unit 50 on an OCT image so that a practitioner can visually and easily perform positional alignment of the eyeball fixing unit 280 and the interface unit 50.

In the present embodiment, the OCT image display portion 94 displays a moving OCT image until at least positioning of the eyeball fixing unit 280 and the interface unit 50 is completed. The cornea and the peripheral portion of the cornea of the patient's eye E (the sclera on the periphery of the limbal ring portion), and the eyeball fixing unit 280 (the suctioning ring 281) are captured and projected in the OCT image. Here, an OCT image captured when the eyeball is fixed includes at least the cornea of the patient's eye E and the suctioning ring 281. An OCT image captured when the cover glass 51 is positioned includes at least the cornea and the cover glass 51.

A suctioning pressure setting section 96a for setting a suctioning pressure added to the suctioning ring 281, a suctioning switch 96b for inputting a command signal to adsorb the eyeball by using the suctioning ring 281, a supply switch 96c for inputting a command signal to supply liquid to the inside of the suctioning ring 281, a discharge switch 96d for inputting a command signal to discharge liquid from the inside of the suctioning ring 281, and a vertical movement switch 96e for adjusting a position (a height position) of the interface unit 50 are arranged in the eyeball fixing operation portion 96.

As the suctioning pressure setting section 96a is operated, a numeric keypad for setting a numerical value of a suctioning pressure is displayed. The input numerical value is stored in a memory 71 (will be described later) as a setting value. The control unit 100 controls the suctioning pump based on the set suctioning pressure. As the suctioning switch 96b is operated, a suctioning pressure added (applied) to the suctioning ring 281 is turned ON and OFF. As the switch 96c is operated, a command signal is transmitted to the control unit 100. The control unit 100 which has received the signal controls the perfusion suctioning unit, thereby supplying liquid into the suctioning ring 281 through the liquid pipe (not illustrated), thereby obtaining a certain water level. As the switch 96d is operated, a command signal is transmitted to the control unit 100. The control unit 100 which has received the signal controls a suctioning/discharging unit, thereby discharging the liquid inside the suctioning ring 281 through the liquid pipe.

The switch 96e includes an upward cursor 97e and a downward cursor 98e. As the cursor 97e is operated, a command signal (an operational signal) for moving the interface unit 50 upward along the Z-direction is transmitted to the control unit 100. The control unit 100 which has received the signal controls the drive section 12, thereby moving the cover glass 51 upward. In contrast, as the cursor 98e is operated, the control unit 100 moves the cover glass 51 downward. A practitioner moves the eyeball fixing unit 280 while watching a moving image of the patient's eye E displayed in the display portion 92, thereby fixing the eyeball (details thereof will be described later). Therefore, the display portion 92 becomes means (a monitoring unit) for positioning the eyeball fixing unit 280.

The movement unit operation portion 97 is input means for inputting a command signal (an operational signal) to the first movement unit 10 so as to move in the XYZ-direction. An operation portion 270 includes cursors which are respectively arranged in positive and negative directions with respect to the X-direction, the Y-direction, and the Z-direction. As the cursors are operated, a command signal corresponding to the direction is transmitted to the control unit 100.

<Control Unit>

The control unit 100 (refer to FIGS. 3 and 7) includes a CPU 101, a ROM 102, a RAM 103, a non-volatile memory (not illustrated), and the like. The CPU 101 carries out various controls of the ophthalmic laser surgery apparatus 1 (for example, controlling generation of the below-described control data, controlling the laser source unit 310, controlling the scanning unit 330, controlling adjustment of a scanning speed of the concentration position, and the like). The ROM 102 stores various programs, initial values, and the like for controlling an operation of the ophthalmic laser surgery apparatus 1. The RAM 103 temporarily stores various items of information. The non-volatile memory is a non-fugitive storage medium which can maintain stored contents even though power supply is shut off.

The control unit 100 is connected with the first movement unit 10, the second movement unit 200, the laser irradiation unit 300, the illumination light source 60, the observation/image capturing unit 70, the focal adjustment unit 80, the operation unit 90, the suctioning pump, the perfusion suctioning unit, and the like.

the control unit 100 は, after completing fixation of the patient's eye E by using the eyeball fixing unit 280 and the interface unit 50, the position detection unit 370 is used to acquire the absolute position of a feature site (the anterior capsule of the crystalline lens) of the patient's eye E, thereby revising (aligning) the laser irradiation position.

The control unit 100 revises positional information for performing irradiation of a laser beam for surgical operation based on a surgical operation site (a region) set in the OCT image display portion 94 and absolute information acquired by the position detection unit 370 before performing irradiation of the laser beam for surgical operation. The control unit 100 emits a laser beam from the laser source unit 310 based on the revised surgical operation site, the surgical operation conditions, and the irradiation pattern. Then, the laser spot is moved in the ocular tissue by controlling the scanning unit (the galvano mirrors 363 and 366), thereby cutting and crushing the ocular tissue.

The control unit 100 controls driving of the first movement unit 10 based on a command signal from an eyeball fixing operation portion 470, thereby moving the eyeball fixing unit 280 and the interface unit 50 in the XYZ-direction together with the irradiation end unit 42. Accordingly, it is possible to perform positional alignment of the eyeball fixing unit 280 and the interface unit 50 in the XY-direction, and positional alignment of a coarse adjustment in the Z-direction.

The control unit 100 performs image processing of the tomographic image acquired by the OCT unit 71 and the like, and performs roles to acquire (to detect, to calculate)

and to display (display control) positions and shapes of the eyeball fixing unit 280, the interface unit 50, and a tissue of the patient's eye E. The control unit 100 (partially) functions as the monitoring unit for monitoring positions of the eyeball fixing unit 280 and the interface unit 50 by displaying the tomographic image or controlling driving of the eyeball fixing unit 280 and the interface unit 50 based on a result of image processing.

<Flow of Surgical Operation and Control Operation>

Subsequently, a flow of a surgical operation and a control operation of the apparatus 1 will be described with reference to FIG. 8 regarding an eyeball fixing operation in priority.

A practitioner attaches the eyeball fixing unit 280 to the connection portion 250. The practitioner causes the eyeball fixing unit 280 to fit the connection portion 250. Next, the practitioner presses a suctioning start button of the suctioning device (not illustrated). The suctioning device (not illustrated) performs suctioning of air in the space R formed between the connection portion 250 and the concave portion 283. As suctioning of air in the space R is performed, a negative pressure is generated inside the space R. Accordingly, the eyeball fixing unit 280 is adsorbed to the connection portion 250.

Next, the practitioner attaches the interface unit 50 to the holder 52 of the irradiation end unit 42. The practitioner operates the surgical operation condition display portion 95 of the display portion 92, thereby setting the surgical operation conditions. Here, selection of the irradiation pattern for crushing the crystalline lens is made. For example, selection of the irradiation pattern is made from a pattern of incising only the anterior capsule of the crystalline lens, a pattern of incising the anterior capsule and dividing the crystalline lens nucleus (for example, dividing into two sections, four sections, and eight sections), a pattern of incising the anterior capsule and crushing the crystalline lens nucleus into small pieces, and the like. Moreover, the practitioner uses the suctioning pressure setting section 96a to set a suctioning pressure applied when fixing the eyeball. The set signal of the irradiation pattern and the set signal of the suctioning pressure are transmitted to the control unit 100, thereby being stored in the RAM 103.

Next, the practitioner operates the operation unit 90 and causes the optical axis L1 of the laser irradiation unit 300 to be positioned (the XY-alignment) on the eye E of a patient lying on a bed or the like. The control unit 100 receives a signal from the operation unit 90, thereby driving the first movement unit 10 in the XY-direction (Step 1). The practitioner may perform the XY-alignment operation while watching an image of the anterior chamber captured by the observation/image capturing unit 70. For example, the practitioner may perform the alignment operation in the XY-direction by checking the luminescent spot, the pupil, the cornea, and the like projected in the frontal image of the anterior chamber displayed in the display portion 93.

Subsequently, the practitioner causes the first movement unit 10 to drive in the Z-axis direction (Step 2). Accordingly, the interface unit 50 and the eyeball fixing unit 280 integrally approach the sclera of the patient's eye E. Step 2 may start before Step 1 is completed.

The practitioner may work while watching a moving image displayed in the anterior chamber display portion 93 and the OCT image display portion 94. For example, the practitioner may check a contact state of the suctioning ring 281 with respect to the sclera while watching a moving image (the frontal image and the OCT image). The control unit 100 may perform image processing of the OCT image which is the moving image acquired by the OCT unit 310 and may extract a position of the corneal apex by extracting a shape of the cornea of the patient's eye E. Moreover, the control unit 100 may acquire the central position of the pupil by extracting the iris of the patient's eye E. Then, the control unit 100 may take a line passing through the corneal apex and the center of the pupil as a direction (axial information indicating an axis of the eyeball) of the patient's eye E. The control unit 100 may cause a symbol (a mark) A1 indicating the axis to superpose on the OCT image in a display (refer to FIG. 6). Moreover, the control unit 100 may perform image processing of the frontal image acquired by the frontal image acquisition unit 350, thereby extracting the central position of the pupil. The control unit 100 causes a symbol A2 indicating the central position of the pupil to superpose on the frontal image in a display. The symbols A1 and A2 may be displayed being updated in real time.

If an alignment state in the XY-direction with respect to the subject eye and a tilt state of the patient's eye E are determined to be appropriate, the control unit 100 controls the drive section 12 so as to move the irradiation end unit 42 further toward the patient's eye E in the Z-direction, thereby causing the suctioning ring 281 and the patient's eye E to adhere to each other.

As the suctioning ring 281 comes into contact with the patient's eye E, the load cell 206 detects a force of the patient's eye E pushing the eyeball fixing unit 280 upward (Step 3). As a force is detected by the load cell 206, the control unit 100 stops driving the first movement unit 10 (Step 4). In this case, for example, the control unit 100 acquires a position of the link 212 from the encoder 203, thereby storing the position in the RAM 103 as a position where the suctioning ring 281 and the patient's eye E are in contact with each other (Step 5).

Next, as shown in FIGS. 9A and 9B, the control unit 100 drives the drive section 226, thereby moving the pin 221 downward. The links 211 and 212 are moved downward due to gravity. The suctioning ring 281 is pressed against the patient's eye E as much as the weights of the link unit 210, the connection portion 250, the eyeball fixing unit 280, and the like. In this manner, the control unit 100 releases the suctioning ring 281 supported by the pin 221, thereby pressing the suctioning ring 281 against the patient's eye E (Step 6). Accordingly, sealing properties between the suctioning ring 281 and the patient's eye E are enhanced so that the suctioning ring 281 is easily adsorbed to the patient's eye E.

In Step 6, for example, a load applied when pressurizing the suctioning ring 281 against the patient's eye E may be set equal to or less than 300 g, and more preferably 200 g. Preferably, an appropriate load is applied to the patient's eye E so as to cause the patient's eye to be favorably adsorbed by the suctioning ring 281. For example, the link unit 210 may be designed so as to cause a load applied to the patient's eye E to be equal to or less than 300 g in a state of being separated from the drive section 226.

For example, the control unit 100 may cancel a load applied to the patient's eye E as much magnitude as an elastic force of the spring 222 by controlling the drive section 226 so as to cause the pin 221 to come into contact with the link 211.

Without being limited to an elastic force of the spring 222, for example, a load applied to the patient's eye E may be cancelled by installing a balance adjustment mechanism in the link unit 210. For example, a spindle may be fixed to an end portion of the link 211 on the joint 213 side. Accordingly, momentum works in the link 211 in a direction in which the suctioning ring 281 is moved upward, thereby cancelling the load applied to the patient's eye E.

The practitioner operates the switch 96b. The control unit 100 receives an operational signal from the switch 96b and transmits a control signal to the suctioning device (Step 7). The suctioning device starts the pump, thereby causing the suctioning ring 281 to be adsorbed to the patient's eye E. As the practitioner operates the switch 96c, liquid fills the inside of the suctioning ring 281. The control unit 100 may be configured to start suctioning after stopping a movement of the suctioning ring 281. The control unit 100 may be configured to supply liquid based on completion of adsorbing by the suctioning ring 281.

As liquid fills the inside of the suctioning ring 281, due to a difference of the refractive indexes between air and liquid, there is a possibility of positional deviation of a fixation target seen from a patient. In this case, since the eyeball is adsorbed by the suctioning ring 281, if a patient observes a fixation light, a burden is loaded onto the patient's eye E.

In order to prevent the burden thereof, the control unit 100 may control a fixation induction unit when liquid fills the inside of the suctioning ring 281. For example, the control unit 100 may move a lighting position of the fixation light. For example, the control unit 100 may move the lighting position of the fixation light based on the refractive index of the liquid, in consideration of a refractive angle at which a luminous flux of the fixation light refracts on a liquid level. The refractive angle and the like may be stored in the ROM 102 and the like, and may be calculated by the control unit 100.

In a state where the patient's eye E is subjected to suctioning by the suctioning ring 281, the control unit 100 causes the position of the suctioning ring 281 to return to a position at the time of being in contact with the patient's eye E. The control unit 100 reads out the position at the time when the suctioning ring 281 comes into contact with the patient's eye E, from the RAM 103 (Step 8). The control unit 100 drives the drive section 226 in accordance with a position read out from the RAM 103, thereby moving the pin 221 upward. The link 211 is pushed up by the pin 221. As the link 211 is pushed up, the link 212 rises in the Z-axis direction. As the link unit 210 is moved upward, the eyeball fixing unit 280 moves upward, and thus, a position of the suctioning ring returns to the position at the time of being in contact with the patient's eye E. Accordingly, the pressing force applied from the suctioning ring 281 to the patient's eye E is released. In this manner, the control unit 100 causes the position of the eyeball fixing unit 280 to return to the initial position (Step 9).

<Interface Positioning>

Next, the practitioner performs positioning of the interface unit 50 in the Z-direction with respect to the patient's eye E. The practitioner checks a position (a position of the height in the Z-direction) of the cover glass 51 and a position of the cornea and operates the operation unit 90 while watching the OCT image so as to cause a front surface (a lower surface) of the cover glass 51 to have a uniform positional relationship with respect to the cornea (the apex). As the positional relationship, for example, the corneal apex and the front surface of the cover glass 51 have a distance of approximately 1 mm. That is a distance in which the cover glass 51 is not in direct contact with the cornea so as not to apply a burden to a patient, without receiving an influence of oscillations on the water level of liquid.

The control unit 100 transmits the operational signal input by the operation unit 90 to the first movement unit 10 as a command signal. The control unit 100 drives the first movement unit 10 and moves the irradiation end unit 42 and the interface unit 50 in the Z-axis direction with respect to the patient's eye E (Step 10).

The second movement unit 200 is attached to the irradiation end unit 42 by the arm 202. Therefore, by driving the first movement unit 10, the second movement unit 200 is moved together with the irradiation end unit 42 in a direction of the patient's eye E.

In the present example, as shown in FIGS. 9A and 9B, when the interface unit 50 and the second movement unit 200 are moved by the first movement unit 10, the control unit 100 controls driving of the second movement unit 200 so as to cause the position of the eyeball fixing unit 280 to be uniformly maintained with respect to the patient's eye E (otherwise, an installation surface (a floor surface) of the apparatus) (Step 11).

For example, a movement amount in which the first movement unit 10 moves the second movement unit 200 and the eyeball fixing unit 280 in a direction approaching the patient's eye E is referred to as $\Delta Z1$, and a movement amount in which the second movement unit 200 moves the eyeball fixing unit 280 in a direction relatively approaching the irradiation end unit 42 is referred to as $\Delta Z2$. For example, in the control unit 100 of the present example, driving of the first movement unit 10 and the second movement unit 200 is controlled so as to cause the movement amount $\Delta Z1$ and the movement amount $\Delta Z2$ to be equivalent to each other.

For example, the control unit 100 causes a relationship between a driving amount (for example, the number of pulses of a pulse motor) and a movement amount of the link 212 (otherwise, the eyeball fixing unit 280) to be stored regarding each of the drive sections 12 and 226 of the first movement unit 10 and the second movement unit 200. Therefore, the control unit 100 may control driving of the second movement unit in accordance with a driving amount of the first movement unit 10. Accordingly, the first movement unit 10 and the second movement unit 200 can be controlled so as to cause the movement amount $\Delta Z1$ and the movement amount $\Delta Z2$ to be equivalent to each other.

In a case of the present example, the downward movement amount $\Delta Z1$ of the second movement unit 200 caused by the first movement unit 10 and the upward movement amount $\Delta Z2$ of the eyeball fixing unit 280 caused by the second movement unit 200 are cancelled. Accordingly, the interface unit 50 can be positioned with respect to the patient's eye E in a state where a position of the eyeball fixing unit 280 in the Z-axis direction is maintained unmovably with respect to the patient's eye E. Therefore, the eyeball fixing unit is pressed against the patient's eye E due to a movement of the first movement unit 10, thereby decreasing rising of ocular tension of the patient's eye E. In other words, it is possible to decrease a burden to a patient during a surgical operation.

In the present example, Steps 10 and 11 are processed at the same time. However, processing time therebetween may be deviated from each other. For example, Step 11 may be processed following after processing of Step 10.

While watching a detection result of a pressure caused by the load cell 206 without performing a servo control of the first movement unit 10 and the second movement unit 200, fluctuation of ocular tension can be suppressed and the eyeball can be fixed.

The practitioner may operate the operation unit 90 while watching a detection result (for example, an indicator) of a pressure of the load cell displayed in the display portion 92. The control unit 100 may drive the drive section 12, the drive section 226, or the like based on a signal from the operation unit 90 operated by a practitioner.

In the present example, a detection value of the load cell 206 is not subjected to a feedback in a movement control for the first movement unit 10 and the second movement unit. However, the detection result of the load cell 206 is monitored at all times so that locking performed by the lock portion 230 is released if the pressure reaches equal to or more than a threshold value. Accordingly, the patient's eye E is suppressed from being applied with an excessive burden.

Moreover, in the present example, for example, when the first movement unit 10 is driven, the control unit 100 controls the second movement unit 200 so as to cause the eyeball fixing unit 280 to be regularly maintained at a constant position with respect to the patient's eye E.

For example, the first movement unit 10 integrally moves the second movement unit 200 and the eyeball fixing unit 280 in a direction approaching the patient's eye E, and the second movement unit 200 moves the eyeball fixing unit 280 in a direction being separated from the patient's eye E. In this case, magnitude of a moving velocity in the Z-axis direction at the time of moving the eyeball fixing unit 280 by the first movement unit 10 is referred to as V1, and magnitude of a moving velocity in the Z-axis direction at the time of moving the eyeball fixing unit 280 by the second movement unit 200 is referred to as V2. In the present example, the control unit 100 controls the first movement unit 10 and the second movement unit 200 so as to cause the magnitude V1 and V2 of the moving velocity in the Z-axis direction become equivalent to each other.

For example, the control unit 100 causes a relationship between a driving velocity (for example, rotational speed of a motor) and a moving velocity of the link 212 (otherwise, the eyeball fixing unit 280) to be stored regarding each of the drive sections 12 and 226 of the first movement unit 10 and the second movement unit 200. Therefore, the control unit 100 may control driving of the second movement unit 200 in accordance with a driving amount of the first movement unit 10. Accordingly, the first movement unit 10 and the second movement unit 200 can be controlled so as to cause the magnitude V1 of the moving velocity and the magnitude V2 of the moving velocity become equivalent to each other.

Accordingly, in a state where the eyeball fixing unit 280 is maintained at a constant position at all times with respect to the patient's eye E, the control unit 100 allows the interface unit 50 (the cover glass 51) to be positioned with respect to the patient's eye E (Step 12). Therefore, it is possible to decrease rising of ocular tension caused by a movement of the eyeball fixing unit 280, pressing the patient's eye E by the suctioning ring 281.

As described above, the position of the eyeball fixing unit 280 is not necessarily constant with respect to the patient's eye E. However, it is preferable to maintain the position of the eyeball fixing unit 280 to the extent in which the patient's eye E is not applied with an excessive burden.

The control unit 100 may be configured to perform positioning of the cover glass 51 by detecting a position of the front surface of the cover glass 51 and a position of the upper surface of the eyeball fixing unit 280 through image processing of the OCT image.

In this manner, the eyeball of the patient's eye E is fixed, and the interface unit 50 is positioned. While a practitioner watches an image of the anterior chamber and a moving image such as the OCT image, the suctioning ring 281 and the interface unit 50 are moved in the Z-direction, and thus, positioning work can be simply performed. Moreover, by checking a moving image of the patient's eye E, it is possible to preferably fix the eyeball in accordance with the patient's eye, corresponding to positions of the sclera and the cornea which vary depending on the patient's eye.

The apparatus of the present embodiment has a configuration in which the suctioning ring 281 and the interface unit 50 provided in the apparatus main body are independently movable in the Z-direction, the interface unit 50 is moved with respect to the patient's eye fixed by the suctioning ring 281. Accordingly, the positional relationship between the patient's eye and the interface unit fixed by the suctioning ring 281 can be favorably adjusted, and thus, it is possible to preferably fix the eyeball in accordance with the patient's eye, corresponding to positions of the sclera and the cornea which vary depending on the patient's eye. Moreover, the interface unit 50 is movable with respect to the suctioning ring 281 in the Z-axis direction by the second movement unit in a state where a movement in the XY-direction is regulated, and thus, it is possible to avoid an occurrence of deviation between the interface unit 50 and the suctioning ring 281 in the XY-direction.

The apparatus of the present embodiment has a configuration in which the suctioning ring 281 and the interface unit 50 provided in the apparatus main body are independently movable in the Z-direction, and fixation of the suctioning ring 281 with respect to the patient's eye and an adjustment of the positional relationship between the patient's eye and the interface unit 50 fixed by the suctioning ring 281 can be smoothly performed, and thus, it is possible to efficiently perform a surgical operation.

<Adjustment of Focus>

In the apparatus 1 of the present example, when the front surface observation unit 75 and the objective lens 305 are moved in the Z-axis direction by the first movement unit 10, focus of the front surface observation unit 75 is adjusted by the focal adjustment unit 80 so as to be focused on the patient's eye E.

For example, as shown in FIGS. 10A and 10B, the first movement unit 10 moves toward the patient's eye E. In this case, the distance of the objective lens 305 to the patient's eye E and the distance of the front surface observation unit 75 to the patient's eye E become short. Therefore, an image of the patient's eye E formed at a position of the light receiving element 76 by the optical system of the front surface observation unit 75 is formed away from the light receiving element 76. Therefore, a frontal image of the patient's eye E detected by the light receiving element 76 becomes an image being out of focus.

For example, focus of the front surface observation unit 75 is adjusted with respect to the patient's eye E before being fixed by the eyeball fixing unit 280. For example, in an initial state, the light receiving element 76 is in focus at a position away from the suctioning ring 281 by 15 mm on the patient side. Accordingly, a practitioner can grasp the position of the patient's eye E before the patient's eye E comes into contact with the suctioning ring 281.

Firstly, a practitioner causes the eyeball fixing unit 280 to approach the patient's eye E by using the first movement unit 10. As the eyeball fixing unit 280 is moved so as to cause the patient's eye E to be positioned at a position away from the suctioning ring 281 by 15 mm, the light receiving element 76 is in focus with the patient's eye E. However, if the first movement unit 10 is further moved in order to bring the suctioning ring 281 into contact with the patient's eye E, the focusing position of the light receiving element 76 is deviated with respect to the patient's eye E. If the focusing position is deviated, the frontal image of the patient's eye E acquired by the light receiving element 76 is senile, thereby causing a problem in positioning of the patient's eye E and the eyeball fixing unit 280 in the XY-direction.

In such a case, in the present example, the control unit 100 may start controlling the focal adjustment unit 80 in accordance with a position or a movement amount of the first movement unit 10 after the light receiving element 76 is in focus with the patient's eye E by moving the first movement unit 10, for example. Then, the control unit 100 changes a position of the light receiving element 76 so as to cause an image of the patient's eye E formed by the objective lens 305 and the front surface observation unit 75 to be formed at a light receiving position of the light receiving element 76. For example, a distance between the light receiving element 76 and the patient's eye E on an observation optical path is changed.

For example, as shown in FIG. 10B, the control unit 100 controls the drive section 81 of the focal adjustment unit, thereby moving the light receiving element 76. As the objective lens 305 and the patient's eye E are moved in a direction approaching each other by the first movement unit 10, the control unit 100 causes the drive section 81 to move a position of the light receiving element 76 in a direction away from the patient's eye E. In this manner, the control unit 100 can adjust the focusing position of the front surface observation unit 75 by using the focal adjustment unit 80. A relationship between the movement amount when causing the objective lens 305 to approach the patient's eye E and the movement amount when moving the light receiving element 76 depends on the optical system and the like of the apparatus, and thus, it is possible to obtain experimentally. Moreover, the movement amount of the objective lens 305 and the movement amount of the light receiving element 76 can be also obtained logically as a design value. For example, when the objective lens 305 is caused to approach the patient's eye E by 35 mm, the light receiving element 76 is caused to be away by 2 mm, and thus, the light receiving element 76 can be in focus with the patient's eye E.

In this manner, when an arrangement of the front surface observation unit 75 is moved in accordance with a movement of the irradiation end unit 42, an image of the patient's eye E captured by the light receiving element 76 is out of focus. For example, if the image is out of focus, positioning of the suctioning ring 281 is performed in an obscure image. Therefore, for example, the patient's eye E is fixed in a state where the optical axis L2 of the patient's eye E is deviated and tilted with respect to the optical axis L1 of the laser irradiation optical system 320.

As described in the present example, when the distance between the front surface observation unit 75 and the patient's eye E changes, and the light receiving element 76 is out of focus, for example, the front surface observation unit 75 is caused to be in focus with the patient's eye E by the focal adjustment unit 80.

In this manner, it is easy to observe a state of the patient's eye E by adjusting focus of the front surface observation unit 75. Then, positioning of the suctioning ring 281 and positioning of the interface unit 50 can be favorably performed.

Moreover, in the present example, after fixing the patient's eye E by using the eyeball fixing unit 280, focus of the front surface observation unit 75 may be adjusted even when positional alignment of the irradiation end unit 42 is performed with respect to the patient's eye E.

For example, the control unit 100 moves the first movement unit 10 and causes the objective lens 305 and the interface unit 50 to approach the patient's eye E fixed to the eyeball fixing unit 280. Then, the patient's eye E is arranged in the irradiation position for laser irradiation. In accordance with a movement of the first movement unit 10, the front surface observation unit 75 is also moved. In other words, the focusing position of the front surface observation unit 75 is misaligned. In this case, for example, the control unit 100 controls the focal adjustment unit 80, thereby moving a position of the light receiving element 76. Accordingly, the focal adjustment unit 80 can cause the front surface observation unit 75 to be in focus with the patient's eye E from the standby position of the eyeball fixing unit 280 before fixing the patient's eye E to the irradiation position for laser irradiation. Accordingly, a practitioner can easily check the state of the patient's eye E from before fixing the eyeball until laser irradiation is performed.

The focal adjustment unit 80 may adjust focus of the light receiving element 76 in real time in accordance with a height of the eyeball fixing unit 280. For example, the control unit 100 detects the height in real time of the eyeball fixing unit from the movement amount of the first movement unit 10 or the second movement unit 200. Then, the control unit 100 may control the focal adjustment unit 80 in accordance with the detected height in real time, thereby adjusting focus of the light receiving element 76 in real time.

As the eyeball fixing is completed, a practitioner sets the surgical operation site. The practitioner operates the switch of the OCT image display portion 94, thereby performing planning. As the planning is completed, the control unit 100 controls the position detection unit 370 and acquires the absolute position for the feature site of the ocular tissue of the patient's eye E, thereby revising information of the laser irradiation position. The revision result is stored in the RAM 103.

As the practitioner operates the operation unit 90, the control unit 100 performs laser irradiation based on the surgical operation conditions which is set based on the operational signal, the irradiation pattern, and the revised information of the laser irradiation position (controlling of the laser irradiation optical system 320).

The crystalline lens of the patient's eye is cut and crushed and the anterior capsule of the crystalline lens is incised by performing laser irradiation. The control unit 100 notifies the practitioner of completion of laser irradiation through a buzzer (not illustrated). The practitioner operates the switch 97e, thereby moving the interface unit 50 upward. Moreover, the practitioner operates the switch 96d, thereby discharging liquid inside the suctioning ring 281. Then, the practitioner operates the switch 96b so as to release the adsorption state caused by the suctioning ring 281, thereby detaching the suctioning ring 281 from the patient's eye E. The control unit 100 may be configured to perform processing after completion of laser irradiation.

After detaching the eyeball fixing unit 280 and the interface unit 50, the patient's eye is subjected to a surgical operation by using another surgical operation apparatus, for example, a surgical operation apparatus for ultrasonic wave cataract.

In addition, the contents of planning of the docking may be corrected as well as the contents of the irradiation planning. For example, when the collimation axis or the optical axis of the eyeball is different between the preoperative image and the intraoperative image, the control unit 100 may control the fixation induction unit 120 such that the collimation axis induction is performed to automatically correct the direction of the axis.

In the description of the present example, the focal adjustment unit 80 adjusts focus of the observation/image capturing unit 70 by moving the light receiving element 76 of the observation/image capturing unit 70 with respect to the objective lens 305. However, the example is not limited thereto. For example, as shown in FIG. 11A, insertion and withdrawal of a focal adjustment lens may be performed on the optical path of the observation/image capturing unit 70. For example, a concave lens 83 is arranged on the optical path in the observation/image capturing unit 70, and the light receiving element 76 is in focus on a position away from the suctioning ring 281 by 15 mm. As the patient's eye E gradually approaches and reaches the position away from the suctioning ring 281 by 15 mm, focus of the observation/image capturing unit 70 coincides with the patient's eye E.

Next, when the patient's eye E reaches a position to be in contact with the suctioning ring 281, the control unit 100 causes a concave lens 82 to retract outside the optical path of the observation/image capturing unit 70. As a result, the light receiving element 76 is in focus in the vicinity of the patient's eye E which is docked on the suctioning ring 281. Moreover, when the irradiation end unit 42 approaches the laser irradiation position, the control unit 100 performs insertion of the convex lens 83 on the optical path of the observation/image capturing unit 70. As a result, the light receiving element 76 is in focus in the vicinity of the patient's eye E arranged at the laser irradiation position.

In this manner, the focusing position of the observation/image capturing unit 70 can be adjusted even by performing insertion and withdrawal of the optical element (for example, the concave lens 82 and the convex lens 83) on the optical path of the observation/image capturing unit 70.

For example, as shown in FIG. 11B, focus of the observation/image capturing unit 70 may be adjusted by moving the objective lens 305. For example, the irradiation end unit 42 is moved in a direction of the patient's eye E. In this case, the objective lens 305 is moved in a direction away from the patient's eye E. Even though the focusing position is misaligned due to a change of positions of the patient's eye E and the light receiving element 76, the light receiving element 76 can be in focus on the patient's eye E by moving the objective lens 305.

For example, focus of the observation/image capturing unit 70 may be adjusted by moving an image-forming lens (not illustrated) provided in the observation/image capturing unit 70.

As described above, the focal adjustment unit 80 may adjust focus of the light receiving element 76 of the observation/image capturing unit 70 by adjusting an arrangement of the light receiving element 76.

For example, the focal adjustment unit may switch a plurality of light receiving elements (not illustrated) which are provided in accordance with a height of the patient's eye E, for example. In this manner, the focal adjustment unit may adjust focus of the front surface observation unit 75 by switching the plurality of light receiving elements having different focusing positions from one another.

In the present example, the light receiving element 76 is in a state of being in focus away from the suctioning ring 281, before fixing the eyeball. In this manner, it is possible to favorably detect the patient's eye E before coming into contact with the suctioning ring 281 by being in focus away from the suctioning ring 281. Moreover, as described above, the light receiving element 76 is adjusted to be in focus with the patient's eye E, and thus, it is possible to capture an image in focus from before the patient's eye E comes into contact with the suctioning ring 281 until performing laser irradiation. Accordingly, the practitioner can appropriately observe a state of the patient's eye E during the surgical operation.

In the present example, for example, focusing is performed at a position away from the suctioning ring 281 by 15 mm. For example, focusing is performed at a position away from the cover glass 51 by 35 mm. The light receiving element 76 is favorably in focus at a position away from the suctioning ring 281 by 5 mm. Preferably, for example, focusing is favorably performed away from the cover glass 51 by 25 mm. At least before the patient's eye E comes into contact with the suctioning ring 281, it is preferable that the light receiving element 76 is in focus with the patient's eye E.

Figure 12A:
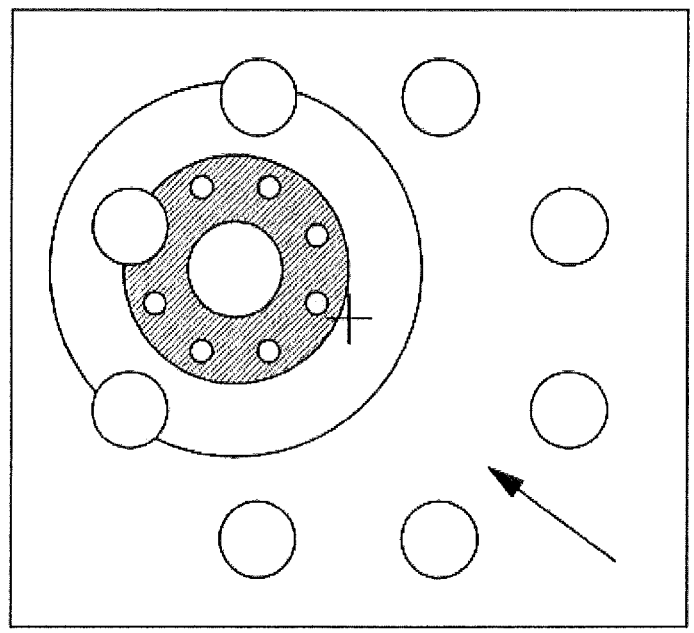
FIGS. 12A and 12B are diagrams for illustrating detection of alignment.
Figure 12B:
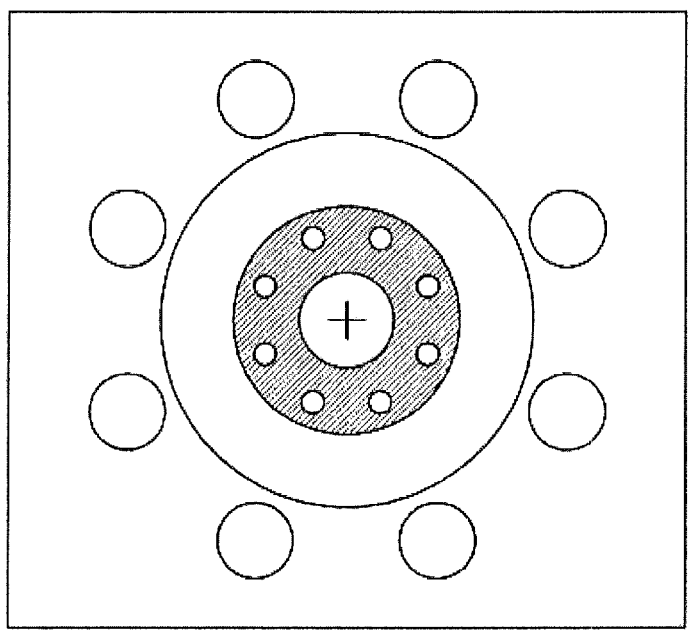

In the present example, the control unit 100 may detect the position of the patient's eye E based on an image of the anterior chamber of the patient's eye E acquired by the observation/image capturing unit 70. For example, the control unit 100 may detect the luminescent spot on the cornea formed by illumination light from the illumination light source, out of the frontal image. Then, the control unit 100 may obtain a distance to the apparatus in the XY-direction or the Z-axis direction of the patient's eye E based on a position of the detected luminescent spot. For example, as shown in FIGS. 12A and 12B, the control unit 100 may detect the position of the patient's eye E with respect to the irradiation end unit 42 from a position of the luminescent spot of the cornea projected in the frontal image. In this manner, the front surface observation unit 75 may function as the detection unit detecting the position of the patient's eye. As shown in FIGS. 12A and 12B, there is a case where the luminescent spot generated by illumination light reflected in a cover lens 51 and the like is projected in the frontal image. For example, a case of the cover lens 51 in a LASIK surgical operation and the like can be exemplified. the luminescent spot of the cover lens 51 and the like is detected at the same position in the frontal image at all times. The control unit 100 may read a position where the luminescent spot previously stored in a storage section is formed, thereby discriminating the luminescent spot of the cornea from the luminescent spot of the cover lens 51. Moreover, the luminescent spot of the cover lens 51 is likely to be projected larger than the luminescent spot of the cornea. Therefore, the control unit 100 may discriminate the luminescent spot of the cornea from the luminescent spot of the cover lens 51 based on the size of the luminescent spot.

The practitioner may operate the operation unit 90 so as to cause the position of the luminescent spot of the cornea projected in the frontal image to be arranged in the center of a display portion 93, thereby moving the first movement unit 10.

The position of the patient's eye may be detected by the OCT unit. For example, the position of the patient's eye may be detected from the tomographic image of the anterior chamber of the patient's eye captured by the OCT unit. The OCT unit also captures a tomographic image of the cornea of the patient's eye, the eyeball fixing unit 280, the interface unit 50, and the like. Therefore, the OCT unit 71 may function as the detection unit for detecting the position of the patient's eye E with respect to the apparatus. The control unit 100 may control the focal adjustment unit 80 in accordance with the position of the patient's eye E with respect to the apparatus detected by the OCT unit, thereby adjusting focus of the light receiving element 76.

After the patient's eye E is fixed by the suctioning ring 281, an approximate position of the patient's eye E may be detected based on the position of the eyeball fixing unit 280. For example, the control unit 100 detects the position of the eyeball fixing unit 280 based on a driving amount (the number of pulses of the pulse motor) of the first movement unit or the second movement unit.

As described above, the surgical operation apparatus 1 may detect the position of the patient's eye E by using the detection unit (for example, the observation/image capturing unit or the control unit). Then, the control unit 100 may control the focal adjustment unit based on the detected position of the patient's eye E, thereby adjusting focus of the front surface observation unit 75.

The detection unit may detect the luminescent spot of the cornea, the pupil, the corneal limbus, a conjunctiva blood vessel, and the like. The detection unit may switch a detection target in accordance with an operation of the surgical operation apparatus 1. For example, when detecting the alignment state of the apparatus 1 and the patient's eye E, the detection unit may set the luminescent spot of the cornea as the detection target. The luminescent spot of the cornea is easily detected and detection accuracy of the alignment state can be enhanced. Moreover, as the detection target, a laser irradiation target (for example, the crystalline lens, the cornea, and the like) may be adopted as the detection target. For example, when performing planning of a surgical operation, it is preferable that the observation image is in focus on the irradiation target in order to check the laser irradiation target through a vivid image. Therefore, the detection unit may detect the laser irradiation target and adjust focus of the observation/image capturing unit 70. Focus may be adjusted by detecting the irradiation target.

The control unit 100 may perform a focal adjustment of the light receiving element 76 at all times by the focal adjustment unit 80. The control unit 100 may also calculate a distance from the irradiation end unit 42 to the patient's eye E based on a position of the light receiving element 76. For example, a position where the light receiving element 76 is in focus can be calculated through an optical design value. In this manner, a position of the patient's eye E in the Z-axis direction may be acquired by utilizing a focus state of the light receiving element 76.

In the above descriptions, the focal adjustment unit 80 has the drive section 81 and is automatically controlled by the control unit 100. However, the focal adjustment unit 80 is not limited thereto. For example, a practitioner may manually move the position of the light receiving element 76 and the like, thereby performing a focal adjustment.

In the present example, the position of the patient's eye E is detected with respect to a wide region from a position before performing docking of the patient's eye E and the suctioning ring 281 to a position where the patient's eye E is irradiated with a laser. Therefore, in the present example, between cases of the patient's eye is respectively away from and close to the objective lens 305, the optical paths in which emitted light from the illumination light source 60 is reflected by the cornea and is received by the light receiving element 76 are different from each other.

For example, when the patient's eye E is away from the objective lens 305, illumination light passes the outside of the cover glass 51 and reaches the cornea penetrating the inside of the suctioning ring 281. Then, the illumination light reflected by the cornea is reflected in the Z-axis direction, thereby being received by the light receiving element 76. Meanwhile, when the patient's eye E is close to the objective lens 305, the illumination light transmits the inside of the cover glass 51 and reaches the cornea penetrating the inside of the suctioning ring 281. Then, illumination light reflected by the cornea is reflected in the Z-axis direction, thereby being received by the light receiving element 76.

In this manner, in the present example, even in any one of the cases where the patient's eye are respectively away from and close to the objective lens 305, the illumination light source 60 is arranged so as to be able to form the luminescent spot on the cornea. Accordingly, it is possible to form the luminescent spot on the cornea in a elongated region by using the same illumination light source 60.

In the above description, the second movement unit 200 moves in the XYZ-direction by the first movement unit 10. However, the second movement unit 200 is not limited thereto. For example, the second movement unit 200 may be attached to the main body portion 2 which is not influenced by driving of the first movement unit 10. In this case, it is favorable if the second movement unit 200 can hold the eyeball fixing unit 280 to be movable in the XYZ-direction with respect to the main body portion 2. Moreover, in this case, driving of the second movement unit 200 in the XY-direction may be synchronized with driving of the first movement unit 10.

In the above description, the suctioning ring and the interface unit are disposable types (one-use types). However, the suctioning ring and the interface unit are not limited thereto. It is acceptable as long as the eyeball can be fixed. The suctioning ring and the interface unit may be reuse types. In this case, each of the units are formed by using a material such as stainless steel and glass which can be repeatedly sterilized.

In the present embodiment described above, after the patient's eye is adsorbed by the suctioning ring, the interface unit is configured to be brought into contact with the patient's eye. However, the configuration is not limited thereto. It is acceptable as long as the eyeball can be fixed. The working may be performed in reverse order.

In the above description, the suctioning ring and the interface unit are configured to move in the Z-direction. However, the configuration is not limited thereto. It is acceptable as long as the two units are configured to individually move. Each of two units may be configured to move (otherwise, rotate) in the XY-direction.

In the above description, the eyeball fixing unit is configured to be positioned in the OCT image by using a captured image (a moving image). However, the configuration is not limited thereto. For example, a symbol (an illustration, a frame, and the like) showing at least a position of a ring of the suctioning ring may be configured to superpose on the OCT image in the display. For example, the position of the ring of the suctioning ring may be configured to be obtained from a configuration of a suctioning ring member and a detection signal of a sensor of a first holding unit, thereby being displayed in the OCT image. Accordingly, it is possible to check a position of a member which is unlikely to be projected in an image, through a monitor.

A shape of the patient's eye may be configured to be extracted from the OCT image through image processing performed by the control unit and the like, thereby being utilized in the eyeball fixing and the like. For example, the OCT image (an OCT image acquired by another image capturing apparatus may be adopted) acquired before the eyeball fixing operation is subjected to image processing, thereby extracting a shape of the cornea and a shape in the vicinity of the cornea (a shape of the eyeball) where the suctioning ring comes into contact. The shape of the eyeball is preferably a three-dimensional shape acquired by an orthogonal lines (B-scan) passing the vicinity of the corneal apex. When performing an eyeball fixing operation, a shape of the cornea of the patient's eye is acquired and matched with a shape of the cornea previously acquired, thereby acquiring the shape and the position in the vicinity of the cornea of the patient's eye. The acquired shape and position in the vicinity of the cornea are configured to be displayed in symbols on the OCT image. Accordingly, even though an image of the vicinity of the cornea cannot be captured by the OCT unit, a practitioner can perform positioning of the suctioning ring while checking (estimating) the position in the vicinity of the cornea.

In the above description, the OCT unit is configured to acquire the OCT image including at least a portion of the eyeball fixing unit and the interface unit. However, the configuration is not limited thereto. It is acceptable as long as the position and the shape of the eyeball fixing unit and the like are configured to be able to be grasped on the OCT image. For example, an illustration and the like showing a portion of the eyeball fixing unit and the like may be configured to be displayed on the OCT image as the symbol. Specifically, the control unit acquires a position of the suctioning ring from the sensor and information (a result of positional detection) of the alignment unit, thereby displaying an illustration of a shape tracing the suctioning ring, on the OCT image. The illustration traces the shape from design information of the suctioning ring. The control unit updates the display based on the positional information of the sensor. With reference to the illustration on the OCT image, a practitioner can know a position of the suctioning ring, and thus, the positional alignment is easily performed. Similarly, in a case of the interface unit as well, information of the drive section and the alignment unit is acquired, thereby displaying the illustration of the interface unit on the OCT image showing (at least) the cover glass. The symbol may be displayed even though a portion of the eyeball fixing unit and the interface unit is included in the OCT image.

In the above description, a moving image of the OCT image is configured to be displayed on a monitor. However, the configuration is not limited thereto. It is acceptable as long as a state where the control unit performs positional alignment of the eyeball unit and the like is configured to be able to be monitored. The capture OCT image may be configured to be processed inside thereof. In this case, the control unit functions as the monitoring unit.

In the above description, the OCT unit is used as the tomographic image capturing unit in the configuration. However, the configuration is not limited thereto as long as deepness information and the tomographic image of the patient's eye can be captured. For example, a Scheimplug camera unit may be used in the configuration In the above description, the OCT image and the like are configured to be used in positional alignment of the eyeball fixing unit before performing laser irradiation (before performing a surgical operation). However, the configuration is not limited thereto. The OCT image may be configured to be used in monitoring (checking) an eyeball fixing state during the laser irradiation (during the surgical operation). For example, the control unit is configured to detect a movement of the patient's eye with reference to the OCT image through image processing. The control unit obtains information of the feature portion of the patient's eye such as the shape of the cornea and the position of the corneal apex, with reference to the OCT image. The control unit detects a movement of the feature portion by monitoring a portion of the feature portion. For example, when the eyeball has moved due to a suctioning brake or the like, the control unit is configured to stop laser irradiation based on the detection result, thereby notifying a practitioner. In such a case, compared to detection of adsorption state using the sensor for monitoring a suctioning pressure of the suctioning ring, the adsorption state can be promptly detected. Moreover, without being limited to the adsorption state, the control unit may be configured to control detecting of variation of the patient's eye with reference to the OCT image and the like, stopping of laser irradiation, and revising laser irradiation (a position thereof).

In the above description, at least a portion of the eyeball fixing unit and at least a portion of the interface unit are configured to be projected in the OCT image. However, the configuration is not limited thereto. It is acceptable as long as the positional alignment of the interface unit can be achieved through the configuration. It is acceptable as long as a portion of the interface unit is projected in the OCT image. Accordingly, the positional relationship of the cornea and the interface unit is easily acquired in an image display and image processing.

In the above description, a portion of the eyeball fixing unit and a portion of the interface unit are configured to be projected in the OCT image. However, the configuration is not limited thereto. It is acceptable as long as positional alignment of the eyeball fixing unit and the interface unit can be performed with respect to the cornea through the configuration. Each unit is not necessarily projected in the OCT image. The positional relationship of the OCT unit and the cornea (surface) can be acquired from the captured OCT image. Therefore, as the positional relationships are set among the OCT unit, the eyeball fixing unit, and the interface unit, it is possible to perform the positional alignment of each unit by acquiring the positional relationship between the cornea (the patient's eye) and the eyeball fixing unit utilizing the OCT image in which the eyeball fixing unit and the like are not projected.

In the above description, in the positional alignment of the eyeball fixing unit and the interface unit utilizing the OCT image, each unit is configured to be fixedly arranged in the apparatus main body. However, the configuration is not limited thereto. It is acceptable as long as the eyeball is configured to be fixed to the laser irradiation unit. For example, the eyeball fixing unit may be a unit independent of the apparatus. In this case, during the eyeball fixing work, independent positioning of the eyeball fixing unit is easily performed by adopting the OCT image and the like.

In the above description, the eyeball fixing unit (the suctioning ring) is configured to perform suctioning and adsorptive fixing of the eyeball. However, the configuration is not limited thereto. It is acceptable as long as the eyeball is configured to be able to be fixed. For example, the eyeball fixing unit may come into contact with the eyeball and suppress a movement of the eyeball.

In the above description, the ophthalmic laser surgery apparatus provided with a laser beam is exemplified. However, the example is not limited thereto. The configuration is acceptable as long as the eyeball of the patient's eye (the patient's eye) is fixed, and a surgical operation and treatment is performed by irradiating the ocular tissue of the fixed patient's eye with a laser beam. For example, an ophthalmic laser surgery apparatus for selective laser trabeculoplasty may be adopted. In this case, the laser beam is a laser and the like of visible light, and the size of the laser spot is several hundred μm, thereby irradiating the trabeculum on the angulus iridocornealis of the patient's eye with the laser beam.

As described above, the present invention is not limited to the embodiment, and various modifications can be made. The present invention includes such modifications within a scope sharing the same technical idea.

<Additional Portion>

The ophthalmic laser surgery apparatus according to the present example may include a configuration described below.

<Fixation Induction Unit>

For example, the fixation induction unit 120 projects the fixation target for performing fixation of the subject eye (refer to FIG. 3). The fixation induction unit 120 may change the sight direction of the patient's eye E before being docked by changing the presentation position of the fixation target. The fixation induction unit 120 induces the fixation direction of the eye E in order to induce the optical axis of irradiation of a surgical operation laser and the optical axis of the patient's eye into a predetermined positional relationship.

The fixation induction unit 120 is controlled by the control unit 100. The control unit 100 may control the fixation induction unit 120 based on an operational signal from the operation portion which is operated by a practitioner. The control unit 100 may automatically control the fixation induction unit 120 (details thereof will be described later).

In more details, for example, the fixation induction unit 120 may include a light source 121, a dichroic mirror 122, and the like. The light source 121 may project the fixation target onto the patient's eye E. For example, the dichroic mirror 122 branches the optical axis L5 of a front surface image capturing unit 75 and an optical axis L6 of the fixation induction unit 120. As the light source 121, a light source emitting light including at least visible light is used. For example, the light source 121 may include a plurality of beams of the fixation light, and each beam of the fixation light is arrayed at a position different from each other on a surface orthogonal to the optical axis. The control unit 100 can switch the lighting position of the fixation light in order to switch the sight direction of the patient's eye E. The fixation induction unit 120 may switch the lighting position of the fixation light by causing the drive section to move a single beam of fixation light, or may switch the lighting position of the fixation light by using a display device (for example, a liquid crystal display, an organic EL display, and the like).

<Observation Optical System 70>

An observation optical system 70 (also referred to as the observation/image capturing unit) 70 (refer to FIG. 3) allows a practitioner to observe the patient's eye E and captures a tissue to be a treatment target. As an example, the observation optical system 70 of the present embodiment includes a tomographic image capturing unit 71 and the front surface image capturing unit 75. The optical axis L3 of the observation optical system 70 is coaxial with the optical axis L1 of the laser beam by the beam combiner 72. The optical axis L3 is branched into the optical axis L4 of the tomographic image capturing unit 71 and the optical axis L5 of the front surface image capturing unit 75 by a beam combiner 73. The observation optical system 70 may function as a portion of the detection unit detecting the positional relationship between the surgical operation apparatus 1 and the patient's eye E. For example, the observation optical system 70 may function as a first detection unit detecting a position of the patient's eye E in the XY-direction. Moreover, the observation optical system 70 may function as a second detection unit detecting the position of the patient's eye E in the optical axis direction.

<Tomographic Image Capturing Unit 71>

The tomographic image capturing unit 71 acquires a tissue of the tomographic image of the patient's eye E by using an optical interference technology. For example, in the observation optical system 70 of the apparatus, the tomographic image capturing unit 71 capable of full-range image capturing may be used. The aforementioned "full-range image capturing" denotes image-capturing in which any one of a real image and a virtual image acquired by the tomographic image capturing unit 71 is eliminated. Refer to JP-A-2012-223264 for more details.

The ophthalmic laser surgery apparatus 1 of the present embodiment can set a position where a laser beam is concentrated based on the tomographic image of the patient's eye E captured before performing the surgical operation. As a result, the ophthalmic laser surgery apparatus 1 can generate the control data for controlling an irradiation operation (for example, an operation of the drive sections 353, 362, and 365) of a laser beam, by using the tomographic image.

Figure 13:
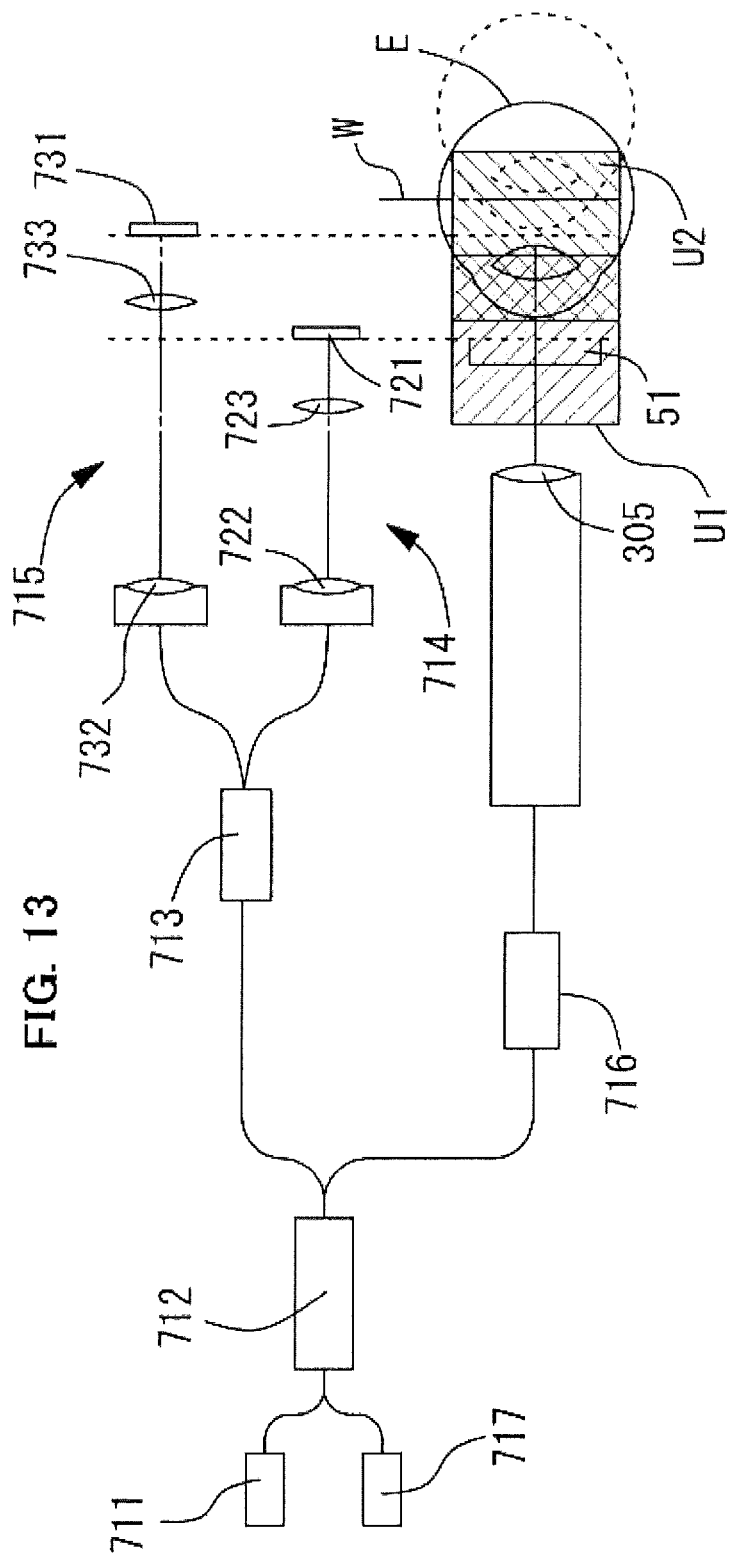
FIG. 13 is a diagram for illustrating a tomographic image capturing unit.

As shown in FIG. 13, for example, the tomographic image capturing unit 71 includes a light source 711, a light splitter 712 (for example, a coupler), an optical switch 713, a first reference optical system 714, a second reference optical system 715, an optical scanner 716, a detector 717, and the like.

The light source 711 emits measurement light (for example, infrared light). The light splitter 712 divides a luminous flux emitted from the light source 711 into measurement light and reference light. The measurement light emitted from the light splitter 712 is guided to the patient's eye E. The reference light emitted from the light splitter 712 is guided to the optical switch 713. The optical switch 713 guides the reference light generated by being divided by the light splitter 712 to the first reference optical system 714 or the second reference optical system 715. The optical switch 713 switches the optical path to the first reference optical system 714 and the optical path to the second reference optical system 715. The light splitter 712 may be a beam splitter, a circulator, and the like in addition to a coupler.

For example, the first reference optical system 714 may include a first reference mirror 721, a collimator lens 722, a concentration lens 723, and the like. The first reference mirror 721 reflects the first reference light so as to cause the first reference light to have a predetermined optical path length. The collimator lens 722 causes the first reference light to be a parallel luminous flux. For example, the concentration lens 723 causes the first reference light to be concentrated toward the first reference mirror 721.

The first reference light emitted from the optical switch 713 passes through an optical fiber, thereby being guided to the first reference optical system 714. For example, the first reference light passes through the collimator lens 722, thereby turning into the parallel luminous flux. For example, the first reference light turned into the parallel luminous flux is concentrated by the concentration lens 723 and is reflected by the first reference mirror 721 thereafter. The first reference light reflected by the first reference mirror 721 is guided to the optical switch 713 again.

The optical path length of the first reference light is determined by an optical arrangement of the first reference optical system 714. For example, the optical path length of the first reference light is determined by a position of the first reference mirror 721. For example, in the first reference optical system 714, a position of the first reference mirror 721 may be set so as cause to cause the optical path length of the measurement light reflected by the interface unit 50 to coincide with the optical path length of the first reference light (refer to FIG. 13). As a result, in the tomographic image capturing unit 71, an image capturing region which can capture the eyeball fixing unit 280 can be set as the first image capturing region.

The second reference optical system 715 may include a second reference mirror 731, a collimator lens 732, a concentration lens 733, and the like. The second reference mirror 731 reflects the second reference light so as to cause the second reference light to have a predetermined optical path length. The collimator lens 732 causes the second reference light to be a parallel luminous flux. The concentration lens 733 concentrates the second reference light on the second reference mirror 731.

The second reference light emitted from the optical switch 713 passes through an optical fiber, thereby being guided to the second reference optical system 715. For example, the first reference light passes through the collimator lens 732, thereby turning into the parallel luminous flux. For example, the second reference light turned into the parallel luminous flux is concentrated by concentration lens 733 and is reflected by the second reference mirror 731. The second reference light reflected by the second reference mirror 731 is guided to the optical switch 713 again.

The optical path length of the second reference light is determined by an optical arrangement of the second reference optical system 715. For example, the optical path length of the second reference light is determined by a position of the second reference mirror 731. For example, in the first reference optical system 714, a position of the second reference mirror 731 may be set so as to cause the optical path length of the measurement light reflected by the cornea of the patient's eye E to coincide with the optical path length of the second reference light (refer to FIG. 13). As a result, in the tomographic image capturing unit 71, an image capturing region which can capture the cornea of the patient's eye E can be set as the second image capturing region.

After being incident on the optical switch 713, the first reference light and the second reference light are incident on the light splitter 712 again. The light splitter 712 synthesizes the measurement light reflected by the patient's eye E with the first reference light or the second reference light. Synthetic light of the reference light and the measurement light is detected by the detector 717. For example, the first reference light reflected by the first reference mirror 721 may be synthesized with the measurement light reflected by the interface unit, thereby being received by the detector 717 (the light receiving element) 120. For example, the second reference light reflected by the second reference optical system 715 may be synthesized with the measurement light reflected by the cornea of the patient's eye E, thereby being received by the detector 717 (the light receiving element) 120.

As the tomographic image capturing unit 71 of the present example, for example, a first image capturing region U1 and a second capturing region U2 may be set by providing first and second reference optical systems having different optical path lengths from each other (refer to FIG. 13).

As described above, the surgical operation apparatus of the present example can widen an image capturing range of normal OCT by providing the image capturing region U1 which can acquire an interference signal by the first reference optical system 714, and the image capturing region U2 which can acquire an interference signal by the second reference optical system 715. Accordingly, it is possible to observe both a contact position W at which the cornea of the patient's eye E comes into contact with the suctioning ring 281, and the interface unit 50.

The optical scanner 716 deflects the measurement light emitted from the light source. For example, the optical scanner 716 may be configured to be of two galvano mirrors. In this case, rotational axes of the two galvano mirrors are preferably orthogonal to each other. The optical scanner 716 deflects the measurement light in a two-dimensional manner based on a command signal from the control unit 100. The control unit 100 controls the optical scanner 716, thereby scanning the measurement light in the XY-direction with respect to the patient's eye E. In the present example, scanning of the measurement light is performed in the anterior chamber of the patient's eye E. For example, the control unit 100 obtains the tomographic image by arranging depth information (deepness information) obtained at each scanning position, on a straight line (that is, B-scan).

The optical scanner 716 may be a mechanism deflecting light. For example, in addition to reflective mirrors (a galvano mirror, a polygon mirror, and a resonant scanner), an acousto optical modulator (AOM) and the like which change (deflect) a forward direction of light are used.

The detector 717 detects an interference state between the measurement light reflected by the fundus, and the reference light. In a case of a Fourier domain type, spectral intensity of light is detected by the detector 717, thereby acquiring a depth profile (an A-scan signal) by performing Fourier transformation with data related to spectral intensity. As the tomographic image capturing unit 71, for example, a spectral-domain (an SD method) and a swept-source (an SS method) are exemplified. Moreover, a time-domain (a TD method) may be adopted. In this case, an optical coherence tomography technology can be utilized. For example, refer to JP-A-2013-248303 and JP-A-2013-248304.

<Front Surface Image Capturing Unit>

The frontal image capturing unit 75 (refer to FIG. 3) acquires frontal image of the patient's eye E. For example, the frontal image capturing unit 75 of the present example includes the light receiving element 76. The frontal image capturing unit 75 captures the patient's eye E illuminated by visible light or infrared light. The frontal image of the patient's eye E captured by the frontal image capturing unit may be displayed in the display portion 92 (will be described later). A practitioner can observe the patient's eye E from the front by watching the display portion 92.

<Planning Screen>

Figure 14:
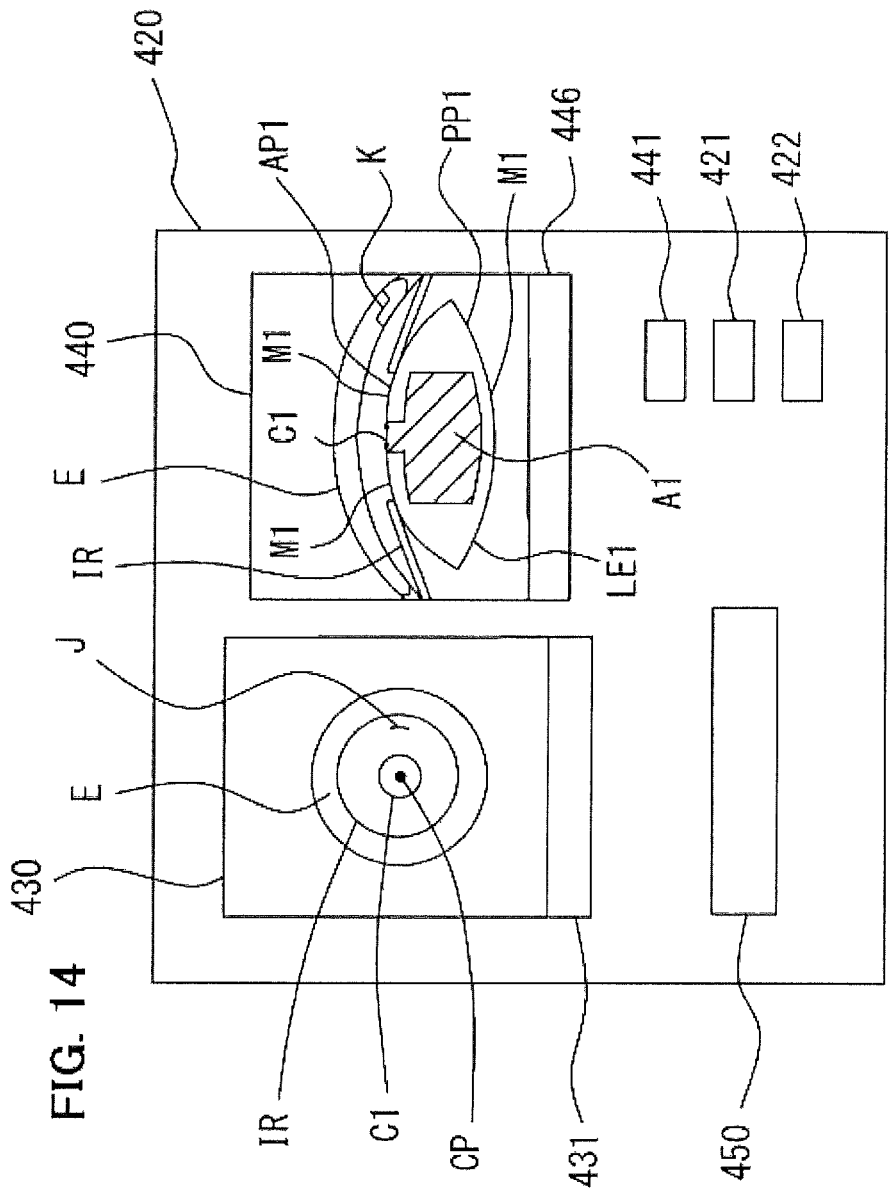
FIG. 14 is a diagram illustrating another display of the monitor.

The display portion 92 may display a planning screen. As shown in FIG. 14, for example, the planning screen may display an anterior chamber image display portion displaying region 430, a tomographic image displaying region 440, a surgical operation condition display portion 450, a switch 421, a switch 422, and the like. The anterior chamber image display portion displaying region 430 displays the anterior chamber of the surgical eye E. The tomographic image displaying region 440 displays the tomographic image of the anterior chamber of the surgical eye E. The surgical operation condition display portion 450 displays conditions of a surgical operation. The switch 421 starts setting work (planning) of a surgical operation site. The switch 422 confirms the designated surgical operation site (planning is designated). In the tomographic image displaying region 440, the practitioner designates a surgical operation site (laser irradiation range). The surgical operation site designated on the display portion 92 is set as the laser irradiation position in the tomographic image. The surgical operation site set by the control unit 100 is stored in the RAM 103. The switches 421 and 422 function to switch the mode of the apparatus 1 to the planning mode. The display portion 92 (the tomographic image displaying region 440) functions as a surgical operation site setting unit.

<Preoperative Planning>

The ophthalmic laser surgery apparatus of the present example may perform preoperative planning as in the following descriptions.

Hereinafter, an example of planning performed by using the apparatus before a surgical operation will be described. In the present example, shape information of the patient's eye E is acquired before a surgical operation, and planning of the surgical operation is performed using the acquired image. For example, as the planning, it is possible to exemplify irradiation planning for a pattern such as cornea incision, anterior capsule incision, and crystalline lens crushing, and operation positions, or planning for the docking steps performed when fixing the patient's eye E by the eyeball fixing unit 280. As the shape information of the patient's eye E used in planning, for example, a cornea shape, a crystalline lens shape, an iris shape, an angulus iridocornealis shape, and the like are acquired.

For example, the practitioner acquires the shape information of the patient's eye E by using an anterior chamber image capturing apparatus several days before the surgical operation. As the anterior chamber image capturing apparatus, an anterior chamber image capturing apparatus arranged in another casing different from the surgical operation apparatus 1 may be adopted, and the anterior chamber image capturing apparatus may be an apparatus for capturing an image of the patient's eye E in a sitting state. Moreover, as the anterior chamber image capturing apparatus, an anterior chamber image capturing apparatus integrally provided with the surgical operation apparatus 1 (for example, the observation/image capturing unit 70) may be adopted, and the anterior chamber image capturing apparatus may be an apparatus for capturing an image of the patient's eye E in a lying state.

For example, the anterior chamber image capturing apparatus captures at least any one of the tomographic image of the patient's eye E and the frontal image and acquires the shape information of the patient's eye E. For example, as the tomographic image of the patient's eye E, a noninvasive apparatus such as OCT, SLO, and the Scheimplug camera capable of capturing the tomographic image may be used.

The control unit 100 may acquire multiple tomographic images having B-scan directions different from one another, thereby storing the tomographic images in the RAM 103. For example, the tomographic image of B-scan for every 30-degree step with respect to the Y-direction is acquired. For example, 6 images may be acquired at 90 degrees, 120 degrees, 150 degrees, 180 degrees, 210 degrees, and 240 degrees. It is advantageous in that three-dimensional data of the anterior chamber can be obtained by acquiring multiple (at least two tomographic images tomographic image as described above. The control unit 100 may acquire three-dimensional data of the anterior chamber including multiple tomographic images adjacent to each other by performing raster scanning in the XY-direction. It is preferable that the control unit 100 is configured to acquire at least two tomographic images orthogonal to each other including the optical axis of laser irradiation.

When an external anterior chamber image capturing apparatus is used, it is preferable that data can be transceiveable between the external anterior chamber image capturing apparatus and the surgical operation apparatus 1. For example, the external anterior chamber image capturing apparatus and the surgical operation apparatus 1 may be connected by a cable or radio, and may transceive the data through a storage medium such as a flash memory. The control unit 100 acquires the preoperative observation image captured by an external observation apparatus, thereby storing the image in the RAM 103 and the like. The control unit 100 may perform imaging of an eyeball shape of the patient's eye E from the observation image. Then, the control unit 100 may acquire the shape information based on a result of the imaging, thereby performing setting (irradiation planning) of a surgical operation conditions. Naturally, for example, the observation image used in preoperative planning may be captured by the observation optical system 70 (for example, the observation/image capturing unit 70) provided in the surgical operation apparatus 1.

FIG. 14 is a diagram showing a display screen of the display portion 92. As shown in FIG. 14, after the observation image is acquired by the anterior chamber image capturing apparatus and the like, if a practitioner operates (touches) the switch 421, a command signal to start planning is transmitted to the control unit 100. For example, based on the command signal, the control unit 100 causes an anterior chamber image displaying region 430 to display a still image of the acquired anterior chamber image of the patient's eye E and causes the tomographic image displaying region 440 to display a still image of the tomographic image of the anterior chamber.

For example, the control unit 100 allows the surgical operation site to be designated on the anterior chamber image displaying region 430 and the tomographic image displaying region 440. A practitioner designates a region (the diameter of a circle and the like) for anterior capsule incision on the anterior chamber image of the anterior chamber image displaying region 430. The control unit 100 causes a position (a circle) for the anterior capsule incision with respect to the center of the pupil to be displayed by performing image processing of the anterior chamber image. Moreover, a practitioner designates a region of the tomographic image of the tomographic image displaying region 440 for crushing or incising of the cornea and the crystalline lens. The control unit 100 designates a crushing region by performing image processing of the tomographic image of the anterior chamber (details thereof will be described later). The surgical operation site (region) in the crystalline lens is determination of a region in a depth direction (the Z-direction). If the switch 422 is operated, the planning at the current stage is confirmed. The control unit 100 causes positional information of the anterior capsule incision in the anterior chamber image and information of the surgical operation site (region) on the tomographic image to be stored in the RAM 103 (setting of the surgical operation site) as the surgical operation site information (planning information).

<Display of Monitor and Planning>

Next, designation of the surgical operation site and image processing performed on a monitor will be described. Here, processing after an operation of the switch 421 will be described.

In the anterior chamber image displaying region 430, the anterior chamber image of the surgical eye E is displayed. At a lower portion of the anterior chamber image displaying region 430, an incision size display section 431 which shows a size of a circle for the anterior capsule incision is arranged. The control unit 100 performs image processing, thereby acquiring the center of the pupil of the anterior chamber image. The control unit 100 obtains a position of the center of the pupil based on a shape of iris IR in the anterior chamber image. If the anterior chamber image display portion displaying region 430 is operated, the control unit 100 causes the anterior chamber image to display the center of the pupil CP. Then, the control unit 100 causes the anterior chamber image to display a circle C1 mainly in the center of the pupil CP. The circle C1 indicates an incision position of the anterior capsule through laser irradiation. The diameter of the circle C1 is displayed so as to be a diameter shown in the incision size display section 431. As a practitioner operates the incision size display section 431, an increase/decrease switch (not illustrated) is displayed. The incision size can be changed by the increase/decrease switch. The incision size displayed in the incision size display section 431 is stored in the RAM 103.

The shape of the anterior capsule incision may be configured to select a preset figure such as an ellipse, for example, without being limited to a circle. Moreover, the circle C1 (the center thereof) may be configured to be deflected (shifted in the XY-direction) from the center CP of the pupil. For example, a section for inputting a distance to deflect the circle C1 is displayed, thereby having a configuration to allow a practitioner to input a desired distance. Moreover, the center of the circle C1 may be the apex of the crystalline lens without being limited to the center of the pupil. The apex of the crystalline lens can be obtained by extracting the apex of the anterior capsule in the multiple tomographic images.

In the tomographic image displaying region 440, the tomographic image in the Y-direction passing the central optical axis (the central optical axis of the laser beam) of the laser irradiation optical system in the surgical eye E. At the lower portion of the tomographic image displaying region 440, a margin display section 441 displaying a margin amount for crushing (incising) of the crystalline lens nucleus is arranged. The aforementioned margin denotes a region which is provided on a front side from the posterior capsule PP1 of the crystalline lens (the inner side from the anterior capsule AP1) and is not irradiated with a laser beam so as not to damage the capsule of the crystalline lens due to the laser beam. For example, the margin is set to be 50 μm to 1000 μm. Here, the margin is 500 μM. As the margin display section 441 is operated, the increase/decrease switch (not illustrated) is displayed. The margin can be changed by the increase/decrease switch. The margin displayed in the margin display section 441 is stored in the RAM 103.

A region G1 showing the surgical operation site is displayed in the tomographic image displaying region 440. The control unit 100 performs image processing with respect to the image data forming the tomographic image, thereby obtaining the region indicating the surgical operation site (hereinafter, abbreviated as the region G1) G1. The control unit 100 emphasizes the region corresponding to the region G1 to display on the tomographic image.

In the tomographic image, the control unit 100 detects a position of the anterior capsule AP1 of the crystalline lens LE1, a position of the posterior capsule PP1 of the crystalline lens LE1, and the iris IR which is in the front of the peripheral portion of the anterior capsule AP1. The control unit 100 determines a region between the anterior capsule AP1 and the posterior capsule PP1 based on the margin stored in the memory 71, and determines a region excluding a place (a region at the rear from the iris IR) where the iris IR superposes the anterior capsule AP1. In this case, the control unit 100 does not set the margin to the position corresponding to the circle C1. Moreover, the control unit 100 displays the margin region M1 in the crystalline lens LE1 (inside thereof). The control unit 100 sets the region M1 as much as the margin at the inner side from the anterior capsule AP1, and does not set the margin for the region corresponding to the circle C1. Moreover, the control unit 100 sets the region M1 as much as the margin on the front side from the posterior capsule PP1.

The region G1 can be changed (fine adjustment) by an operation of the practitioner. Lines of the region G1 are configured to be freely changeable. The practitioner can change the shape of the region G1 by touching and dragging the lines of the region G1. In this case, the control unit 100 does not change laser irradiation the region G1 exceeding the margin. In other words, the control unit 100 does not allow the setting of the region G1 to be within the margin region. If a practitioner attempts to set the laser irradiation the region G1 exceeding the margin, the control unit 100 may control a buzzer (not illustrated) so as to warn the practitioner, thereby not receiving the change of the region G1.

In the surgical operation condition display portion 450, for example, an irradiation position of a laser beam for the cornea incision may be set in accordance with an operation of the practitioner. For example, descriptions will be given based on FIG. 14 regarding a case of setting the irradiation position for the cornea incision. Firstly, the practitioner selects a position for performing the cornea incision from the frontal image of the anterior chamber of a patient captured by the front surface observation unit 75. For example, the practitioner selects a portion of the cornea in the vicinity of the sclera away from the corneal apex, from the frontal image of the anterior chamber. An operation unit 400 receives an operation from the practitioner, thereby transmitting an operational signal to the control unit 100. As the operational signal is received from the operation unit 400, the control unit 100 causes the incision mark J to be displayed in a position of the anterior chamber image selected by the practitioner. Moreover, the control section 100 may cause a shape of the incision pattern K stored in the RAM 103 and the like corresponding to the selection made by the practitioner to be displayed in the tomographic image of the tomographic image displaying region 440. The practitioner may check the position of the incision pattern K displayed in the tomographic image displaying region 440, thereby changing the position for performing the incision. For example, when the incision pattern K is displayed on the sclera, the practitioner may change the setting so as to cause the display position of the incision pattern K to be on the cornea by operating the operation unit 400. For example, the incision pattern K may be moved by a dragging operation. The control unit 100 may record the change of the cornea incision position in the RAM 103 and the like by receiving an operational signal from the operation unit 400. The control unit 100 may change or edit the irradiation pattern F for the cornea incision based on the operational signal from the operation unit 400 by the practitioner. For example, the control unit 100 may edit the angle, the length, and the like for the incision.

As the switch 422 is operated, information (coordinate information in the image) of the circle C1 and the region G1 is stored in the RAM 103. The information of the regions G1 and M1 is two-dimensional information, but the control unit 100 converts the region G1 into three-dimensional positional information for the surgical operation regarding the surgical operation region, thereby storing the information in the RAM 103. For example, the control unit 100 rotates the region G1 having the central axis (here, an axis passing the center of the pupil obtained from the iris IR) of the crystalline lens LE1 as a rotational axis so as to interpolate the tomographic image in a direction where an image is not captured, thereby obtaining information having a three-dimensional value regarding the surgical operation region. Otherwise, the surgical operation region set on the multiple tomographic images is interpolated by interpolation algorithm such as spline interpolation, thereby obtaining the three-dimensional information. Accordingly, information of the surgical operation site set by using the tomographic image is generated, thereby being stored in the RAM 103. As a method of irradiation planning, the method disclosed in JP-A-2013-248304 may be utilized.

As the planning for the docking steps, for example, the control unit 100 may obtain the collimation axis or the structural axis (also referred to as an optical axis) of the eyeball from the OCT image of the patient's eye E. Accordingly, the lighting position of the fixation light in which the optical axis of the apparatus, and the collimation axis of the patient's eye E, and the structural axis of the eyeball coincide with one another can be obtained in advance. For example, when performing the cornea irradiation such as the LASIK surgical operation, it is preferable that the collimation axis of the eyeball and the optical axis of the apparatus coincide with each other. Therefore, the lighting position of the fixation light can be controlled so as to project the fixation light from the optical axis direction of the apparatus. Moreover, for example, when performing the crystalline lens irradiation such as a cataract operation, it is preferable that the structural axis of the eyeball (the optical axis of the eyeball) and the optical axis of the apparatus coincide with each other. Therefore, the lighting position of the fixation light may be controlled in a tilted manner with respect to the optical axis direction of the apparatus.

In this manner, if the relationship between the structural axis and the collimation axis of the patient's eye E is obtained in advance, and the lighting position of the fixation light is calculated, the eyeball can be properly fixed without spending dead time during the surgical operation.

<Flow of Surgical Operation and Control Operation>

Next, a control operation for the flow of a surgical operation and the apparatus 1 will be described with reference to FIG. 15. In the followings, descriptions will be give regarding a case where the surgical operation starts after setting (Step 1) the conditions of a surgical operation using an observation image of the patient's eye E before the surgical operation.

<Intraoperative Operation Method>

Firstly, the practitioner attaches the eyeball fixing unit 280 to the connection portion 250. The practitioner causes the eyeball fixing unit 280 to fit the connection portion 250. Next, the practitioner presses the suctioning start button of the operation portion. As the suctioning start button is pressed, the control unit 100 transmits an operational signal to the suctioning device. The suctioning device performs suctioning of air in the space R formed between the connection portion 250 and the concave portion 283 based on the operational signal transmitted from the control unit 100. If suctioning of air in the space R is performed, a negative pressure is generated inside the space R. Accordingly, the eyeball fixing unit 280 is adsorbed to the connection portion 250.

Next, the practitioner attaches the interface unit 50 to the holder 52 of the irradiation end unit 42. The practitioner operates the operation portion, thereby transmitting a signal to start docking (the eyeball fixing) to the control unit 100. The control unit 100 receives the operational signal from the operation portion by the practitioner, thereby starting the automatic docking.

<Automatic Docking>

Hereinafter, a control operation will be described regarding docking (Step 2) of the present example. The apparatus of the present example can be automatically docked with the patient's eye E. Accordingly, time taken for docking can be shortened, and thus, docking can be performed without a burden.

<XY-Alignment>

The control unit 100 may perform positioning (the XY-alignment) the optical axis L1 of the laser irradiation unit 300 with respect to the patient's eye E. For example, the control unit 100 moves the first movement unit in the XY-direction based on the position of the patient's eye detected by the alignment detection units (for example, the observation optical system 70 and the control unit 100).

The alignment detection unit is used to detect a position of the eye E in a lateral direction (the XY-direction) with respect to the apparatus. For example, the alignment detection unit may detect the position of the patient's eye E in the XY-direction by combining an illumination optical system and the observation optical system 70. For example, the alignment detection unit may detect the position of the patient's eye E in the XY-direction by performing image processing with an image of the anterior chamber captured by the observation optical system 70. For example, a position of the cornea reflection image of illumination light projected in the image of the anterior chamber may be detected. Alignment may be performed so as to move the position of the cornea reflection image to a predetermined position in the screen.

For example, the alignment detection unit may detect a position of the patient's eye E in the lateral direction from the tomographic image with respect to the apparatus. In this case, for example, a cornea flare image may be detected from the tomographic image. In more details, since measurement light is intensively reflected on a corneal surface vertical to the tomographic image capturing unit 71, intensity of the interference signal increases. Therefore, a line parallel to the measurement optical axis is generated in the vicinity of the apex of the cornea in the image. The line is referred to as the cornea flare image. The control unit 100 may detect the cornea flare image through image processing and control the first movement unit so as to cause the line of light to come to the center of the image, thereby performing alignment in the XY-direction.

Moreover, three-dimensional shape data may be established based on the tomographic image, thereby detecting the positional relationship between the apparatus and the patient's eye E from the shape information. For example, the control unit 100 establishes the three-dimensional shape data of the iris based on the tomographic image. The control unit 100 may calculate the center of the pupil from the three-dimensional shape data of the iris, thereby performing the XY-alignment by matching the center of the pupil and the optical center of the apparatus. In this manner, the control unit 100 may automatically perform the alignment of the XY-direction while detecting the position of the patient's eye E through the tomographic image or the anterior chamber image.

<Z-Direction Alignment>

As the XY-alignment is completed, the control unit 100 may control the drive section 12, thereby performing the alignment in the Z-direction by moving the irradiation end unit 42 toward the patient's eye E. As a result, an interface unit 59, the eyeball fixing unit 280, and the second movement unit 200 are integrally moved together with the irradiation end unit 42.

For example, the control unit 100 may detect the position of the patient's eye E in the optical axis direction (the Z-direction) with respect to the apparatus 1. Then, the first movement unit 10 may be moved in the Z-axis direction based on the detected position of the patient's eye E, thereby arranging the laser irradiation unit 300 at a predetermined position with respect to the patient's eye E. For example, the control unit 100 may detect the position of the patient's eye E in the optical axis direction by using the front surface observation unit 75. In more details, a state of the luminescent spot of the illumination light source projected on the frontal image of the patient's eye E captured by the front surface observation unit 75 may be detected. For example, the position of the patient's eye E may be detected in accordance with a senile state of the luminescent spot. For example, when the position of the patient's eye E is away from the predetermined position with respect to an irradiation unit 42, the luminescent spot detected by the light receiving element 76 is senile (refer to FIG. 18A). In this case, a light receiving range from the luminescent spot detected by the light receiving element increases, and intensity thereof becomes weak. Therefore, the senile state of the luminescent spot and the positional relationship of the patient's eye E is measured in advance, and thus, the position of the patient's eye E in the optical axis direction can be detected. The control unit 100 may detect not only the luminescent spot but also the senile state of the anterior chamber image, thereby detecting the position of the patient's eye E in the optical axis direction.

The second detection unit may detect the position of the patient's eye E in the optical axis direction through the tomographic image of the patient's eye E captured by the tomographic image capturing unit 71. For example, if the optical path length of reference light of the tomographic image capturing unit 71 is constant, the image capturing region captured in the tomographic image is constant. Therefore, it is possible to obtain the position of the patient's eye E from the position of the tomographic image acquired by the detector 717. If the optical path length of reference light of the reference optical system is changeable, for example, the position of the patient's eye E in the optical axis direction may be detected based on a position of the cover glass 51 projected in the tomographic image.

<Fixation Induction>

As the position of the laser irradiation unit 300 is arranged at a predetermined position with respect to the patient's eye E, the control unit 100 may control the fixation induction unit 120, thereby starting fixation induction of the patient's eye E. For example, the control unit 100 detects a tilt of the eyeball by the detection unit. Then, the control unit 100 may control the collimation axis induction of the fixation induction unit 120 based on a tilt state of the eyeball. For example, as the tilt detection unit, the tomographic image capturing unit 71 may be used. For example, based on the tomographic image captured by the tomographic image capturing unit 71, the tilt of the eyeball may be detected. For example, the control unit 100 may establish the three-dimensional shape data based on the tomographic image having two or more tomographic images (preferably three or more tomographic images), thereby obtaining the tilt from the shape information. For example, the tilt detection unit may detect directions of lines passing through the center of the curvature of the anterior capsule and the center of the curvature of the posterior capsule of the crystalline lens detected through the tomographic image as the optical axis S1 of the eyeball. For example, the tilt detection unit may detect directions of lines passing through the center of the curvature of the front surface and the center of the curvature of the rear surface of the cornea detected through the tomographic image as the optical axis S1 (the structural axis) of the eyeball. For example, the tilt detection unit may detect a tilt state of the optical axis S1, the collimation axis S2, and the like of the eyeball by degree with respect to the optical axis L1 of the apparatus. As the tilt detection unit, an anterior chamber tomographic image capturing apparatus by Scheimflug's optical system may be used.

Figure 16A:
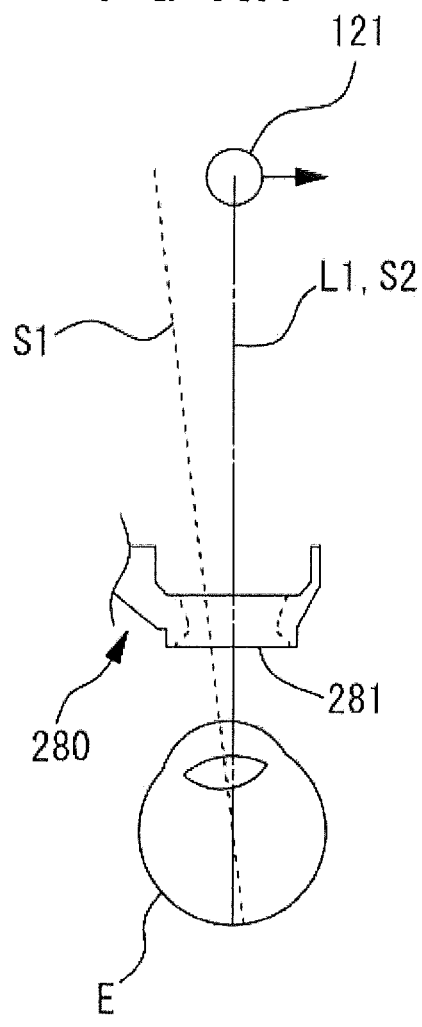
FIGS. 16A and 16B are diagrams for illustrating an operation of a fixation induction unit.
Figure 16B:
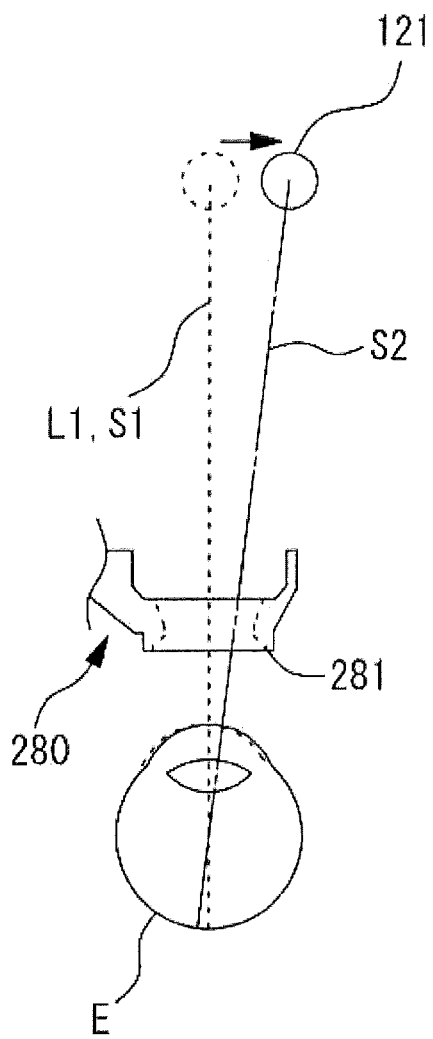

The control unit 100 controls the collimation axis induction of the fixation induction unit 120 based on a tilt of the patient's eye E detected by the tilt detection unit. For example, as shown in FIGS. 16A and 16B, the control unit 100 controls the fixation induction unit 120 so as to cause the optical axis S1 or the collimation axis S2 to be at the appropriate position with respect to the optical axis L1 of the apparatus, thereby inducing the collimation axis S2. For example, when irradiating the crystalline lens with a laser, as illustrated in FIG. 16B, it is preferable that the optical axis S1 of the eyeball and the optical axis L1 of the apparatus coincide with each other. In such a case, the fixation induction unit 120 is controlled to obliquely project the fixation light to the optical axis L1 of the apparatus. For example, when irradiating the cornea with laser, as illustrated in FIG. 16A, it is preferable that the collimation axis S2 and the optical axis L1 of the apparatus coincide with each other. In such a case, the fixation induction unit 120 is controlled to project the fixation light from the direction of the optical axis L1 of the apparatus.

<Revision of Alignment Through Fixation Induction>

As the position of the fixation light is moved by the fixation induction unit 120, there is a case where the position of the luminescent spot of the cornea formed in the cornea of the patient's eye E is misaligned. In this case, the control unit 100 may revise the alignment position as much as the misalignment caused by a movement of the fixation light. For example, fixation induction is controlled based on the intraoperative detection result of the tilt of the eyeball captured by the tomographic image capturing unit 71. At this time, there is a case where the luminescent spot is misaligned due to the fixation induction. The control unit 100 may control the first movement unit 10 based on the position of the image of the luminescent spot of the cornea captured by the observation optical system 70, thereby performing the optimal alignment in the XY-direction even after the fixation induction.

Figure 17A:
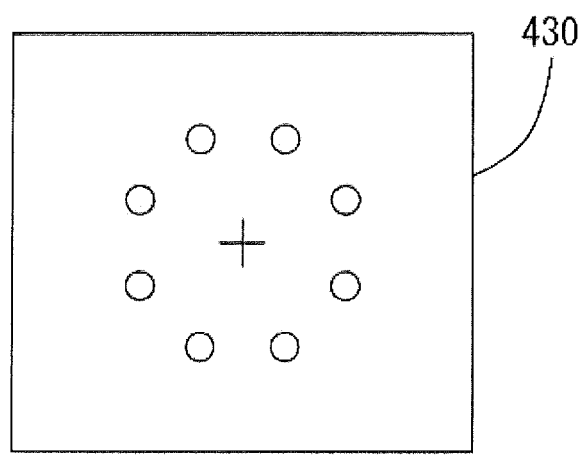
FIGS. 17A and 17B are diagrams for illustrating a portion of an alignment operation of the present example.
Figure 17B:
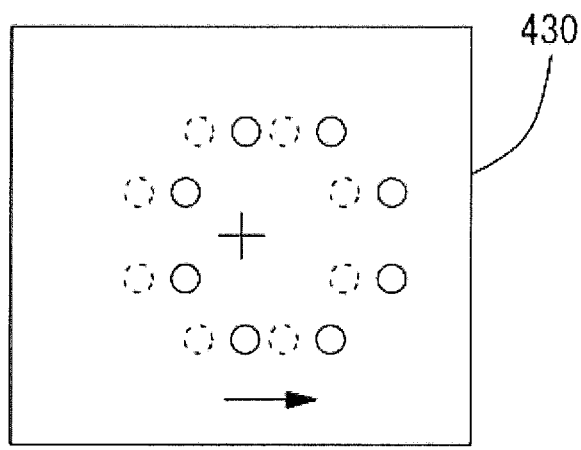

For example, as shown in FIGS. 17A and 17B, in the present example, the luminescent spot generated in the cornea of the patient's eye E is formed based on a point of the cornea of the patient's eye E on a side closest to the apparatus (the irradiation end unit side). When the position of fixation is switched by the fixation induction unit 120, there is a case where the position of the luminescent spot of the cornea is misaligned in the lateral direction. The reason is that the position of the point of the cornea on the side closest to the apparatus has moved. Therefore, when the lighting position of the fixation light is switched due to fixation induction, for example, the control unit 100 may detect misalignment in the XY-direction by the first detection unit. Then, the control unit may perform alignment in the XY-direction again by moving the first movement unit 10 based on the detected misalignment. Even though the luminescent spot is not used, for example, an misalignment amount may be obtained through a shape of the patient's eye E detected through the tomographic image, thereby achieving alignment in the XY-direction.

<Automatic Focusing and Automatic Alignment>

In the present example, while causing the frontal image to be in focus by the focal adjustment unit, the patient's eye E may be subjected to auto focusing. As the frontal image is in focus, the luminescent spot projected in the frontal image becomes obscure. The control unit 100 may perform an automatic focal adjustment by using the luminescent spot projected on the frontal image.

Figure 18A:
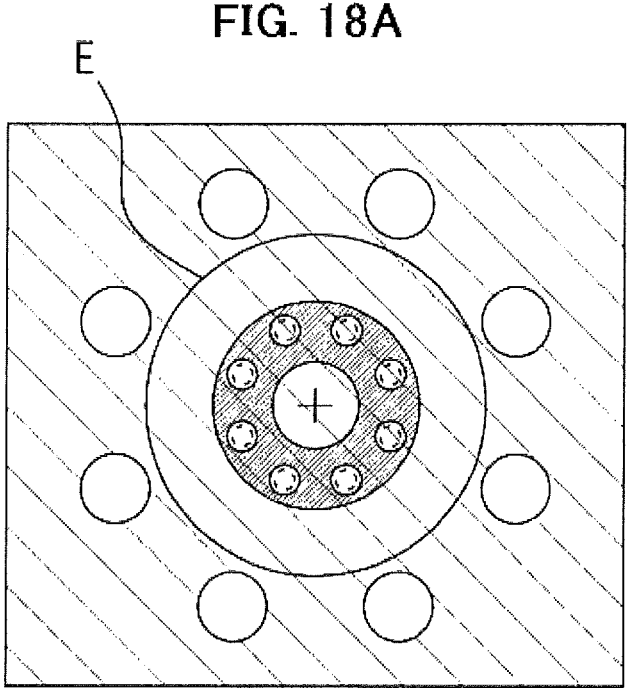
FIGS. 18A and 18B are diagrams for illustrating alignment detection of the present example.
Figure 18B:
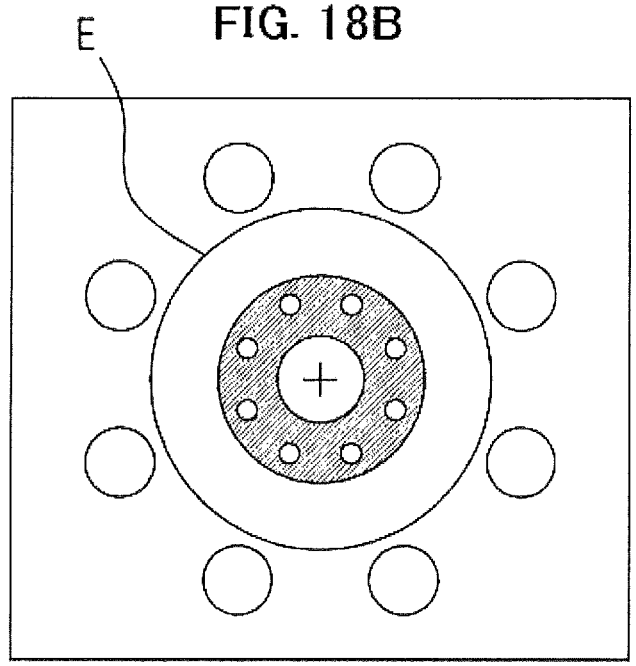

For example, as illustrated in FIG. 18A, in a state where the frontal image is out of focus, the entire image is senile, and there is a possibility of significant error when the luminescent spot is detected. Therefore, the control unit 100 controls the focal adjustment unit 80 and automatically adjusts focus of the frontal image of the anterior chamber. Accordingly, it is possible to favorably detect the luminescent spot of the frontal image of the anterior chamber (refer to FIG. 18B).

The control unit 100 detects the position of the luminescent spot from the frontal image in focus with respect to the luminescent spot of the patient's eye E. Then, the irradiation end unit 42 is aligned based on a position of the detected luminescent spot. For example, the control unit 100 determines the center of the pupil from the position of the luminescent spot, and moves the irradiation end unit 42 so as to cause the determined center of the pupil to be arranged in the center of the frontal image, thereby performing the alignment.

As described above, when performing the alignment, focusing is performed on the luminescent spot, and thus, the position of the luminescent spot can be favorably detected. Accordingly, the control unit 100 is likely to perform the alignment based on the position of the focused luminescent spot.

The focal adjustment unit 80 does not have to cause the frontal image capturing unit 75 to be in focus with the luminescent spot of the cornea. For example, focusing may be performed on the cornea, the corneal limbus, the iris, and the crystalline lens.

In the above description, alignment is performed by using the luminescent spot of the cornea. However, alignment is not limited thereto. For example, the control unit 100 may determine the center of the pupil of the patient's eye E by detecting the pupil, the corneal limbus, and the like from the frontal image captured by the frontal image capturing unit 75, thereby performing the alignment.

<Reflection of Contents of Planning>

As the eyeball fixing (Step 2) is completed, the control unit 100 acquires the observation image of the patient's eye E by using the observation optical system 70 (Step 4). For example, the control unit 100 may acquire the tomographic image of the patient's eye E by using the tomographic image capturing unit 71. The control unit 100 causes the observation image captured before the surgical operation to be associated with the intraoperative observation image captured by the observation optical system 70 (Step 5). Accordingly, the contents of the planning set before the surgical operation can be associated with the intraoperative observation image. Therefore, the control unit 100 can perform the surgical operation in accordance with the surgical operation set before the surgical operation.

There is a possibility that the observation image in a state of not being docked to the patient's eye E captured by an external observation apparatus before the surgical operation does not coincide with the observation image after being docked to the patient's eye E captured by the observation optical system 70. For example, the cornea, the iris, the crystalline lens, and the like are deformed. For example, the tilt of the crystalline lens changes. For example, in a case where the preoperative image is captured in a state of standing and the intraoperative image is captured in a state of lying, there is a possibility of a change in the shape of the patient's eye E. For example, since the eyeball is fixed by the eyeball fixing unit during the surgical operation, there is a possibility of a change in the shape of the patient's eye E.

As described above, when the shapes of the eyeball image respectively acquired before and during the surgical operation does not coincide with each other, the control unit 100 may revise the contents of the planning set based on the preoperative observation image into the contents appropriate for the intraoperative observation image (Step 6). For example, as shown in FIGS. 19A and 19B, firstly the control unit 100 detects at least one item of the shape information such as the cornea shape, the iris shape, the crystalline lens shape, the angulus iridocornealis shape out of the tomographic image. Subsequently, the control unit 100 causes the preoperative observation image to be associated with the intraoperative observation image. Accordingly, the surgical operation conditions set based on the preoperative image are associated with the intraoperative image. The control unit 100 can calculate the position of the patient's eye E associated with the apparatus, from the position of the intraoperative image. Therefore, the control unit 100 can irradiate the patient's eye E with a laser beam following after the surgical operation region associated with the intraoperative image. In other words, the control unit 100 can treat the patient's eye E under the surgical operation condition set through the planning.

For example, the control unit 100 causes the preoperative image and the intraoperative image to be associated with each other based on the detected shape information. For example, the control unit 100 acquires the shape of the iris with respect to the images respectively before and during the surgical operation. Then, the control unit 100 calculates the plane D1 including the angulus iridocornealis (a base portion of the iris and the cornea), and the line D2 which is perpendicular to the plane thereof and passes through the center of the pupil, with respect to the images respectively (refer to FIGS. 19A and 19B).

For example, the control unit 100 may cause the preoperative observation image and the intraoperative observation image to be associated with each other so as to make the plane D1 and the line D2 individually coincide with each other. The control unit 100 may cause the preoperative image and the intraoperative image to be associated with each other so as to make the line D2 and the apex of the anterior capsule of the crystalline lens to coincide with each other.

The control unit 100 may revise the contents of the planning set based on the preoperative observation image so as to be appropriate for the intraoperative image by causing the preoperative observation image and the intraoperative observation image to be associated with each other.

For example, as shown in FIGS. 20A and 20B, as a result of associating the contents of the preoperative planning to the intraoperative observation image, depending on changes in the preoperative eye shape and the intraoperative eye shape, there is a case where the contents of the preoperative planning is not appropriate in the intraoperative observation image. In such a case, the control unit 100 may revise the contents of preoperative planning to be appropriate for intraoperative contents. For example, it is assumed that there is an occurrence of a change in the thickness of the crystalline lens between the preoperative contents and the intraoperative contents. In this case, the region G1 for irradiation of a laser may be revised in accordance with the change amount in the thickness of the crystalline lens. For example, when the thickness of the crystalline lens becomes thicker by 0.5 mm, 0.5 mm of the crystalline lens remains in surplus without being irradiated with a laser with respect to the preset margin (refer to FIG. 20A). Therefore, the control unit 100 does not have to cause the region G1 for laser irradiation to be thicker by 0.5 mm (refer to FIG. 20B). For example, the control unit 100 may revise the irradiation region of a laser to be the region A2 from the region A1 within a range of the set margin with respect to the anterior capsule and the posterior capsule.

For example, the control unit may revise a position for the cornea incision which is set in the preoperative planning according to a shape of the cornea during the operation. For example, the control unit 100 may revise a position for the cornea incision according to a change in a shape of the cornea during the operation and before the operation. For example, it is assumed that the contents of the preoperative planning are associated with the intraoperative observation image. As a result, the incision pattern K is displayed on the sclera. In this case, the control unit may detect a boundary between the cornea and the sclera from the intraoperative observation image. Then, the control unit may revise a position of the incision pattern K to a position on the cornea side further from the detected boundary.

The control unit 100 may correct the laser irradiation region G1 even in a mydriasis condition. For example, when the pupil is largely open during the operation as compared to the preoperative state, the control unit 100 may revise the laser irradiation region G1 to the region A2 according to a diameter of the pupil.

As described above, it is possible to more smoothly perform the surgical operation by correcting operative conditions set for the preoperative image based on the intraoperative image. For example, when a shape of the preoperative eyeball and a shape of the intraoperative eyeball are different from each other, there is a possibility that the surgical operation cannot be performed according to the operative conditions scheduled during the planning. In this case, the contents of planning can be corrected, thereby saving time and effort to reschedule the planning from the beginning.

The correcting contents of planning may be automatically performed by the control unit 100, or may be manually performed by a practitioner. For example, a configuration may be adopted in which the control unit 100 automatically corrects the contents of planning, and in which after the practitioner checks the corrected contents of planning, the practitioner can manually correct the contents of planning by operating an operation unit if further correction is needed.

The planning may be performed by using another apparatus (filing system for displaying the tomographic image or the like). In this case, data of the planning is read by the surgical operation apparatus.

<Modification Example of OCT Overall Image Capturing>

For example, the apparatus 1 may include the optical path length adjustment unit 740 (refer to FIGS. 21A and 21B). The optical path length adjustment unit 740 may adjust the optical path length of the reference light by moving the reference mirror of the reference optical system. Accordingly, a configuration may be adopted in which the image capturing region of the tomographic image capturing unit 71 can be changed. For example, the optical path length adjustment unit 740 may move at least one reference mirror disposed in the reference optical system by driving of the driving section. For example, the optical path length adjustment unit 740 moves the second reference mirror 731 disposed in the second reference optical system 715.

The optical path length adjustment unit 740 can change the optical path length of the second reference optical system 715 by moving the second reference mirror 731. If the optical path length of the second reference optical system 715 is changed, the position of the tomographic image acquired by the detector 717 is changed.

For example, as shown in FIGS. 21A and 21B, the second reference mirror 731 is configured to be arranged at the reference position A. In this case, the tomographic image is acquired for a region located far from the eyeball fixing unit 280. Thereafter, for example, the drive section 741 moves the second reference mirror 731 to the position B, and the optical path length of the second reference optical system 715 is shortened. Accordingly, when the second reference light of the second reference optical system 715 and the measurement light are synthesized, the tomographic image is acquired for a region close to the suctioning ring 281. For example, when the second reference mirror 731 is arranged at the position B, the tomographic image is acquired for a region located far from the suctioning ring 281 by 10 mm back and forth.

As described above, the optical path length adjustment unit 740 moves the second reference mirror 731. In this manner, it is possible to acquire the tomographic image of the patient's eye E in a wide range from a region located far from the suctioning ring 281 to a region close to the suctioning ring 281.

The image capturing region of the tomographic image can be moved by changing the optical path length of the second reference optical path which passes through the second reference optical system. Accordingly, when the cornea is moved to the irradiation end unit 42, the image capturing region of the tomographic image capturing unit 71 can be changed according to a motion of the cornea. Accordingly, when the eyeball fixing unit 280 moves close to the patient's eye, it is possible to observe a state where the eyeball fixing unit moves close to the patient's eye E.

The optical path length adjustment unit 740 may move the second reference mirror, based on a signal detected by the observation optical system 70. For example, the optical path length adjustment unit 740 may move the second reference mirror 731, based on the positional information of the patient's eye E which is acquired by analyzing the tomographic image. Accordingly, the image capturing region of the tomographic image capturing unit 71 can be aligned with the patient's eye E.

For example, the optical path length adjustment unit may move the second reference mirror 731 in conjunction with a movement amount of the apparatus. For example, the control unit 100 measures a driving amount of the drive section 12 which drives first movement unit. Then, the second reference mirror 731 may be moved according to the measured driving amount of the drive section 12. Accordingly, even if the position of the patient's eye E is not detected, the image capturing region of the tomographic image capturing unit 71 can be aligned with the patient's eye E.

In the above description, the optical path length adjustment unit 740 is configured to move the second reference mirror 731, but the configuration is not limited thereto. For example, a configuration may be adopted in which the first reference mirror 721 can be moved, or in which the first reference mirror 721 and the second reference mirror can be moved.

A position of each optical member may be automatically adjusted so that the optical path adjustment unit is located at a predetermined position and the tomographic image capturing unit 71 is allowed to have a predetermined arrangement corresponding to the anterior chamber capture mode.

The apparatus of the present disclosure provides the following aspects:

(1) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a movement unit that is provided so as to move an eyeball fixing unit for fixing the patient's eye onto an optical axis of a laser irradiation unit, toward the patient's eye;

Eye detection means for detecting the patient's eye before being fixed by the eyeball fixing unit based on a captured image captured by an imaging optical system for capturing an image of the patient's eye; and Control means for controlling driving of a drive section based on a detection signal from the eye detection means and automatically moving the eyeball fixing unit with respect to the patient's eye before being fixed by the eyeball fixing unit.

(2) The ophthalmic laser surgery apparatus according to (1), wherein the eye detection means includes at least any one of alignment detection means for detecting an alignment state of the patient's eye with respect to the irradiation optical system based on the captured image, and tilt detection means for detecting a tilt state of the patient's eye with respect to the irradiation optical system based on the captured image.

(3) The ophthalmic laser surgery apparatus according to (2), wherein the control means controls driving of the drive section and causes the eyeball fixing unit to automatically adhere to the patient's eye when it is determined that at least any one of the alignment state and the tilt state is appropriate through a detection result of the eye detection means.

(4) The ophthalmic laser surgery apparatus, wherein the movement unit is a movement unit provided to move the eyeball fixing unit integrally with the irradiation optical system, wherein the ophthalmic laser surgery apparatus according to any one of (1) to (3) further includes fixation induction means for moving a presentation position of a fixation target presented to the patient's eye and inducing a fixation direction of the patient's eye, and wherein after performing automatic positioning by controlling the drive section so as to cause the patient's eye and the irradiation optical system to have a predetermined positional relationship based on a detection result of an alignment state of the patient's eye with respect to the irradiation optical system performed by the eye detection means, the control means controls the fixation induction means and automatically presents the fixation target so as to cause the optical axis of irradiation and a tilt of the patient's eye to have a predetermined relationship, and controls the drive section again so as to automatically move the movement unit to be in the predetermined positional relationship again with respect to misalignment generated by moving the presentation position of the fixation target.

(5) The ophthalmic laser surgery apparatus according to any one of (1) to (4), wherein the control means controls the fixation induction means based on the detection result of the tilt state of the patient's eye with respect to the irradiation optical system performed by the eye detection means, and wherein the presentation position of the fixation target is automatically moved.

(6) The ophthalmic laser surgery apparatus, further comprising:

an alignment projection optical system that projects alignment light toward the patient's eye, wherein the alignment detection means according to (2) or (3) detects misalignment of the laser irradiation unit with respect to the patient's eye by causing a light receiving element to receive reflected light from the anterior chamber generated by the alignment light.

(7) The ophthalmic laser surgery apparatus according to (1) or (2), wherein the alignment detection means according to (2) or (3) acquires a tomographic image of the patient's eye, acquires a shape of a feature site of the patient's eye from the acquired tomographic image, and detects misalignment of the laser irradiation unit with respect to the patient's eye.

(8)

The ophthalmic laser surgery apparatus according to (4), wherein the eyeball fixing unit is an eyeball fixing unit which has a ring-shaped suctioning ring brought into contact with the patient's eye and performs suctioning and fixing with the patient's eye on the optical axis of irradiation, wherein the movement unit can cause the irradiation optical system and the eyeball fixing unit to be integrally movable, wherein the control means controls driving of the drive section so as to move the eyeball fixing unit to a position where the patient's eye and the suctioning ring are brought into contact with each other, wherein when the eyeball fixing unit is moved to the position where the patient's eye and the suctioning ring are brought into contact with each other, the control means controls the fixation induction means and moves the presentation position of the fixation target presented to the patient's eye in order to cause an optical axis of irradiation of the laser irradiation unit and an optical axis of the patient's eye to coincide with each other.

(9) The ophthalmic laser surgery apparatus according to (8), wherein after controlling the drive section so as to cause the patient's eye and the suctioning ring to be at a position to be in contact with each other with respect to misalignment generated by moving the presentation position of the fixation target, the control means performs suctioning and fixing with the patient's eye by using the eyeball fixing unit.

(10) The ophthalmic laser surgery apparatus according to (4), wherein the eyeball fixing unit is an eyeball fixing unit which has a ring-shaped suctioning ring brought into contact with the patient's eye and performs suctioning and fixing with the patient's eye on the optical axis of irradiation, and wherein the control means controls the fixation induction means so as to move the presentation position of the fixation light in order to revise deviation of the optical axis of the fixation target refracted by liquid which is injected into the suctioning ring.

(11) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation optical system by driving the drive section;

eye detection means for detecting the patient's eye before being fixed by an eyeball fixing unit based on a captured image captured by an imaging optical system for capturing an image of the patient's eye; and fixation induction means for moving a presentation position of a fixation target to be presented to the patient's eye and inducing a fixation direction of the patient's eye, wherein after performing automatic positioning by controlling the drive section so as to cause the patient's eye and the irradiation optical system to be in a predetermined positional relationship based on a detection result of the eye detection means, control means controls the fixation induction means so as to automatically present the fixation target for causing an optical axis of irradiation and an optical axis of the patient's eye to coincide with each other and controls the drive section again so as to automatically move the movement unit to be in the predetermined positional relationship again with respect to misalignment generated by moving the presentation position of the fixation target.

(12) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation end unit by driving the drive section;

eye detection means for detecting the patient's eye before being fixed by an eyeball fixing unit based on a captured image captured by an imaging optical system for capturing an image of the patient's eye;

fixation induction means for moving a presentation position of a fixation target to be presented to the patient's eye and inducing a fixation direction of the patient's eye; and control means for controlling the fixation induction means so as to automatically present the fixation target for causing an optical axis of irradiation and an optical axis of the patient's eye to coincide with each other and controlling the drive section again so as to automatically move the movement unit to be in the predetermined positional relationship again with respect to misalignment generated by moving the presentation position of the fixation target after performing automatic positioning by controlling the drive section so as to cause the patient's eye and the irradiation optical system to be in a predetermined positional relationship based on a detection result of the eye detection means.

(13) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move at least a portion of the irradiation end unit by driving the drive section;

eye detection means for detecting the patient's eye before being fixed by an eyeball fixing unit based on a captured image captured by an imaging optical system for capturing an image of the patient's eye;

an observation optical system that has the light receiving element and is provided in a laser irradiation unit in order to capture an anterior chamber observation image of the patient's eye by using the light receiving element; and focal adjustment means for adjusting focus of the observation optical system with respect to the patient's eye, wherein the focal adjustment means can revise focus deviation of the observation optical system caused by driving of the movement unit, wherein the eye detection means detects an alignment state of the patient's eye with respect to the irradiation optical system by using the anterior chamber observation image which is revised by the focal adjustment means, and wherein the ophthalmic laser surgery apparatus also controls the drive section based on an alignment detection result performed by the eye detection means and moves at least a portion of the irradiation end unit with respect to the patient's eye.

(14) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit containing the objective lens, includes at least a portion of the irradiation optical system, and optically guides the laser beam to the patient's eye;

a movement unit that includes a drive section and is provided to move the irradiation end unit including the objective lens toward the patient's eye by driving the drive section;

an observation optical system that is provided in the irradiation end unit so as to observe the anterior chamber of the patient's eye; and focal adjustment means for adjusting focus of the observation optical system with respect to the anterior chamber.

(15) The ophthalmic laser surgery apparatus according to (14), wherein the movement unit can move the irradiation end unit between a first position where the irradiation end unit is arranged when irradiating the patient's eye with a laser and a second position which is a position farther away from the patient's eye than the first position and at which the irradiation end unit is positioned before the patient's eye is fixed by the eyeball fixing unit, and wherein the focal adjustment means is focal adjustment means for individually adjusting focus of the observation optical system with respect to the anterior chamber in accordance with a distance of the irradiation end unit or the objective lens at the first position and the second position with respect to the patient's eye.

(16) The ophthalmic laser surgery apparatus according to (14) or (15), wherein the focal adjustment means includes the drive section which is arranged in the observation optical system so in order to adjust focus of the observation optical system and drives a member for adjusting focus of the observation optical system, and control means for controlling the drive section and adjusting focus of the observation optical system with respect to the anterior chamber.

(17) The ophthalmic laser surgery apparatus according to (14) or (15), further comprising:

detection means for detecting a distance of the irradiation end unit or the objective lens to the patient's eye generated by the movement unit, wherein the control means controls the drive section in accordance with a detection result of the detection means so as to adjust focus of the observation optical system with respect to the anterior chamber in accordance with the distance of the irradiation end unit or the objective lens to the patient's eye generated by the movement unit.

(18) The ophthalmic laser surgery apparatus according to any one of (15) to (17), further comprising:

alignment detection means for detecting an alignment state of the irradiation end unit with respect to the patient's eye based on a light receiving signal from a light receiving element which is arranged in the observation optical system in a state where the irradiation end unit is arranged in the second position.

(19) The ophthalmic laser surgery apparatus according to (18), wherein a light source for emitting illumination light for forming luminescent spot on a cornea of the patient is arranged, wherein the observation optical system can capture an anterior chamber image of the patient's eye including a first cornea reflection image which is formed by illumination light passing through the outside of an interface having a light-transmitting optical member covering at least a portion of the cornea of the patient's eye, and a second cornea reflection image which is formed by illumination light passing through the inside of the interface, and wherein the alignment detection means detect the position of the patient's eye based on at least one of the first cornea reflection image and the second cornea reflection image captured by the observation optical system.

(19) An ophthalmic laser surgery apparatus which includes an irradiation optical system irradiating a patient's eye with a laser beam emitted from a laser source and including an objective lens for concentrating the laser beam on a tissue of the patient's eye, and treats the patient's eye by using the laser beam, the apparatus comprising:

a delivery unit that includes an irradiation end unit in which a light source for performing irradiation with illumination light is arranged so as to form the luminescent spot on the cornea of the patient's eye and which contains the objective lens, includes at least a portion of the irradiation optical system, and optically guides the laser beam to the patient's eye;

a movement unit that includes a drive section and is provided to move the irradiation end unit including the objective lens toward the patient's eye by driving the drive section; and an observation optical system that is provided in the irradiation end unit so as to observe the anterior chamber of the patient's eye, wherein the observation optical system can capture an anterior chamber image of the patient's eye including a first cornea reflection image which is formed by illumination light passing through the outside of an interface having a light-transmitting optical member covering at least a portion of the cornea of the patient's eye, and a second cornea reflection image which is formed by illumination light passing through the inside of the interface, and wherein the ophthalmic laser surgery apparatus includes alignment detection means for detecting a position of the patient's eye based on at least one of the first cornea reflection image and the second cornea reflection image captured by the observation optical system.

(20) An ophthalmic laser surgery apparatus which includes a scanning optical system performing three-dimensional scanning with a laser beam emitted from a laser source and irradiates each target position corresponding to a preset treatment region with the laser beam so as to treat a patient's eye, the apparatus comprising:

variation information acquisition means for acquiring a first data set related to a structure of the patient's eye acquired to establish prior planning of a treatment region including the inside of a tissue of the patient's eye, and a second data set related to a structure of the patient's eye acquired when performing treatment by using the laser beam based on the planned treatment region after the planning of the treatment region is established so as to obtain variation information of the patient's eye which is at least any one of structural variation information of the patient's eye and variation information of a sight direction of the patient's eye by comparing the first data set and the second data set.

(21) The ophthalmic laser surgery apparatus according to (20), wherein the first data set is acquired based on an image captured by a first ophthalmic image capturing apparatus which is an apparatus separately installed in order to capture an image of the patient's eye in a sitting state.

(22) The ophthalmic laser surgery apparatus according to (20) or (21), further comprising:

a fixation induction unit that moves a presentation position of a fixation target presented to the patient's eye and induces a fixation direction of the patient's eye; and control means for controlling the fixation induction unit based on variation information of a sight direction of the patient's eye acquired by the variation information acquisition means and revising variation of the sight direction of the patient's eye when the first data set used in planning is acquired.

(23) The ophthalmic laser surgery apparatus according to (20) or (21), further comprising:

setting means for setting an irradiation position of the laser beam based on the treatment region which is subjected to planning based on the first data set, and the variation information of the patient's eye acquired by the variation information acquisition means.

(24) The ophthalmic laser surgery apparatus according to any one of (21) to (23), further comprising:

the fixation induction unit that moves the presentation position of the fixation target presented to the patient's eye and induces the fixation direction of the patient's eye; and control means for controlling the fixation induction unit and revising the fixation direction of the patient's eye so as to cause an optical axis of irradiation of the laser and an optical axis of the patient's eye to coincide with each other, wherein the variation information acquisition means acquires the second data set regarding a structure of the patient's eye of which the fixation direction is revised by the control means, as a second data set, and wherein the setting means sets the irradiation position of the laser beam based on the treatment region which is subjected to planning based on the first data set, and the variation information of the patient's eye acquired by the variation information acquisition means.

(25) The ophthalmic laser surgery apparatus according to any one of (21) to (24), further comprising:

the variation information acquisition means in which the first data set and the second data set are data sets individually including data related to an angulus iridocornealis structure of the patient's eye, and the variation information acquisition means compares data related to the angulus iridocornealis structure in the first data set and data related to the angulus iridocornealis structure in the second data set so as to acquire the variation information of the patient's eye which is at least any one of structural variation information of the patient's eye and the variation information of the sight direction of the patient's eye.

(26) The ophthalmic laser surgery apparatus according to any one of (21) to (25), wherein the first data set and the second data set are data sets individually including data related to at least any one of a cornea structure, a crystalline lens structure, and an iris structure of the patient's eye.

(27) An eyeball fixing portion movement unit used for a surgery using an ophthalmic laser surgery apparatus for treating a patient's eye by a laser beam comprising:

a suction ring; and a pipe for supply liquid to an inner side of the suction ring.

(28) The eyeball fixing portion movement unit according to (27) comprising a detachable portion which is detachable to a leading end of the ophthalmic laser surgery apparatus.

(29) The eyeball fixing portion movement unit according to (27), wherein the pipe is a pipe different from a suction pipe for sucking the patient's eye.

What is claimed is:

1. An ophthalmic laser surgery apparatus comprising:
   an irradiation optical system configured to irradiate a laser beam emitted from a laser source toward a patient's eye;
   a laser delivery optical system including:
      an irradiation end unit including at least an objective lens, and
      at least a portion of the irradiation optical system,
      the laser delivery optical system is configured to optically guide the laser beam from the irradiation optical system to the patient's eye;
   a first actuator including a first motor and configured to integrally move the irradiation end unit and an eyeball fixing unit toward the patient's eye, the eyeball fixing unit including a suction ring and being connected to the laser delivery optical system;
   a second actuator including a second motor and configured to move the eyeball fixing unit with respect to the irradiation end unit; and
   a drive controller configured to control driving of the first motor and driving of the second motor to individually actuate the first actuator and the second actuator.

2. The ophthalmic laser surgery apparatus according to claim 1, wherein
   the drive controller controls driving of the second motor to move the eyeball fixing unit so that a movement of the eyeball fixing unit caused by the first actuator is cancelled.

3. The ophthalmic laser surgery apparatus according to claim 1, wherein
   the drive controller controls driving of the second motor so as to control a pressure applied to the patient by the eyeball fixing unit.

4. The ophthalmic laser surgery apparatus according to claim 1, wherein a main body of the second actuator is connected to the laser delivery optical system through a connector and is arranged at a position away from a housing of the irradiation end unit.

5. The ophthalmic laser surgery apparatus according to claim 1, wherein
   the drive controller controls the second motor so that a position of the eyeball fixing unit is maintained constant with respect to the patient's eye when the irradiation end unit and the eyeball fixing unit are moved toward the patient's eye by the first actuator.

6. The ophthalmic laser surgery apparatus according to claim 5, wherein
   the second actuator includes
      a base connected to the laser delivery optical system so as to move together with the irradiation end unit by the first actuator, and
      a movable member configured to be movable with respect to the base and connected to the eyeball fixing unit, and
   the drive controller moves the movable member with respect to the base so that a position of the eyeball fixing unit is maintained constant with respect to the patient's eye when the base is moved together with the irradiation end unit by the first actuator.

7. The ophthalmic laser surgery apparatus according to claim 1,
   wherein the second actuator includes a pressure sensor configured to detect a pressure applied to the patient's eye by the eyeball fixing unit.

8. The ophthalmic laser surgery apparatus according to claim 7,
   wherein the drive controller controls driving of at least one of the first motor and the second motor based on a detection signal output from the pressure sensor.

9. The ophthalmic laser surgery apparatus according to claim 7,
   wherein the drive controller stops driving of the first motor when the eyeball fixing unit and the patient's eye are detected to be in contact with each other, based on a detection signal output from the pressure sensor.

10. The ophthalmic laser surgery apparatus according to claim 7, further comprising:
    a user interface configured to be operated by a user,
    wherein the drive controller controls driving of the second motor based an operational signal output from the user interface.

11. The ophthalmic laser surgery apparatus according to claim 1, wherein
    the second actuator includes a position detection sensor configured to detect a height of the eyeball fixing unit, and
    the drive controller controls driving of at least one of the first motor and the second motor based on a detection signal output from the position detection sensor.

12. The ophthalmic laser surgery apparatus according to claim 11, wherein
    the drive controller stops driving of the first motor and stores the height of the eyeball fixing unit detected by the position detection sensor in a memory as a reference position when the eyeball fixing unit and the patient's eye are detected to be in contact with each other, based on the detection signal output from the pressure sensor, and
    the drive controller drives the first motor to return the eyeball fixing unit to the reference position stored in the memory, after driving the first motor so as to move the irradiation end unit and the eyeball fixing unit toward the patient's eye.

13. The ophthalmic laser surgery apparatus according to claim 1, wherein
the drive controller controls driving of the second motor so as to move the eyeball fixing unit toward the patient's eye, after controlling driving of the first motor to move the irradiation end unit and the eyeball fixing unit toward the patient's eye and completing positioning of the irradiation end unit with respect to the patient's eye.

14. The ophthalmic laser surgery apparatus according to claim 1, further comprising:
a lock mechanism configured to lock moving of the eyeball fixing unit by the second actuator,
wherein the drive controller releases the lock mechanism from locking the eyeball fixing unit while the second motor is driving, and activates the lock mechanism to lock the eyeball fixing unit while the second motor is stopped.

15. An ophthalmic laser surgery apparatus comprising:
an irradiation optical system configured to irradiate a laser beam emitted from a laser source toward a patient's eye;
a laser delivery optical system including:
an irradiation end unit including at least an objective lens, and
at least a portion of the irradiation optical system,
the laser delivery optical system is configured to optically guide the laser beam from the irradiation optical system to the patient's eye;
a first actuator including a first motor and configured to integrally move the irradiation end unit and an eyeball fixing unit toward the patient's eye, the eyeball fixing unit including a suction ring and being connected to the laser delivery optical system;
a second actuator including a second motor and configured to move the eyeball fixing unit with respect to the irradiation end unit, wherein
a main body of the second actuator is connected to the laser delivery optical system through a connector and is arranged at a position away from a housing of the irradiation end unit, and
the second actuator pressurizes the patient's eye with the eyeball fixing unit at a load equal to or less than 300 g.

16. The ophthalmic laser surgery apparatus according to claim 15,
wherein the eyeball fixing unit is detachably attached to the second actuator.

17. An eyeball fixing actuator which is detachably attachable to an ophthalmic laser surgery apparatus, the ophthalmic laser surgery apparatus including (1) an irradiation optical system configured to irradiate a laser beam emitted from a laser source toward a patient's eye, (2) a laser delivery optical system including (i) an irradiation end unit including at least an objective lens, and (ii) at least a portion of the irradiation optical system, the laser delivery optical system is configured to optically guide the laser beam from the irradiation optical system to the patient's eye, and (3) an apparatus-side actuator including a first motor and configured to integrally move the irradiation end unit and an eyeball fixing unit toward the patient's eye, the eyeball fixing unit including a suction ring and being connected to the laser delivery optical system, the eyeball fixing actuator comprising
a second motor configured to move the eyeball fixing unit with respect to the irradiation end unit; and
a drive controller configured to control driving of the second motor to cancel a movement of the eyeball fixing unit caused by the apparatus-side actuator when the apparatus-side actuator moves the irradiation end unit and the eyeball fixing unit toward the patient's eye.

* * * * *